(12) United States Patent
Kaseko et al.

(10) Patent No.: US 8,778,677 B2
(45) Date of Patent: Jul. 15, 2014

(54) METHODS OF GENERATING HYBRID/CHIMERIC CELLS, AND USES THEREOF

(75) Inventors: Galina Kaseko, Waverley (AU); Tohsak L. Mahaworasilpa, Kingsford (AU)

(73) Assignee: BTS Research International PTY. Ltd., Chatswood (AU)

( * ) Notice: Subject to any disclaimer, the term of this patent is extended or adjusted under 35 U.S.C. 154(b) by 0 days.

(21) Appl. No.: 13/377,285

(22) PCT Filed: Jun. 10, 2010

(86) PCT No.: PCT/AU2010/000715
§ 371 (c)(1),
(2), (4) Date: Apr. 3, 2012

(87) PCT Pub. No.: WO2010/141989
PCT Pub. Date: Dec. 16, 2010

(65) Prior Publication Data
US 2012/0088272 A1    Apr. 12, 2012

(30) Foreign Application Priority Data
Jun. 10, 2009 (AU) ............................. 2009902652

(51) Int. Cl.
*C12N 5/00* (2006.01)
(52) U.S. Cl.
USPC ....................................................... 435/346
(58) Field of Classification Search
None
See application file for complete search history.

(56) References Cited

U.S. PATENT DOCUMENTS

| | | | |
|---|---|---|---|
| 2005/0170506 A1 | 8/2005 | Sayre et al. | |
| 2006/0084167 A1 | 4/2006 | Cohenford et al. | |
| 2007/0154995 A1* | 7/2007 | Trakht | 435/70.21 |
| 2012/0088304 A1 | 4/2012 | Kaseko et al. | |

FOREIGN PATENT DOCUMENTS

| | | |
|---|---|---|
| EP | 0292965 A2 | 11/1988 |
| WO | 2010/141990 A1 | 12/2010 |

OTHER PUBLICATIONS

Ainai et al., Renewal of EBV-hybridoma method: efficient generation of recombinant fully human neutralizing IgG antibodies specific for tetanus toxin by use of tetroma cells. Hum Antibodies. 2006;15(4):139-54.
Airoldi et al., Cytokine gene expression in neoplastic B cells from human mantle cell, follicular, and marginal zone lymphomas and in their postulated normal counterparts. Cancer Res. Feb. 15, 2001;61(4):1285-90.
Blackwood et al., Going the distance: a current view of enhancer action. Science. Jul. 3, 1998;281(5373):60-3.
Boerner et al., Production of antigen-specific human monoclonal antibodies from in vitro-primed human splenocytes. J Immunol. Jul. 1, 1991;147(1):86-95.
Carothers et al., Splicing mutations in the CHO DHFR gene preferentially induced by (±)-3 alpha,4 beta-dihydroxy-1 alpha,2 alpha-epoxy-1,2,3,4-tetrahydrobenzo[c]phenanthrene. Proc Natl Acad Sci U S A. Jul. 1990;87(14):5464-8.
Christensen et al., Cell type-specific post-translational modifications of mouse osteopontin are associated with different adhesive properties. J Biol Chem. Jul. 6, 2007;282(27):19463-72. Epub May 11, 2007.
Cullen, Expression of a cloned human interleukin-2 cDNA is enhanced by the substitution of a heterologous mRNA leader region. DNA. Nov. 1988;7(9):645-50.
Durocher et al., High-level and high-throughput recombinant protein production by transient transfection of suspension-growing human 293-EBNA1 cells. Nucleic Acids Res. Jan. 15, 2002;30(2):E9.
Feizi, Demonstration by monoclonal antibodies that carbohydrate structures of glycoproteins and glycolipids are onco-developmental antigens. Nature. Mar. 7-13, 1985;314(6006):53-7.
Girard et al., 100-liter transient transfection. Cytotechnology. Jan. 2002;38(1-3):15-21. doi: 10.1023/A:1021173124640.
Gramer et al., Removal of sialic acid from a glycoprotein in CHO cell culture supernatant by action of an extracellular CHO cell sialidase. Biotechnology (N Y). Jul. 1995;13(7):692-8.
Harada et al., Flt3 ligand promotes myeloid dendritic cell differentiation of human hematopoietic progenitor cells: possible application for cancer immunotherapy. Int J Oncol. Jun. 2007;30(6):1461-8.
Hartmann et al., Mechanism and function of a newly identified CpG DNA motif in human primary B cells. J Immunol. Jan. 15, 2000;164(2):944-52.
Hosoi et al., Optimization of cell culture conditions for G-CSF (granulocyte-colony stimulating factor) production by genetically engineered Namalwa KJM-1 cells. Cytotechnology. Sep. 1991;7(1):25-32.
Hur et al., CD19 signalling improves the Epstein-Barr virus-induced immortalization of human B cell. Cell Prolif. Feb. 2005;38(1):35-45.
Jordan et al., Calcium-phosphate mediated DNA transfer into HEK-293 cells in suspension: control of physicochemical parameters allows transfection in stirred media. Transfection and protein expression in mammalian cells. Cytotechnology. Jan. 1998;26(1):39-47. doi: 10.1023/A:1007917318181.
Kalantarov et al., Development of a fusion partner cell line for efficient production of human monoclonal antibodies from peripheral blood lymphocytes. Hum Antibodies. 2002;11(3):85-96.
Karpas et al., A human myeloma cell line suitable for the generation of human monoclonal antibodies. Proc Natl Acad Sci U S A. Feb. 13, 2001;98(4):1799-804.

(Continued)

*Primary Examiner* — Tracy Vivlemore
*Assistant Examiner* — Karen S Weiler
(74) *Attorney, Agent, or Firm* — Wolf, Greenfield & Sacks, P.C.

(57) ABSTRACT

The present invention relates to hybrid cells and methods for producing hybrid cells. In particular, the invention relates to hybrid cells generated from the hybridization of at least three cells where at least two cells are derived from different lineages. The invention further relates to the use of hybrid cells for the expression of proteins useful in a range of diagnostic, prophylactic, therapeutic and/or research applications.

19 Claims, 36 Drawing Sheets

(56) References Cited

OTHER PUBLICATIONS

Kimura et al., Quantitative analysis of Epstein-Barr virus load by using a real-time PCR assay. J Clin Microbiol. Jan. 1999;37(1):132-6.
Kirman et al., Isolation of native human monoclonal autoantibodies to breast cancer. Hybrid Hybridomics. Dec. 2002;21(6):405-14.
Köhler et al., Continuous cultures of fused cells secreting antibody of predefined specificity. Nature. Aug. 7, 1975;256(5517):495-7.
Li et al., Human antibodies for immunotherapy development generated via a human B cell hybridoma technology. Proc Natl Acad Sci U S A. Mar. 7, 2006;103(10):3557-62. Epub Feb. 27, 2006.
Li et al., Packaging of intron-containing genes into retrovirus vectors by alphavirus vectors. Proc Natl Acad Sci U S A. Mar. 31, 1998;95(7):3650-4.
McIlroy et al., Infection frequency of dendritic cells and CD4+ T lymphocytes in spleens of human immunodeficiency virus-positive patients. J Virol. Aug. 1995;69(8):4737-45.
Meissner et al., Transient gene expression: recombinant protein production with suspension-adapted HEK293-EBNA cells. Biotechnol Bioeng. Oct. 20, 2001;75(2):197-203.
Merika et al., Enhanceosomes. Curr Opin Genet Dev. Apr. 2001;11(2):205-8.
Miyaji et al., Efficient expression of human beta-interferon in Namalwa KJM-1 cells adapted to serum-free medium by a dhfr gene coamplification method. Cytotechnology. Sep. 1990;4(2):173-80.
Miyaji et al., Expression of human beta-interferon in Namalwa KJM-1 which was adapted to serum-free medium. Cytotechnology. Mar. 1990;3(2):133-40.
Miyaji et al., Expression of human lymphotoxin in Namalwa KJM-1 cells adapted to serum-free medium. Cytotechnology. Jul. 1990;4(1):39-43.
Parham et al., Effects of pCIneo and pCEP4 expression vectors on transient and stable protein production in human and simian cell lines. Cytotechnology. May 2001;35(3):181-7. doi: 10.1023/A:1013131415382.
Paulson et al., Tissue-specific expression of sialyltransferases. J Biol Chem. Jul. 5, 1989;264(19):10931-4.
Pham et al., Large-scale transient transfection of serum-free suspension-growing HEK293 EBNA1 cells: peptone additives improve cell growth and transfection efficiency. Biotechnol Bioeng. Nov. 5, 2003;84(3):332-42.
Prohaska et al., Developmental plasticity of lymphoid progenitors. Semin Immunol. Dec. 2002;14(6):377-84.
Satoh et al., Efficient expression of pro-urokinase by human lymphoblastoid Namalwa KJM-1 cells using moloney retroviral promoter. Cytotechnology. 1995-1996;18(3):167-72.
Satoh et al., Stable production of recombinant pro-urokinase by human lymphoblastoid Namalwa KJM-1 cells: host-cell dependency of the expressed-protein stability. Cytotechnology. 1993;13(2):79-88.
Schlaeger et al., Transient gene expression in mammalian cells grown in serum-free suspension culture. Cytotechnology. Jul. 1999;30(1-3):71-83. doi: 10.1023/A:1008000327766.
Shinkawa et al., The absence of fucose but not the presence of galactose or bisecting N-acetylglucosamine of human IgG1 complex-type oligosaccharides shows the critical role of enhancing antibody-dependent cellular cytotoxicity. J Biol Chem. Jan. 31, 2003;278(5):3466-73. Epub Nov. 8, 2002.
Sugimoto et al., Incorrect us of "immortalization" for B-lymphoblastoid cell lines transformed by Epstein-Barr virus. J Virol. Nov. 1999;73(11):9690-1.
Toda et al., Proteome analysis of Epstein-Barr virus-transformed B-lymphoblasts and the proteome database. J Chromatogr B. Apr. 5, 2003;787(1):197-206.
Traggiai et al., An efficient method to make human monoclonal antibodies from memory B cells: potent neutralization of SARS coronavirus. Nat Med. Aug. 2004;10(8):871-5. Epub Jul. 11, 2004.
Urlaub et al., Isolation of Chinese hamster cell mutants deficient in dihydrofolate reductase activity. Proc Natl Acad Sci U S A. Jul. 1980;77(7):4216-20.
Van Dijk et al., Human antibodies as next generation therapeutics. Curr Opin Chem Biol. Aug. 2001;5(4):368-74.
Wang et al., Quantitation of mRNA by the polymerase chain reaction. Proc Natl Acad Sci U S A. Dec. 1989;86(24):9717-21. Erratum in: Proc Natl Acad Sci U S A Apr. 1990;87(7):2865.
Wojcieszyn et al., Studies on the mechanism of polyethylene glycol-mediated cell fusion using fluorescent membrane and cytoplasmic probes. J Cell Biol. Jan. 1983;96(1):151-9.
Zafiropoulos et al., Induction of antigen-specific isotype switching by in vitro immunization of human naive B lymphocytes. J Immunol Methods. Jan. 15, 1997;200(1-2):181-90.
Koeffler et al., Blood, 58:1159-1163 (1981).
Camargo et al., Journal of Clinical Investigation, 113:1266-1271 (2004).
Lubbert et al., Journal of Experimental Medicine, 167:873-886 (1988).
Postlethwaite et al., Journal of Experimental Medicine, 155:168-178 (1982).
Warren et al., Immunology, 54:615-623 (1985).
Zhou et al., Journal of Immunology, 175:2317-2320 (2005).
Hering et al., Biomedica Biochimica Acta, 47:211-216 (1988).
Chung et al., Human embryonic stem cell lines generated without embryo destruction. Cell Stem Cell. Feb 7, 2008;2(2):113-7. doi: 10.1016/j.stem.2007.12.013. Epub Jan. 10, 2008.
Gustafsson et al., SPAM-8, a mouse-human heteromyeloma fusion partner in the production of human monoclonal antibodies. Establishment of a human monoclonal antibody against cytomegalovirus. Hum Antibodies Hybridomas. Jan. 1991;2(1):26-32.
Messer Peters et al., Production of interspecies T cell hybrids which retain differentiation specific surface antigens. J Immunol Methods. Aug. 12, 1983;62(1):39-47.
Treves et al., Establishment of cell lines from somatic cell hybrids between human monocytes and mouse myeloma cells. J Immunol. Feb. 1984;132(2):690-4.

\* cited by examiner

69,XX,-X,inv(2)(q33q35),-3,+der(5)t(5;?),dup(6)(p21.1p23), +inv(7)(p13p22),-9, del(9)(p13),der(9)t(9;9)(p12;q22), der(10)t(3;10)(p21;p24),-13,add(13)(p11.1),-14, add(17)(p13)x2,der(18)t(1;18)(p32;q23),-20,der(21)t(1;21)(q12;p11.1),-22, +marr1, +mar2, +mar3, +mar4, +mar5

CLONE1
47,XY,der(8)t(1;8)(p32;p23),+13,der(14)t(6;14)(p10;p12),dup(17)(q22)

(C)

KBT (CD20+CD72+)&(CD4+CD8+) CLONE 3

67-68,X,der(X)t(X;?;?)(q13;?;?), -X, der(1)t(1;4)(p10;p10), inv(2)(q33q35),-
3,+der(5)t(5;?)(q11.2;?),dup(6)(p21.1p23),+der(7)t(7,mar3)(q10;q10),-9,
del(9)(p13),der(9)t(9;9)(p12;q22), der(10)t(3;10)(p21;p24),-13,add(13)(p11.1),-14,
add(17)(p13)x2,der(18)t(1;18)(p32;q23),-20,der(21)t(1;21)(q12;p11.1),-22, +mar1+mar2,
+mar4, +mar5

(D)

KBT (CD20+CD72+)&(CD4+CD8+) CLONE 4

68,X,der(X)t(X;?;?)(q13;?;?), -X, der(1)t(1;4)(p10;p10), inv(2)(q33q35),-3, -4,
+der(5)t(5;?)(q11.2;?), der(5)t(5;7d/G)(p10;p10), dup(6)(p21.1p23),+der(7)t(7;mar3)(q10;q10),
-9, del(9)(p13),der(9)t(9;9)(p12;q22), der(10)t(3;10)(p21;p24),-13,add(13)(p11.1),-14,
add(17)(p13)x2,der(18)t(1;18)(p32;q23),-20,der(21)t(1;21)(q12;p11.1),-22, +mar1+mar2,
+mar4, +mar5

KWT (CD4+)

129-140,XXXY,-X,-X,-1,-2, inv(2)(q33q35),-3,-3, der(4)t(4;?)(q35;?),+5,
+der(5)t(5;?)(q11.2;?)x2, +6, +dup(6)(p21.1p23), +7, +inv(7)(p13p22)x2,
der(8)t(1;8)(p32;p23),-9,-9, del(9)(p13),der(9)t(9;9)(p12;q22)x2, +der(10)t(3;10)(p21;p24),-12,
add(13)(p11.1),-14,-14,der(14)t(5;14)(p11;p13), -15,-17, add(17)(p13)x2, dup(17)(q22q23)x3,-
18,-18, +20,der(21)t(1;21)(q12;p11.1),-22, +mar1,+mar2x2, +mar3, +mar4, +mar5, +mar11

KWT (CD3+CD5+)

135-142,XXXY,-X,-X,-1,-2, inv(2)(q33q35),-3,-3,-4, der(4)t(4;?)(q35;?),+5,
+der(5)t(5;?)(q11.2;?)x2, +6, +dup(6)(p21.1p23), +inv(7)(p13p22)x2, der(8)t(1;8)(p32;p23),
-9,-9, del(9)(p13),der(9)t(9;9)(p12;q22)x2, +der(10)t(3;10)(p21;p24),-12, add(13)(p11.1),-14,
-14, der(14)t(5;14)(p11;p12); -15,-17, add(17)(p13)x2, dup(17)(q22q23)x2,-18, -18,
+20,der(21)t(1;21)(q12;p11.1),-22, +mar1,+mar2x2, +mar3, +mar4, +mar5, +mar9, +mar11

(A)

KWT (CD4+CD8+) CLONE1

124-139,XXXY, +1, +2,+2, inv(2)(q33q35),-3,+der(5)t(5;7)(q11.2;7), +6, dup(6)(p21.1p23),
+inv(7)(p13p22), der(8)t(1;8)(p32;p23), del(9)(p13), der(9)t(9;9)(p12;q22),+10,+10
+der(10)t(3;10)(p21;p24)X2,+13,+13, add(13)(p11.1),-14, der(14)t(5;14)(p11;p12),
add(17)(p13)x2, +add(17)(p13), dup(17)(q22q23),+18,der(18)t(1;18)(p32;q23),+19,-20,
der(21)t(1;21)(q12;p11.1),-22, +mar1,+mar2, +mar3, +mar4x2, +mar5x2

(B)

KWT (CD4+CD8+) CLONE2

125-131,XXXY, +1, +2,+2, inv(2)(q33q35),-3,+der(5)t(5;7)(q11.2;7), +6, dup(6)(p21.1p23),
+inv(7)(p13p22), der(8)t(1;8)(p32;p23), -9, del(9)(p13), der(9)t(9;9)(p12;q22),+10,+10
+der(10)t(3;10)(p21;p24)X2,+13,+13, add(13)(p11.1),-14, der(14)t(5;14)(p11;p12),
add(17)(p13)x2, +add(17)(p13), dup(17)(q22q23),+18,der(18)t(1;18)(p32;q23),+19,-20,
der(21)t(1;21)(q12;p11.1),-22, +mar1,+mar2, +mar3, +mar4x2, +mar5x2

(A)

(B)

METHODS OF GENERATING HYBRID/CHIMERIC CELLS, AND USES THEREOF

RELATED APPLICATIONS

This application is a national stage filing under 35 U.S.C. §371 of international application PCT/AU2010/000715, filed Jun. 10, 2010, which was published under PCT Article 21(2) in English, the disclosure of which is incorporated by reference herein in its entirety.

TECHNICAL FIELD

The present invention relates to hybrid cells and methods for producing hybrid cells. In particular, the invention relates to hybrid cells generated from the hybridization of at least three cells where at least two cells are derived from different lineages. The invention further relates to the use of hybrid cells for the expression of proteins useful in a range of diagnostic, prophylactic, therapeutic and/or research applications.

BACKGROUND

Any discussion of the prior art throughout the specification should in no way be considered as an admission that such prior art is widely known or forms part of common general knowledge in the field.

A variety of different cell types are currently used to express proteins that are commercially relevant in a range of diagnostic, prophylactic, therapeutic and/or research applications. Currently, the production of such proteins is routinely carried out in cells such as bacteria, yeast, fungi, insect and non-human mammalian cells.

Cells frequently modify proteins with a multitude of post-translational modifications including, but not limited to, glycosylation, acylation, phosphorylation, methylation, sulfation, prenylation and lipidation. These modifications are species specific and, as such, the cells currently used in the production of commercially relevant proteins exhibit post-translational modifications that are distinct from the post-translational modifications observed on proteins expressed from human cells or occurring naturally in the human body. For example many non-mammalian cell types used to produce commercially relevant proteins either lack the capacity to glycosylate proteins or exhibit glycosylation patterns that are different to the glycosylation patterns exhibited by proteins expressed in human cells.

Even in non-human mammalian expression systems such as Chinese hamster ovary (CHO) cells, significant differences in the glycosylation patterns are documented compared with that of human cells. For example, CHO cell lines used for recombinant protein expression lack a functional ($\alpha$ 2, 6) sialyltransferase enzyme for synthesis of ($\alpha$ 2, 6)-linked terminal sialic acids which are present in human cells. Furthermore, the sialic acid motifs that are present on CHO-cell-expressed glycoproteins are prone to degradation by a CHO cell endogenous sialidase (Gramer et al. Biotechnology 13 (7):692-&, 1995).

As a result of the distinct post-translational modification repertoires of non-human expression systems, proteins expressed from them may exhibit physiochemical and pharmacological characteristics such as half-life, immunogenicity, stability and functional efficacy that are distinct from human cell-derived proteins. This can substantially impact on the clinical utility of these proteins.

There is also growing evidence that in addition to its species-dependent nature, post-translational modifications can also be tissue- and even cell type specific within the same species. This is particularly relevant to tissue- and cell type-specific expression of proteins exhibiting terminal glycosylation (Feizi Nature 314: 53-54, 1985; Rademacher et al Annu Rev Biochem 57: 785-838, 1988). Specifically, it has been shown that three sialyltransferases, which attach terminal sialic acids to glycoprotein sugar chains, exhibit striking differential expression in seven tissues of the rat (Paulson et al J. Biol. Chem. 264: 10931-10934, 1989). This provides support for tissue specific glycosylation of the same protein. Furthermore, studies with two isoforms of a highly phosphorylated glycoprotein (mouse osteopontin) expressed by mouse fibroblasts and mouse osteoblasts from bone marrow exhibited major differences in their degree of phosphorylation, which correlated with differences in biological activity. These results indicate that the function of osteopontin produced by different cell types is distinct (Christensen et al J. Biol. Chem. 282(27): 19463-19472).

Efficacious cell systems suitable for the production of biologics exhibiting fully human characteristics ideally should satisfy a number of criteria, including but not limited to:
a) derivation from human tissue;
b) high density growth in culture;
c) exhibit commercially viable protein yields;
d) allow stable foreign gene introduction;
e) permit gene amplification methods;
f) allow use of a parent cell for monoclonal antibody production as in human-human hybridomas;
g) exhibit stable long-term protein expression;
h) the ability to grow in a serum-free and glutamine-free medium;
i) lack endo-peptidase activity, thus reducing protein degradation,
j) be free of pathogenic agents including viral DNA and mycoplasma;
k) produce proteins that exhibit post-translational modifications that are functionally similar to, or the same as post-translational modifications that occur on naturally-occurring human proteins, preferably tissue and cell specific. These post-translational modifications may include, but are not limited to, carbohydrate moieties on glycoproteins.

Whilst a number of human host cells or heterohybridomas exist for the expression of human protein, none of them successfully satisfy all of the criteria listed above. Most notably, attempts to express and isolate proteins from existing human cell expression systems in clinically useful yields have resulted in limited success.

Protein expression in eukaryotic cells is controlled at multiple stages, including: (a) the influence of regulatory factors on the genes in the chromatin; (b) regulation of initiation of transcription; and (c) post-translational modification. These different stages are thought to be developmental stage- and/or tissue-specific. Thus, when an exogenous gene encoding a desired protein is incorporated into a cell, expression of the desired protein may be less than optimal. Problems such as lack of stable expression (Li et al., Proc Natl Acad Sci USA 95: 3650-3654, 1998; Miyaji et al., Cytotechnology, 3: 133-140, 1990; Miyaji et al., Cytotechnology 4: 173-180, 1990; Miyaji et al., Cytotechnology 4: 39-43, 1990; Satoh et al., Cytotechnology 13: 79-88, 1993), low expression yields (Airoldi et al, Cancer Research 61:1285-1290, 2001; Hosoi et al. Cytotechnology 7: 25-32, 1991) and non-optimal post-translational modifications (Shinkawa et al., J. Biol. Chem.

278:3466-3473, 2003) may result. All of these factors may influence the potential commercial utility of the protein.

As one example, a subline of Namalwa cells (human B lymphoblastoid cells grown in suspension cultures and adapted to a serum and albumin-free medium), Namalwa KJM-1, was used for large scale production of alpha-interferon, which is an endogenous protein to Burkitt's lymphoma cells. However, when G-CSF protein foreign to Burkitt's lymphoma cells but endogenous for B cells (Airoldi et al, Cancer Research 61:1285-1290, 2001) was used as targeted protein for transfection via electroporation, the levels of G-CSF expression varied among multiple methotrexate (MTX) resistant clones and the highest G-CSF-producer clone had a specific productivity of only 2.4 μg/ml/day when adapted to serum free conditions.

Further, the specific productivity was depressed at high density culture when the cell number was above $7 \times 10^5$ cells/ml (Hosoi et al. Cytotechnology 7: 25-32, 1991). Even though the reported maximum G-CSF concentration was markedly improved and reached 41 μg/ml, in order to achieve this, it required extensive and laborious manipulation of cell culture conditions with very tight control of pH. It also showed that the medium used for the optimal growth was different from that used for the optimal production, thus creating significant conflict between desired high density and high production rate, and resulting in an industrially non-viable system.

Because gene expression in eukaryotes is controlled in multiple steps, which include: (a) availability and accessibility of regulatory factors to the genes in the chromatin; (b) modulation on accessible promoters of the rate of specific initiation of transcription; and (c) subsequently post-transcriptional events at various steps, the presence of tissue specific and development specific transcription factors has a great influence on the expression of genes. Further, the gene regulation of a specific cell type requires cooperation of several cis-acting DNA regulatory sequences, which are binding sites for proteins that transmit molecular signals to genes (Blackwood et al., Science 281: 60-63, 1998). These sequences bind regulatory proteins to form complexes known as enhanceosomes (Marika et al., Curr Opin Genet Dev 11(2): 205-208, 2001). Thus, the further the targeted gene is away from its usual cellular environment when introduced into the human lineage specific host cells, stable expression and production of desired protein at high production levels are reduced. When Namalwa KJM-1 cells were transfected with genes of foreign proteins further away from being lineage specific proteins for lymphoblastoid cell lines such as beta interferon (Miyaji et al., Cytotechnology, 3: 133-140, 1990; Miyaji et al., Cytotechnology 4: 173-180, 1990) or human lymphotoxin (Miyaji et al., Cytotechnology 4: 39-43, 1990) or pro-urokinase (Satoh et al., Cytotechnology 13: 79-88, 1993), the transfection rate and the cell productivity were found to be even lower.

Efficient expression of foreign genes in human lineage specific cell lines also requires a careful, and sometimes, tedious selection of a suitable enhancer/promoter which would contain binding sites for nuclear factors available from human host cells. Finding such an enhancer/promoter might still result in limited suitability of such a promoter. For example, when several enhancers/promoters such as the simian virus 40 (SV40) early gene promoter, human cytomegalovirus (hCMV) major immediate-early gene promoter, Moloney murine leukaemia virus (Mo-MuLV) promoter, Rous sarcoma virus (RSV) promoter and chicken β-actin promoter, were investigated for more efficient expression of a foreign gene in Namalwa KJM-1 cells, the Mo-MuLV promoter was found to be about 10 times stronger than traditional SV40 earlier promoter and the high producer clones reached productivity of 30-40 μg/$10^6$ cells/day (Satoh et al., Cytotechnology 18:162-172, 1996). However, the problem with using retroviral vectors such as Mo-MuLV is that it is difficult to use for transfection of genes with inverting sequences (introns) because of their removal by the nuclear splicing machinery (Li et al., Proc Ntl Acad Sci USA 95: 3650-3654, 1998).

The mismatch between cellular and nuclear environment is augmented even further in the case of the proteins encoded by two genes such as antibodies. Further, whilst Namalwa KJM-1 cells were used for generation of human-human hybridomas, the antibody yields made this cell line unsuitable for industrial production.

As another example, human embryonic kidney cell line 293 has proven to be very easily transfected with genes of foreign origins with a high degree of stability. However, proteins derived from 293 transfectants have limited use and are usually suited for research purposes only because 293 cells include human adenovirus Ad5 DNA (HEK 293 cells). However, the greatest limitation in using the 293 cells in a commercial setting is its adherent nature. A number of attempts have been made to adapt 293 cells for efficient transfection in suspension using cost effective vehicles such as polyethyleneimine (Durocher et al., Nucleic Acids Res 30(2):e9, 2002; Schlaeger et al., Cytotechnology 30:71-83, 1999) or calcium phosphate (Girard et al, Cytotechnology 38:15-21, 2002; Jordan et al., Cytotechnology 26:39-47, 1998; Meissner et al., Biotechnol Bioeng 75(2):197-203, 2001). However, these vehicles result only in transient expression of recombinant proteins meaning that the transfection has to be repeated for each new batch of seeded culture. In order to achieve suspension growth and higher protein expression when EBV's oriP is present in the vector backbone, the 293 cells had to be genetically modified to stably express the Epstein Barr virus EBNA1 protein (293E) (Durocher et al., Nucleic Acids Res 30(2):e9, 2002; Parham et al., Cytotechnology 35:181-187, 2001; Schlaeger et al., Cytotechnology 30:71-83, 1999). Even after the transfection with EBNA1, the 293E cells when grown in serum free medium (HEK293 EBNA1), (prerequisite for large scale production) exhibit a very poor transfection rate most likely due to the presence of polyanions (heparin, dextran sulphate) that are added to prevent cell aggregation. Attempts have been made to mitigate this problem by supplementing medium with peptones obtained from enzymatic hydrolysis of animal sources such as meat, gelatin and casein (Pham et al., Biotechnol Bioeng 84(3):332-42, 2003). When HEK293 EBNA1 cell line was used for the production of Tie-2 (receptor tyrosine kinase for angiopoietin growth factors) and Neuropilin-1 ED (receptor that mediates neuronal cell guidance) the protein expression was limited by the low cell density cultures obtained when compared to those obtained in untransfected cultures. Also, the purity of >95% of resulting protein is suitable for research grade products only. In addition, the HEK293 EBNA1 cells are not suitable for production of monoclonal antibodies (mAbs).

Current strategies for production of therapeutic mAbs include the use of mammalian cell systems (i.e. CHO or NS0 transfectomas) to recombinantly produce mAbs derived from immunization of transgenic mice bearing human Ig genes (xenomice), humanization of rodent mAbs, or through screening of human mAb libraries (van Dijk et al., Curr. Opin. Chem. Biol. 5:368-374, 2001). Whilst in terms of their sequence, therapeutic mAbs have recently evolved into chimeric (rodent variable and human constant regions), humanized (human sequence except for rodent complementary-determining regions), and fully human antibodies (human Abs) to minimise the allergic response, the important aspect of a therapeutic mAb is its ability to elicit immune effector functions, such as antibody-dependent cellular cytotoxicity which is compromised if mAb is produced in non-human host cells that alter its native glycosylation pattern (Shinkawa et al., J. Biol. Chem. 278:3466-3473, 2003). In view of these facts, an ideal scenario is one where therapeutic antibodies are produced by human cells. In this case, fully human mAbs would be able to exert human effector functions and have very limited immunogenicity because of their native human structure.

The generation of hybridomas or Epstein-Barr virus (EBV)-transformed lymphoblastoid lines derived from human B cells has been reported (Kirman et al., Hybrid. Hybridomics 21: 405-414, 2002; Boerner et al., J. Immunol. 147: 86-95, 1991; Zafiropoulos et al., J. Immunol. Methods 200: 181-190, 1997). However, there is limited information on the characterization of these mAbs and the lines with respect to their long-term stability and suitability to manufacturing processes, especially the production levels and stability of Ig secretion during the entire batch manufacturing. Whilst cell lines producing human mAbs against human GM-CSF at cumulative titre of 1.2 g/litre during a 4-day run have been reported, these cell lines were derived from somatic cell hybridisation (fusion) of primary human B cells with heteromyelolymphoma K6H6/B5 cells (i.e. a mouse-human cell line obtained from a hybridisation of a human B cell lymphoma and a mouse myeloma cell (Li et al., Proc Natl Acad Sci USA 103(10):3557-3562, 2006).

In the instance of EBV-transformation, the difficulty has been the establishment of a completely immortalized human B cell line while maintaining stable antibody production. This is due to low efficacy of immortalization, the arrest of cell growth, and the dominant immortalization of IgM producing cells. Additionally, recent reports have shown that most EBV-transformed B cells have shortened telomeres and a limited life span, mostly before 160 population doubling levels (Sugimoto et al., J Virol 73:9690-9691, 1999; Toda et al., J Chromatogr B Analyt. Technol. Biomed. Life Sci. 787:197-206, 2003). In order to overcome this problem, attempts have been made to hybridise (or fuse) EBV-transformed B cells with a suitable partner cell line (expression system) but in effect these partner cell lines represented various combination of heterohybrids such as a trioma derived from a mouse-human heterohybridoma with a human B cell (Ainai et al., Hum Antibodies 15:139-154, 2006; Kalantarov et al., Hum Antibodies 11: 85-96, 2002; Karpas et. al., Proc Natl Acad Sci USA 98:1799-1804, 2001). When such a trioma was fused with primary EBV-transformed B cells producing an antibody to tetanus toxin (TT), it resulted in a tetroma having a quarter of the mouse component. Although stable production of mAbs to TT was possible after three-time consecutive cloning of tetromas, such repeated cell cloning steps are laborious and time-consuming. In addition, although the quantities of the mAbs produced by tetromas were sufficient for experimental purposes, the levels were insufficient for large-scale production of mAbs as pharmaceutical agents. It is still questionable whether immortalization in the presence of polyclonal activator CpG 2006 or co-ligation of CD19 or BCR might result in a complete system for an efficient production of specific mAbs in appropriate volumes for therapeutic use (Hartman et al., J Immunol 164: 944-953, 2000; Hur et al., Cell Prolif 38: 35-45, 2005; Traggiai et al., Nat Med 10: 871-875, 2004).

A number of approaches have been tried to use human cells for the production of biological substances such as growth factors, antibodies and soluble proteins.

It is an object of the present invention to overcome or ameliorate at least one of the disadvantages of the prior art, or to provide a useful alternative.

SUMMARY OF INVENTION

It is generally considered that multi-fusion cells are unstable and that the more cells involved in a fusion, the greater the instability of the resulting hybrid cell. Surprisingly, in the present invention hybrid cells resulting from the fusion of a number of cells, for example three cells, exhibit functional stability. In particular, it has been found that cells derived from different lineages can be somatically fused or hybridised to form substantially stable chimeric/hybrid cells. More particularly, the present invention relates to cross-lineage chimeric/hybrid cells generated from the hybridisation of at least three parental cells resulting in a tri-hybrid where at least two parental cells are derived from different lineages and wherein a myeloma cell is not included in the hybridisation.

It has also surprisingly been found that the stable chimeric/hybrid cells of the invention have applications, for example, in the production of proteins which exhibit desired post-translational modifications such as, but not limited to, human glycosylation patterns.

It has also surprisingly been found that expression levels of a desired protein from the stable chimeric/hybrid cells of the invention may be enhanced when a second desired protein is simultaneously expressed from the chimeric/hybrid cells of the invention. Moreover, expression levels of two target proteins may be enhanced by the simultaneous expression of a third desired protein from the chimeric/hybrid cells of the invention.

Accordingly, the present invention provides significant advantages over previously known systems in terms of versatility and stability of the hybrid cells. In one embodiment, the hybrid cells of the invention are produced by the fusion of two identical cells or two cells of the same lineage and a cell of a different lineage. Such a hybrid is predisposed to a phenotype directed towards the majority cell type used in the hybridisation. These hybrid cells can be used specifically to express proteins in which tissue-specific post-translation modifications are known to be important for protein functionality. For example, a cytokine known to have a specific functional post-translational modification when expressed from a B cell may be more efficiently expressed from a hybrid cell that includes at least two cells derived from a B cell lineage thus ensuring functional post-translation modification.

As post-translational modification of proteins may be tissue- or cell type-specific, it will be clear to the skilled addressee that hybrid cells of the invention may also be enriched for a particular cell type or phenotype (as evidenced by the presence of specific CD markers) to permit the expression of a protein exhibiting a desired post-translational modification or desired functionality associated with a particular cell type or phenotype.

In one embodiment, the present invention relates to hybrid cells including the use of at least one immortalised cell. However, it will be clear to the person skilled in the art that the present invention also relates to the fusion of non-immortalised cells which may subsequently be immortalised by an in vitro transformation process such as the introduction of viral genes eg Epstein-Barr virus (EBV), Simian virus 40 (SV40) T antigen, adenovirus E1A and E1B, and human papillomavirus (HPV) E6 and E7. Alternatively, non-immortalised cells may be immortalised via expression of the telomerase reverse transcriptase protein (TERT). Immortalised cells may also be derived from cells in which oncogene expression has been modified. Immortalised cells may further be derived from any action that induces a capacity for indefinite growth including but not limited to UV exposure or spontaneous transformation in which the mechanism for immortality is not known.

It will be clear that the present invention relates in one embodiment to the fusion of three individual cells. In an alternative embodiment, the present invention relates to the fusion of three populations of cells wherein each population includes a plurality of identical cell types. The person skilled in the art would understand that the fusion of populations of cells could be carried out in bulk cell cultures. Desired hybridised cells may then be identified and isolated by methods well known in the art, for example via selective media, such as hypoxanthine aminopterin thymidine (HAT) medium. Alternatively, fused cells may be identified and isolated via the identification of specific cell markers, such as CD markers.

It will be clear that the isolation of cells on the basis of their expression of markers such as CD markers as well as enrichment of a cell for a particular cell type or phenotype may be accomplished by methods well known in the art, such as fluorescent-activated cell sorting (FACS) methods.

It will also be clear that the cells of the present invention may be stably or transiently transfected with DNA encoding a desired protein. These stable or transiently transfected cells may be identified by methods well known in the art, such as by including a selection reporter gene in the DNA used in the transfection. Such reporter genes may include genes which would enable transfected cells to grow in a compound-deficient medium, for example the dihydrofolate reductase (dhFr) gene. Reporters could also include genes which confer visual identification of transfected cells, for example, the luciferase gene or a green fluorescent protein (gfp) gene. Alternatively, the reporter gene could confer resistance to a particular compound eg G418. Such reporter genes are well known in the art.

In one preferred embodiment, the hybrid cells of the invention may be used to express monoclonal antibodies. Traditionally, monoclonal antibody production has been performed via the fusion of a myeloma cell and a B cell derived from the spleen of an immunised animal such as a mouse. However, myeloma cell instability and in particular genomic instability may result in less than satisfactory expression of the desired antibody. Additionally, because animal cells are used in the production of hybridomas, the antibodies produced exhibit non-human post-translational modifications. Antibodies with non-human post-translational modifications may result in significant problems when the antibodies are used as human therapeutics. These problems may include reduced effector function of the antibody as well as immunogenicity resulting in an unsatisfactory in vivo half-life and thus reduced in vivo efficacy. There is also evidence to suggest hybrids cannot successfully be produced in the absence of a myeloma cell. The hybrid cells of the invention have surprisingly shown that stable hybrids may be produced in the absence of a myeloma cell. Moreover, antibodies expressed from the hybrid cells of the invention address the problems associated with the use of monoclonal antibodies produced by hybridomas. These antibodies exhibit humanised post-translational modifications and are expressed from cells that exhibit functional stability.

According to a first aspect, the present invention provides a hybrid cell generated by hybridisation of:
  a first cell, wherein said first cell is a stem cell or a cell derived from an uncommitted progenitor cell;
  a second cell derived from a common lymphoid progenitor cell; and
  a third cell derived from a common lymphoid progenitor cell,
and wherein said first cell is not a myeloma cell.

In one embodiment, said second cell is a cell derived from B lymphoid lineage and said third cell is a cell derived from B lymphoid lineage.

In another embodiment, said second cell is a cell derived from T lymphoid lineage and said third cell is derived from T lymphoid lineage.

In another embodiment, said second cell is a cell derived from B lymphoid lineage and said third cell is a cell derived from T lymphoid lineage.

Preferably, said first cell is a cell derived from a common myeloid progenitor cell. As such, it is clear that the invention provides a hybrid cell generated by hybridisation of a common myeloid progenitor cell or a stem cell, and two B lymphoid cells or two T lymphoid cells. The invention also provides a hybrid cell generated by hybridisation of a common myeloid progenitor cell, or a stem cell, a B lymphoid cell and a T lymphoid cell.

Preferably said cell derived from a common myeloid progenitor cell, is a myelomonocytic progenitor, monocyte, macrophage, eosinophil, neutrophil, dendritic cell or basophil. As such it is clear that the invention provides a hybrid cell generated by hybridisation of a myelomonocytic progenitor, monocyte, macrophage, eosinophil, neutrophil, dendritic cell or basophil and two B lymphoid cells or two T lymphoid cells. The invention also provides a hybrid cell generated by hybridisation of a myelomonocytic progenitor, monocyte, macrophage, eosinophil, neutrophil, dendritic cell or basophil, a B lymphoid cell and a T lymphoid cell.

Preferably said cell derived from a common myeloid progenitor cell displays at least one of the following CD antigens CD16, CD15 or CD14. As such it is clear that the invention provides a hybrid cell generated by hybridisation of a common myeloid progenitor cell that displays at least one of the following CD antigens CD16, CD15 or CD14 and two B lymphoid cells or two T lymphoid cells. The invention also provides a hybrid cell generated by hybridisation of a hybrid cell generated by hybridisation of a common myeloid progenitor cell that displays at least one of the following CD antigens CD16, CD15 or CD14, a B lymphoid cell and a T lymphoid cell.

In one embodiment, said cell derived from a common myeloid progenitor cell is a monocyte. As such, the invention provides a hybrid cell generated by hybridisation of a monocyte and two B lymphoid cells or two T lymphoid cells. The invention also provides a hybrid cell generated by hybridisation of a monocyte, a B lymphoid cell and a T lymphoid cell.

In another embodiment, said cell derived from a common myeloid progenitor cell is a primary myelomonocytic progenitor. As such, the invention provides a hybrid cell generated by hybridisation of a primary myelomonocytic progenitor and two B lymphoid cells or two T lymphoid cells. The invention also provides a hybrid cell generated by hybridisation of a primary myelomonocytic progenitor, a B lymphoid cell and a T lymphoid cell.

In one embodiment, said cell derived from a common myeloid progenitor cell is an immortalised cell. As such, it is clear that the invention provides a hybrid cell generated by hybridisation of an immortalised cell selected from a myelomonocytic progenitor, monocyte, macrophage, eosinophil, neutrophil, dendritic cell or basophil and two B lymphoid cells or two T lymphoid cells. The invention also provides a hybrid cell generated by hybridisation of an immortalised cell selected from a myelomonocytic progenitor, monocyte, macrophage, eosinophil, neutrophil, dendritic cell or basophil, a B lymphoid cell and a T lymphoid cell.

In another embodiment, said cell derived from a common myeloid progenitor cell is derived from spleen, peripheral blood, umbilical cord blood or bone marrow. As such, it is clear that the invention provides a hybrid cell generated by hybridisation of a common myeloid progenitor cell derived from spleen, peripheral blood, umbilical cord blood or bone marrow and two B lymphoid cells or two T lymphoid cells. The invention also provides a hybrid cell generated by hybridisation of a common myeloid progenitor cell derived from spleen, peripheral blood, umbilical cord blood or bone marrow, a B lymphoid cell and a T lymphoid cell.

In another embodiment, said cell derived from B lymphoid lineage is a pre-B cell, an immature B cell, a naïve B cell, an activated B cell or an effector B cell. As such, it is clear that the invention provides a hybrid cell generated by hybridisation of a common myeloid progenitor cell or a stem cell and two B lymphoid cells selected from a pre-B cell, an immature B cell, a naïve B cell, an activated B cell or an effector B cell. The invention also provides a hybrid cell generated by hybridisation of a common myeloid progenitor cell or stem cell, a B lymphoid cell selected from a pre-B cell, an immature B cell, a naïve B cell, an activated B cell or an effector B cell and a T lymphoid cell.

In one embodiment, said effector B cell is an antigen-experienced B-cell or a plasma cell. As such, the invention provides a hybrid cell generated by hybridisation of a common myeloid progenitor cell or stem cell and two B lymphoid cells selected from an antigen-experienced B-cell or a plasma cell. The invention also provides a hybrid cell generated by hybridisation of a common myeloid progenitor cell or stem cell, an antigen-experienced B-cell or a plasma cell and a T lymphoid cell.

In one embodiment, said cell derived from B lymphoid lineage displays at least one of the following CD antigens CD19, CD20, CD72 or CD5. As such, the invention provides a hybrid cell generated by hybridisation of a common myeloid progenitor cell or stem cell and two B lymphoid cells which display at least one of the following CD antigens CD19, CD20, CD72 or CD5. The invention also provides a hybrid cell generated by hybridisation of a common myeloid progenitor cell or stem cell, a B lymphoid cell which displays at least one of the following CD antigens CD19, CD20, CD72 or CD5 and a T lymphoid cell.

In one embodiment, said cell derived from T lymphoid lineage is a pre-T cell, an immature T cell, a naïve T cell, an activated T cell or an effector T cell. As such, the invention provides a hybrid cell generated by hybridisation of a common myeloid progenitor cell or stem cell, a B lymphoid cell and a T lymphoid cell selected from a pre-T cell, an immature T cell, a naïve T cell, an activated T cell or an effector T cell. The invention also provides a hybrid cell generated by the hybridisation of a common myeloid progenitor cell or stem cell and two T lymphoid cells selected from a pre-T cell, an immature T cell, a naïve T cell, an activated T cell or an effector T cell.

In one embodiment, said cell derived from T lymphoid lineage displays at least one of the following CD antigens CD3, CD4, CD5 or CD8. As such, the invention provides a hybrid cell generated by hybridisation of a common myeloid progenitor cell or stem cell, a B lymphoid cell and a T lymphoid cell which displays at least one of the following CD antigens CD3, CD4, CD5 or CD8. The invention also provides a hybrid cell generated by hybridisation of a common myeloid progenitor cell or stem cell and two T lymphoid cells selected from T cells that display at least one of the following CD antigens CD3, CD4, CD5 or CD8.

In one embodiment, said cell derived from B lymphoid lineage is an immortalised cell. As such, the invention provides a hybrid cell generated by hybridisation of a common myeloid progenitor cell or stem cell and two B lymphoid cells, at least one of which can be an immortal cell. The invention also provides a hybrid cell generated by hybridisation of a common myeloid progenitor cell or stem cell, an immortal B lymphoid cell and a T lymphoid cell.

In one embodiment, said cell derived from T lymphoid lineage is an immortalised cell. As such, the invention provides a hybrid cell generated by hybridisation of a common myeloid progenitor cell or stem cell, a B lymphoid cell and an immortal T lymphoid cell.

In one embodiment, said cell derived from B lymphoid lineage is derived from lymphoid tissue. As such, the invention provides a hybrid cell generated by hybridisation of a common myeloid progenitor cell or stem cell and two B lymphoid cells derived from lymphoid tissue. The invention also provides a hybrid cell generated by hybridisation of a common myeloid progenitor cell or stem cell, B lymphoid cell derived from lymphoid tissue and a T lymphoid cell.

In one embodiment, said cell derived from T lymphoid lineage is derived from lymphoid tissue. As such, invention provides a hybrid cell generated by hybridisation of a common myeloid progenitor cell or stem cell, B lymphoid cell tissue and a T lymphoid cell derived from lymphoid tissue.

Where the B or T lymphoid cells included in the hybrid cells of the invention are derived from lymphoid tissue said lymphoid tissue is preferably selected from peripheral blood, cord blood, spleen, bone marrow, thymus, tonsils, adenoids, and regional lymph node.

In one embodiment, at least one of the cells included in the generation of the hybrid cell of the invention is a human cell. It will also be clear that in one embodiment, the hybrid cell of the invention may include at least one mouse cell.

In one embodiment, said cell derived from a common myeloid progenitor cell is a K562 cell. As such, it will be clear that the invention provides a hybrid cell generated by hybridisation of a K562 cell and two B lymphoid cells. The invention also provides a hybrid cell generated by hybridisation of a K562 cell, an immortal B lymphoid cell and a T lymphoid cell.

In one embodiment, said second cell or said third cell is a WIL2-NS cell or a MOLT4 cell. As such, it will be clear that the invention provides a hybrid cell generated by hybridisation of a common myeloid progenitor cell or stem cell, a WIL2-NS cell and a T lymphoid cell. The invention also provides a hybrid cell generated by hybridisation of a common myeloid progenitor cell or stem cell, a B lymphoid cell and a MOLT4 cell.

In one embodiment, said first cell is a K562 cell, said second cell is a WIL2-NS cell and said third cell is a MOLT4 cell.

In another embodiment, said first cell is a K562 cell, said second cell is a primary B cell and said third cell is a primary T cell.

In another embodiment, said first cell is a primary human monocyte, said second cell is a WIL2-NS cell and said third cell is a primary T cell.

In another embodiment, said first cell is a primary human myelomonocytic progenitor, said second cell is a WIL2-NS cell and said third cell is a primary human T cell.

In another embodiment, said first cell is a K562 cell, said second cell is a WIL2-NS cell and said third cell is a primary T cell.

In another embodiment, said first cell is a primary monocyte, said second cell is a WIL2-NS cell and said third cell is a WIL2-NS cell.

In another embodiment, said first cell is a primary mouse monocyte, said second cell is an SP2 cell and said third cell is a primary mouse T cell.

In another embodiment, said first cell is a primary mouse monocyte, said second cell is an SP2 cell and said third cell is a SP2 cell.

In another embodiment, said first cell is a primary human or mouse monocyte, said second cell is a WIL2-NS cell and said third cell is an SP2 cell.

In one embodiment, the hybrid cell of the invention expresses a desired protein. In another embodiment, the hybrid cell of the invention expresses more than one desired protein. In certain embodiments, the hybrid cell of the invention expresses two desired proteins. In other embodiments, the hybrid cell of the invention expresses three desired proteins. In one embodiment said desired protein is an endogenous protein and where more than one desired protein is expressed, at least one of the desired proteins is an endogenous protein. In another embodiment, said protein is a recombinant protein and where more than one desired protein is expressed, at least one of the desired proteins is a recombinant protein. Preferably said protein is a cytokine eg a colony stimulating factor or an interleukin. In one embodiment said protein is GM-CSF. In another embodiment, said protein is interleukin 2. In yet another embodiment, said protein is a receptor or fragment thereof. In one embodiment, said protein is a soluble receptor. In a further embodiment, said protein is an immunoglobulin.

In one embodiment, said protein is a human IL-4 receptor alpha chain. In another embodiment said protein is IgM. In yet another embodiment, said protein is IgG. In a still a further embodiment said protein is CD54.

In one embodiment where the hybrid cell of the invention expresses more than one desired protein, preferably the desired proteins are selected from a cytokine, a colony stimulating factor, an interleukin or a receptor or fragment thereof. In a particular embodiment the desired proteins are an immunoglobulin such as IgM and in particular human soluble IgM; a cytokine, for example an interleukin and in particular interleukin-2 (IL-2) and more particularly human IL-2; and/or a receptor, in particular an interleukin receptor and more particularly a human interleukin receptor and even more particularly human interleukin-4 receptor alpha (IL-4Ra).

The skilled addressee will understand that the hybrid cells of the invention are not limited to expressing particular desired proteins nor are they limited to expressing a certain number of proteins. Moreover, it will be clear to the skilled addressee that simultaneous expression of desired proteins from the hybrid cells of the invention can result in the enhancement of desired protein expression levels.

In one embodiment, said hybridisation used to generate the hybrid cell of the invention is achieved by electrical means. In another embodiment, said hybridisation to generate the hybrid cell of the invention is achieved by chemical means.

In one embodiment, the hybrid cell of the invention is further hybridised with a cell that expresses a protein of interest.

In a particular embodiment the hybrid cell of the invention is hybridised with a B lymphocyte which displays CD25 antigen.

In a particularly preferred embodiment, the hybrid cell of the invention displays CD25 antigen and expresses an immunoglobulin. In a further embodiment, the hybrid cell of the invention is hybridised with a B lymphocyte which displays CD25 antigen and the resulting cell expresses an immunoglobulin.

In one embodiment, said hybridisation used to generate the hybrid cell of the invention is carried out by hybridising three individual cells.

In another embodiment, said hybridisation used to generate the hybrid cell of the invention is carried out using three populations of cells wherein each said population includes a plurality of identical cell types or phenotypes.

In one embodiment, said hybrid cell of the invention is enriched for a particular cell type-defining marker to permit the expression of a protein exhibiting a desired post-translational modification or desired functionality.

In another aspect, the invention provides a method of producing a protein said method comprising the step of expressing a protein in a hybrid cell according to the invention.

In another aspect, the invention provides a protein when produced in a hybrid cell according to the invention.

In another aspect, the invention provides a method of producing a hybrid cell according to the invention wherein said method includes the step of hybridising:
 a first cell, wherein said first cell is a stem cell or a cell derived from an uncommitted progenitor cell;
 a second cell derived from a common lymphoid progenitor cell; and
 a third cell derived from a common lymphoid progenitor cell,
and wherein said first cell is not a myeloma cell.

In one embodiment of the method of the invention, said second cell is a cell derived from B lymphoid lineage and said third cell is a cell derived from B lymphoid lineage.

In another embodiment of the method of the invention, said second cell is a cell derived from T lymphoid lineage and said third cell is derived from T lymphoid lineage.

In another embodiment of the method of the invention, said second cell is a cell derived from B lymphoid lineage and said third cell is a cell derived from T lymphoid lineage.

Preferably, said first cell is a cell derived from a common myeloid progenitor cell. As such, it is clear that the invention provides method of producing a hybrid cell by hybridisation of a common myeloid progenitor cell or a stem cell, and two B lymphoid cells or two T lymphoid cells. The invention also provides a method of producing a hybrid cell by hybridisation of a common myeloid progenitor cell, or a stem cell, a B lymphoid cell and a T lymphoid cell.

Preferably said cell derived from a common myeloid progenitor cell, is a myelomonocytic progenitor, monocyte, macrophage, eosinophil, neutrophil, dendritic cell or basophil. As such, it is clear that the invention provides a method of producing a hybrid cell by hybridisation of a myelomonocytic progenitor, monocyte, macrophage, eosinophil, neutrophil, dendritic cell or basophil and two B lymphoid cells or two T lymphoid cells. The invention also provides a method of producing a hybrid cell by hybridisation of a myelomonocytic progenitor, monocyte, macrophage, eosinophil, neutrophil, dendritic cell or basophil, a B lymphoid cell and a T lymphoid cell.

Preferably said cell derived from a common myeloid progenitor cell displays at least one of the following CD antigens CD16, CD15 or CD14. As such it is clear that the invention provides a method of producing a hybrid cell by hybridisation of a common myeloid progenitor cell that displays at least one of the following CD antigens CD16, CD15 or CD14 and two B lymphoid cells or two T lymphoid cells. The invention also provides a method of producing a hybrid cell by hybridisation of a common myeloid progenitor cell that displays at least one of the following CD antigens CD16, CD15 or CD14, a B lymphoid cell and a T lymphoid cell.

In one embodiment, said cell derived from a common myeloid progenitor cell is a monocyte. As such, the invention provides a method of producing a hybrid cell by hybridisation of a monocyte and two B lymphoid cells or two T lymphoid cells. The invention also provides a method of producing a hybrid cell by hybridisation of a monocyte, a B lymphoid cell and a T lymphoid cell.

In another embodiment, said cell derived from a common myeloid progenitor cell is a primary myelomonocytic progenitor. As such, the invention provides a method of producing a hybrid cell by hybridisation of a primary myelomonocytic progenitor and two B lymphoid cells or two T lymphoid cells. The invention also provides a method of producing a hybrid cell by hybridisation of a primary myelomonocytic progenitor, a B lymphoid cell and a T lymphoid cell.

In one embodiment, said cell derived from a common myeloid progenitor cell is an immortalised cell. As such, it is clear that the invention provides a method of producing a hybrid cell by hybridisation of an immortalised cell selected from a myelomonocytic progenitor, monocyte, macrophage, eosinophil, neutrophil, dendritic cell or basophil and two B lymphoid cells or two T lymphoid cells. The invention also provides a method of producing a hybrid cell by hybridisation of an immortalised cell selected from a myelomonocytic progenitor, monocyte, macrophage, eosinophil, neutrophil, dendritic cell or basophil, a B lymphoid cell and a T lymphoid cell.

In another embodiment, said cell derived from a common myeloid progenitor cell is derived from spleen, peripheral blood, umbilical cord blood or bone marrow. As such, it is clear that the invention provides a method of producing a hybrid cell by hybridisation of a common myeloid progenitor cell derived from spleen, peripheral blood, umbilical cord blood or bone marrow and two B lymphoid cells or two T lymphoid cells. The invention also provides a method of producing a hybrid cell by hybridisation of a common myeloid progenitor cell derived from spleen, peripheral blood, umbilical cord blood or bone marrow, a B lymphoid cell and a T lymphoid cell.

In another embodiment, said cell derived from B lymphoid lineage is a pre-B cell, an immature B cell, a naïve B cell, an activated B cell or an effector B cell. As such, it is clear that the invention provides a method of producing a hybrid cell by hybridisation of a common myeloid progenitor cell or a stem cell and two B lymphoid cells selected from a pre-B cell, an immature B cell, a naïve B cell, an activated B cell or an effector B cell. The invention also provides a method of producing a hybrid cell by hybridisation of a common myeloid progenitor cell or stem cell, a B lymphoid cell selected from a pre-B cell, an immature B cell, a naïve B cell, an activated B cell or an effector B cell and a T lymphoid cell.

In one embodiment, said effector B cell is an antigen-experienced B-cell or a plasma cell. As such, the invention provides a method of producing a hybrid cell by hybridisation of a common myeloid progenitor cell or stem cell and two B lymphoid cells selected from an antigen-experienced B-cell or a plasma cell. The invention also provides a method of producing a hybrid cell by hybridisation of a common myeloid progenitor cell or stem cell, an antigen-experienced B-cell or a plasma cell and a T lymphoid cell.

In one embodiment, said cell derived from B lymphoid lineage displays at least one of the following CD antigens CD19, CD20, CD72 or CD5. As such, the invention provides a method of producing a hybrid cell by hybridisation of a common myeloid progenitor cell or stem cell and two B lymphoid cells which display at least one of the following CD antigens CD19, CD20, CD72 or CD5. The invention also provides a method of producing a hybrid cell by hybridisation of a common myeloid progenitor cell or stem cell, a B lymphoid cell which displays at least one of the following CD antigens CD19, CD20, CD72 or CD5 and a T lymphoid cell.

In one embodiment, said cell derived from T lymphoid lineage is a pre-T cell, an immature T cell, a naïve T cell, an activated T cell or an effector T cell. As such, the invention provides a method of producing a hybrid cell by hybridisation of a common myeloid progenitor cell or stem cell, a B lymphoid cell and a T lymphoid cell selected from a pre-T cell, an immature T cell, a naïve T cell, an activated T cell or an effector T cell. The invention also provides a method of producing a hybrid cell by hybridisation of a common myeloid progenitor cell or stem cell and two T lymphoid cells selected from a pre-T cell, an immature T cell, a naïve T cell, an activated T cell or an effector T cell.

In one embodiment, said cell derived from T lymphoid lineage displays at least one of the following CD antigens CD3, CD4, CD5 or CD8. As such, the invention provides a method of producing a hybrid cell by hybridisation of a common myeloid progenitor cell or stem cell, a B lymphoid cell and a T lymphoid cell which displays at least one of the following CD antigens CD3, CD4, CD5 or CD8. The invention also provides a method of producing a hybrid cell by hybridisation of a common myeloid progenitor cell or stem cell and two T lymphoid cells selected from T cells that display at least one of the following CD antigens CD3, CD4, CD5 or CD8.

In one embodiment, said cell derived from B lymphoid lineage is an immortalised cell. As such, the invention provides a method of producing a hybrid cell by hybridisation of a common myeloid progenitor cell or stem cell and two B lymphoid cells, at least one of which can be an immortal cell. The invention also provides a method of producing a hybrid cell by hybridisation of a common myeloid progenitor cell or stem cell, an immortal B lymphoid cell and a T lymphoid cell.

In one embodiment, said cell derived from T lymphoid lineage is an immortalised cell. As such, the invention provides a method of producing a hybrid cell by hybridisation of a common myeloid progenitor cell or stem cell, a B lymphoid cell and an immortal T lymphoid cell.

In one embodiment, said cell derived from B lymphoid lineage is derived from lymphoid tissue. As such, the invention provides a method of producing a hybrid cell by hybridisation of a common myeloid progenitor cell or stem cell and two B lymphoid cells derived from lymphoid tissue. The invention also provides a method of producing a hybrid cell by hybridisation of a common myeloid progenitor cell or stem cell, B lymphoid cell derived from lymphoid tissue and a T lymphoid cell.

In one embodiment, said cell derived from T lymphoid lineage is derived from lymphoid tissue. As such, invention provides a method of producing a hybrid cell by hybridisation of a common myeloid progenitor cell or stem cell, B lymphoid cell tissue and a T lymphoid cell derived from lymphoid tissue.

Where the B or T lymphoid cells included in the method of producing a hybrid cell of the invention are derived from lymphoid tissue said lymphoid tissue is preferably selected from peripheral blood, cord blood, spleen, bone marrow, thymus, tonsils, adenoids, and regional lymph node.

In one embodiment, at least one of the cells included in the method of producing a hybrid cell of the invention is a human cell. It will also be clear that in one embodiment, the method of producing a hybrid cell of the invention may include at least one mouse cell.

In one embodiment, said cell derived from a common myeloid progenitor cell is a K562 cell. As such, it will be clear that the invention provides a method of producing a hybrid cell by hybridisation of a K562 cell and two B lymphoid cells. The invention also provides a method of producing a hybrid cell by hybridisation of a K562 cell, an immortal B lymphoid cell and a T lymphoid cell.

In one embodiment, said second cell or said third cell is a WIL2-NS cell or a MOLT4 cell. As such, it will be clear that the invention provides a method of producing a hybrid cell by hybridisation of a common myeloid progenitor cell or stem cell, a WIL2-NS cell and a T lymphoid cell. The invention also provides a method of producing a hybrid cell by hybridisation of a common myeloid progenitor cell or stem cell, a B lymphoid cell and a MOLT4 cell.

In one embodiment, said first cell is a K562 cell, said second cell is a WIL2-NS cell and said third cell is a MOLT4 cell.

In another embodiment of the method of the invention, said first cell is a K562 cell, said second cell is a primary B cell and said third cell is a primary T cell.

In another embodiment of the method of the invention, said first cell is a primary human monocyte, said second cell is a WIL2-NS cell and said third cell is a primary T cell.

In another embodiment of the method of the invention, said first cell is a primary human myelomonocytic progenitor, said second cell is a WIL2-NS cell and said third cell is a primary human T cell.

In another embodiment of the method of the invention, said first cell is a K562 cell, said second cell is a WIL2-NS cell and said third cell is a primary T cell.

In another embodiment of the method of the invention, said first cell is a primary monocyte, said second cell is a WIL2-NS cell and said third cell is a WIL2-NS cell.

In another embodiment of the method of the invention, said first cell is a primary mouse monocyte, said second cell is an SP2 cell and said third cell is a primary mouse T cell.

In another embodiment of the method of the invention, said first cell is a primary mouse monocyte, said second cell is an SP2 cell and said third cell is a SP2 cell.

In another embodiment of the method of the invention, said first cell is a primary human or mouse monocyte, said second cell is a WIL2-NS cell and said third cell is an SP2 cell.

Definitions

In the context of the present invention, the words "comprise", "comprising" and the like are to be construed in their inclusive, as opposed to their exclusive, sense, that is in the sense of "including, but not limited to".

Hybrid Cell

A hybrid cell is a cell that comprises components from more than one genome (other than zygotes and their derivatives). It is a cell that is constructed from a somatic cell hybridization (or a whole cell hybridization) of, for example, two or more biological cells (parent cells). The parent cells can be obtained from either the same lineage (or species) or a different lineage (or species). The hybrid cell created from the same lineage and species is dubbed auto-hybrid, whereas that of different lineages is dubbed a hetero-hybrid.

Chimeric Cell

A chimeric cell is an artificially produced hybrid cell with a genome originating from two or more different species.

Cross-lineage Hybrid Cell

A cross-lineage hybrid cell is an artificially produced hybrid cell with a genome originating from two or more cells derived from different cell lineages. Hematopoietic cells are divided into two main lineages: lymphoid (T cells, B cells and NK cells) and myeloid (monocytes and macrophages, neutrophils, basophils and eosinophils, erythrocytes, megakaryocytes/platelets, dendritic cells).

Tri-Hybrid Cell

A tri-hybrid cell is an artificially produced hybrid cell with a genome originating from three cells.

Stable

When referring to a cell, the term "stable" denotes a cell's capacity to demonstrate consistency of a given growth or productivity parameter, or consistency of the cell line's product characteristics with increasing generation number. When used in reference to a stable transfectant it denotes a cell line that expresses a trans-gene at a relatively constant level substantially indefinitely.

Somatic Cell Hybridisation

In the context of the present application the term "somatic cell hybridisation" refers to a process in which one single viable cell is created from two or more diploid (non-gamete) cells (parent cells) in such a way that the plasma-membranes of the cells are induced to be in good contact, a reversible breakdown of the plasma membranes of the parent cells at the point of contact is simultaneously induced and the entities or organelles of each parent cell are combined within the envelope of the newly formed single cell. The newly formed single cell is dubbed a hybridised cell or hybrid cell.

Stem Cell

The term "stem cell" refers to an unspecialised cell with a capacity to divide by mitosis and to develop into a range of different cell types. Stems cells may include embryonic stem cells, "adult" stem cells derived from umbilical cord or stem cells derived from adults. Stem cells include cells that have an unlimited capacity to differentiate into all cell types, ie totipotent cells. Stem cells may also include cells that are limited in their capacity to differentiate into specialised cells, for example pluripotent, multipotent, oligopotent or unipotent stem cells.

Immortalised Cell

The term "immortalised cell" refers to a cell which has the capacity for indefinite growth. It will be clear that an immortalised cell may be derived from an in vivo malignancy or embryo. Alternatively, an immortalised cell may be derived by performing an action on a cell that induces a capacity for indefinite growth. These actions may include, for example, in vitro transformation processes eg the introduction of viral genes such as Epstein-Barr virus (EBV), Simian virus 40 (SV40) T antigen, adenovirus E1A and E1B, and human papillomavirus (HPV) E6 and E7. Alternatively, an immortalised cell may be derived from a cell via expression of the telomerase reverse transcriptase protein (TERT) or other means. Immortalised cells may also be derived from cells in which oncogene expression has been modified. Immortalised cells may be derived from any action that induces a capacity for indefinite growth including, but not limited to, UV exposure or spontaneous transformation in which the mechanism for immortality is not known.

Myeloma Cell

The term "myeloma cell" refers to a malignancy of a plasma cell.

Hybridoma

The term "hybridoma" refers to a cell which is produced by the hybridisation of a myeloma cell and a B-cell derived from the spleen of an immunised animal. Hybridomas are immortalised cells with a capacity to produce monoclonal antibodies.

Uncommitted Progenitor Cell

The term "uncommitted progenitor cell" refers to an early descendant of a stem cell that can only differentiate into limited kinds of cells without being committed to any specific lineage, but it cannot renew itself any more.

Common Myeloid Progenitor Cell

A common myeloid progenitor cell is a progeny of a hematopoietic stem cell restricted to the myeloid lineage and capable of giving rise to either megakaryocyte/erythrocyte or granulocyte/macrophage progenitors but not lymphoid cells.

Common Lymphoid Progenitor

A common lymphoid progenitor is a progeny of the hematopoietic stem cells restricted to the lymphoid lineage and giving rise to B, T and natural killer cells but not myeloid cells.

B Lymphoid Lineage-derived Cell

A B lymphoid lineage-derived cell is any cell originating from a common lymphoid progenitor following its B lineage commitment to become any type of B cells.

T Lymphoid Lineage-derived Cell

A T lymphoid lineage-derived cell is any cell originating from a common lymphoid progenitor following its T lineage commitment to become any type of T cells.

Granulocyte-macrophage Progenitor Cell

A granulocyte-macrophage progenitor cell is a progenitor cell originating from a common myeloid progenitor cell and being committed to the granulocyte and monocyte lineages but not to megakaryocytic and erythroid lineages.

Megakaryocyte-erythroid Progenitor Cell

A megakaryocyte-erythroid progenitor cell is a progenitor cell originating from a common myeloid progenitor cell and being committed to the megakaryocytic and erythroid lineages but not to granulocyte and monocyte lineages.

Pre-B Cell

A pre-B-cell is a developing B cell at the stage when the heavy chain of membrane bound IgM is expressed with surrogate light chain.

Immature B Cell

An immature B cell refers to a developing B cell in bone marrow where at the recombination stage of antibody loci VJ are rearranged on L chains and VDJ are rearranged on H chains, IgM receptor expression is exhibited.

Naïve B Cell

A naïve B cell is a mature B cell that has differentiated and matured in bone marrow through random gene rearrangement of its surface immunoglobulin but not has yet encountered cognate antigen in the periphery.

Activated B Cell

A type of mature B cell that has encountered its cognate antigen in the periphery through antigen recognition via BCR resulting in a combination of clonal proliferation and terminal differentiation into plasma cells in a T-dependent or independent manner.

Effector B Cell

An effector B cell is often synonymous with an antibody secreting plasma cell, a type of short-lived B cell which secretes antibodies specific to a particular antigen as well as plethora of cytokines to engage other cells of immune systems Memory B-cell A memory B cells is a long-lived B cell formed from an activated B cell that is specific to the antigen encountered during the primary immune response and capable of quick response following a second exposure to the same antigen.

Plasma Cell

A plasma cell is a terminal post-mitotic, short-lived cell of immune system, which differentiates from a B cell upon stimulation by $CD4^+$ lymphocyte (Th cells) and secretes large amount of antibodies.

Pre-T Cell

A pre-T cell is a developing T cell at the stage when VbDbJb is complete and TCR beta chain is expressed in a double negative ($CD4^-CD8^-$) T cell ($CD3^+$).

Immature T Cell

An immature T cell is a developing T cell which has migrated from bone marrow to thymus but has not completed the re-arrangement of its TCR, or selection for its TCR binding capacity to self-peptides presented in the context of self-major histocompatibility complex (MHC) molecules or undergone commitment to the T killer or T helper lineages which correlate precisely with a cell's TCR specificity towards MHC class I or II molecules, respectively. Lineage commitment is marked phenotypically by the loss of expression of one of the co-receptor molecules, CD8 or CD4.

Naïve T Cell

A mature T cell that has differentiated in bone marrow, and successfully undergone the positive and negative processes of central selection in the thymus with re-agreement of its TCR and loss of one of the co-receptor molecules but not has yet encountered cognate antigen in the periphery.

Activated T Cell

An activated T cell is a T cell that, through engagement of both TCR and CD28 on the cell surface by the Major Histocompatibility complex peptide (peptide:MHC complex) and B7 family members on the antigen presenting cells respectively, is set on becoming antigen-specific effector T cell.

Effector T Cell

An effector T cell is a type of short-lived T lymphocyte that is able to respond immediately upon contact with cells bearing the appropriate peptide:MHC complex for the cell.

BRIEF DESCRIPTION OF THE FIGURES

FIG. 2a, approximately 18% of original CD71-enriched K562 cell population were positive for CD15 (R1 region) and FIG. 2b, re-analysis of CD15 positive K562 cells following two months in culture.

FIG. 9A shows that following 5 days culture, 18% of $CD19^+$ cells were IgM positive and 1% had detectable IgG on the cell surface and; FIG. 9B shows that following 10 days in culture the percentage of IgM positive lymphocytes reduced to 2% and the percentage of IgG positive cells increased to 15%.

Figure 10:
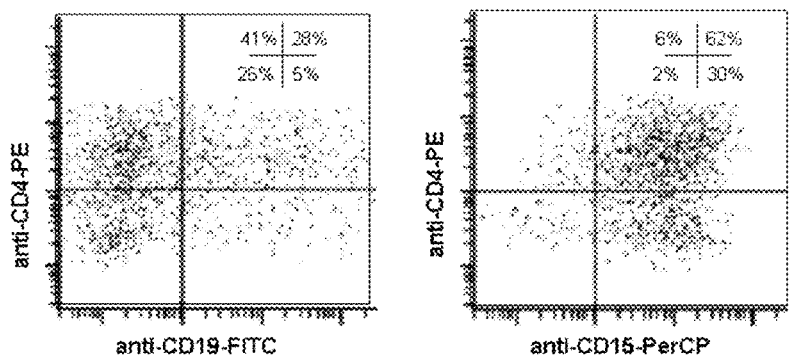

FIG. 10. FACS Profiles of CD4 and CD19 and CD4 and CD15 expression on KMW tri-hybrid cells with oncogene of myeloid and lymphoid sources.

Figure 11:
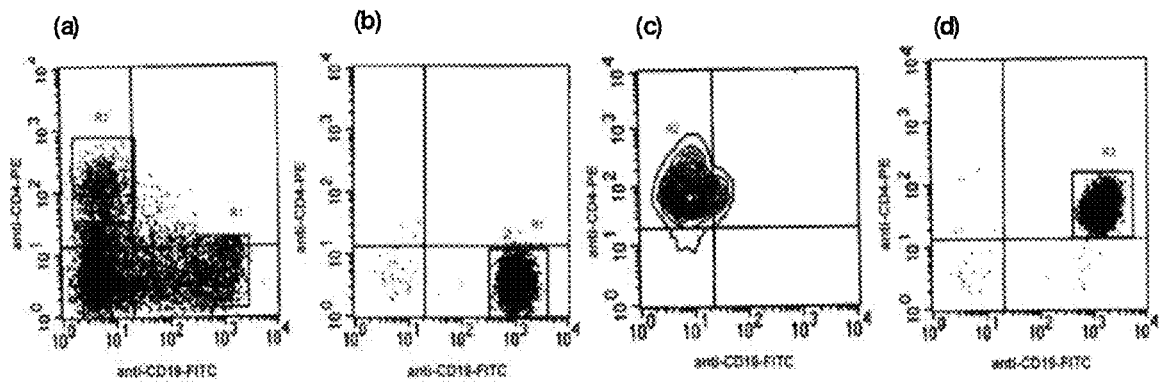

FIG. 11. Expression of CD4 and CD19 on primary mixed spleen lymphocytes, populations of sorted CD4 and CD19 and a resulting KBT tri-hybrid cell line: FIG.11a, expression of CD4 and CD19 on primary spleen lymphocytes; FIG.11b, purity profile of sorted CD19$^+$ cells (98.1%); FIG. 11c, purity profile of sorted CD4$^+$ cells (96.8%); FIG. 11d, co-expression of CD19 and CD4 on the tri-hybrid cells. More than 99% of tri-hybrid cell population co-express markers for both B and T cells.

Figure 12:
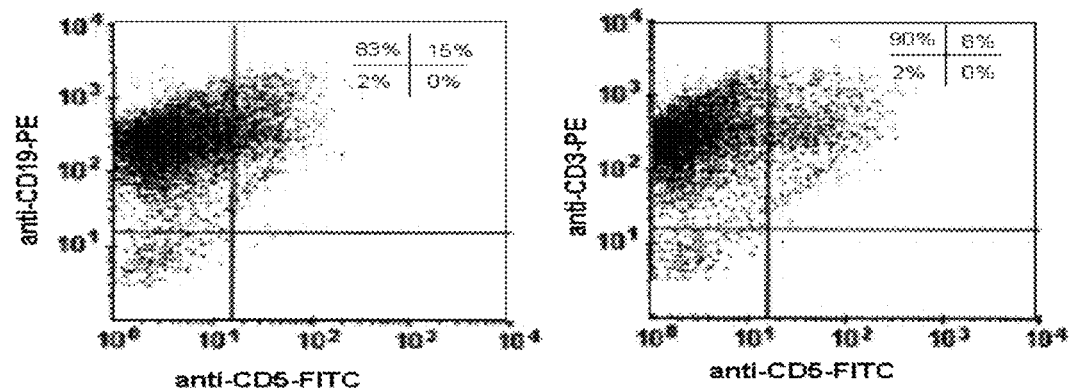

FIG. 12. Expressions of CD 19, CD3 and CD5 on a KBT tri-hybrid derived from immortal myeloid and 2 primary antigen-experienced lymphoid cells; (a) expression of CD19 and CD5 on KBT tri-hybrid cell surface, (b) expression of CD3 and CD5 on KBT tri-hybrid.

Figure 13:
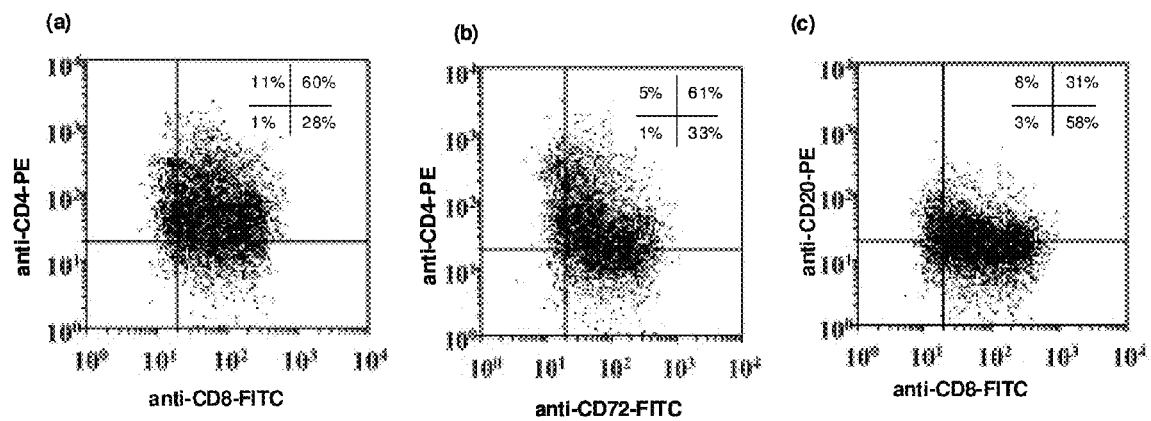

FIG. 13. Surface expressions of CD4, CD8, CD72 and CD20 on KBT tri-hybrid cells derived from immortal myeloid and 2 primary lymphoid cells derived from bone marrow and thymus: FIG. 13a, expression of CD4 and CD8, FIG. 13b, expression of CD4 and CD72, FIG. 13c, expression of CD20 and CD8.

Figure 14:
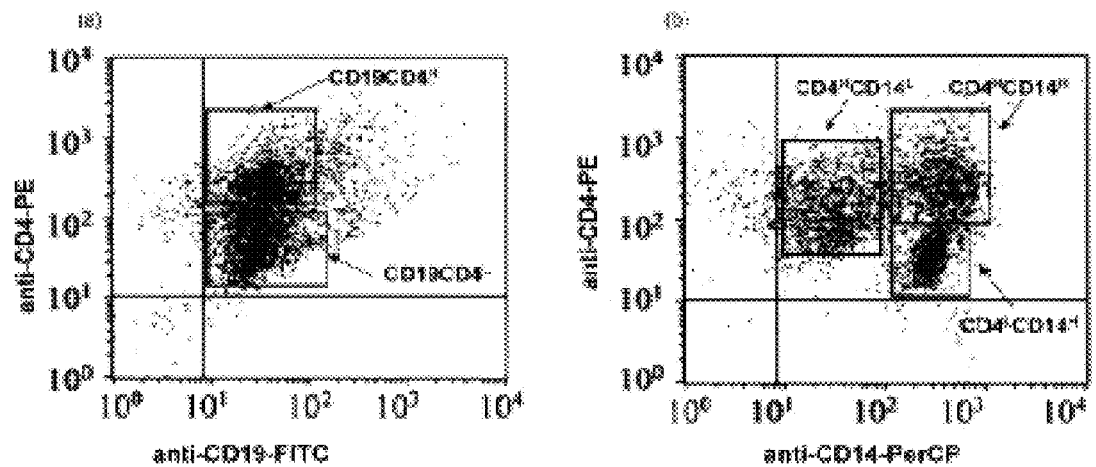

FIG. 14. FACS profiles of CD expressions on a WTM tri-hybrid line with oncogene of lymphoid source and CD4 and CD14 from primary cells: FIG. 14a, co-expression of CD19 and CD4 on the tri-hybrid cells showing one population CD19 cells with high level of CD4 expression (CD19 CD4$^H$) and another with low level of CD4 expression (CD19 CD4$^L$) and; FIG. 14b, co-expression of CD4 and CD14 on the same CD19 positive tri-hybrid population showing further heterogeneity of cell population based on high or low expression of CD14 (CD4$^H$CD14$^L$; CD4$^H$CD14$^H$; CD4$^L$CD14$^H$).

Figure 15:
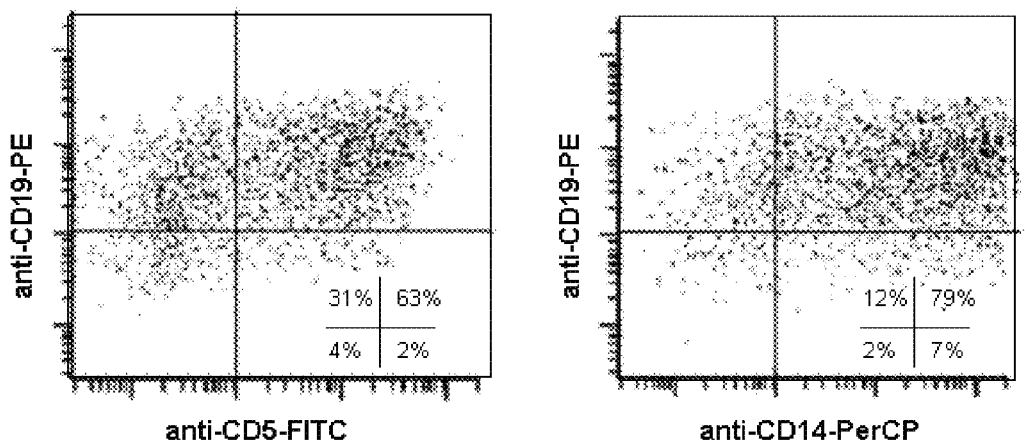

FIG. 15. Typical FACS Profiles of CD5 and CD19 and CD14 and CD19 expressions on the WTM tri-hybrid cells with oncogene of lymphoid source WIL2-NS, CD5 derived from antigen-experienced T cells and CD14 derived from primary monocyte cells.

Figure 16:
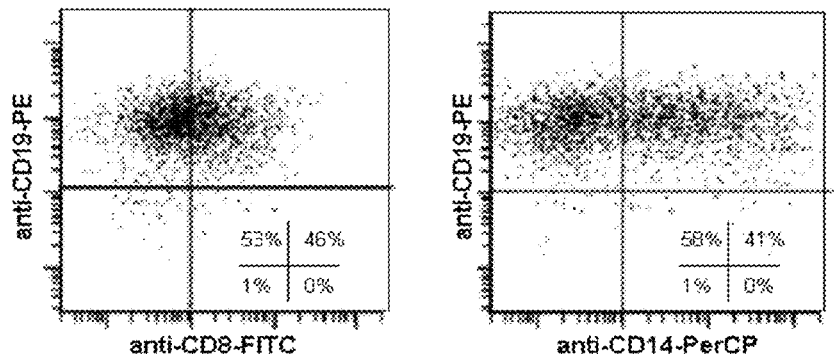

FIG. 16. FACS Profiles of CD8 and CD19 and CD14 and CD19 expressions on WTM tri-hybrid cells with oncogene of lymphoid source WIL2NS, CD8 derived from cytotoxic T cell and CD14 derived from primary monocyte cells.

Figure 17:
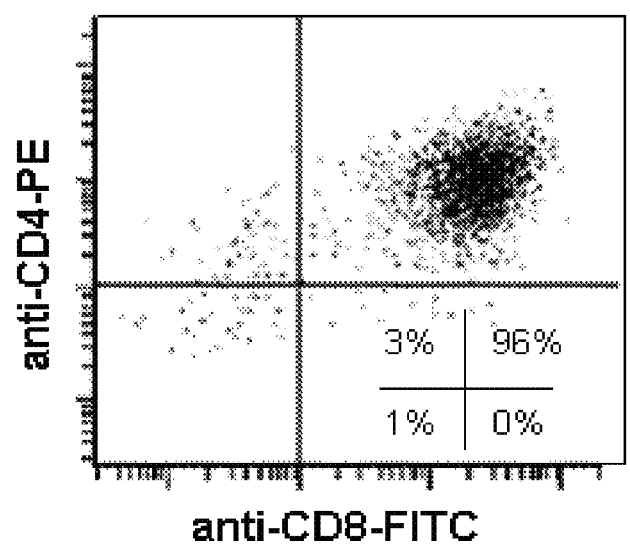

FIG. 17. A FACS Profile of CD4 and CD8 co-expression on the WTM tri-hybrids derived from double CD positive T cells.

Figure 18:
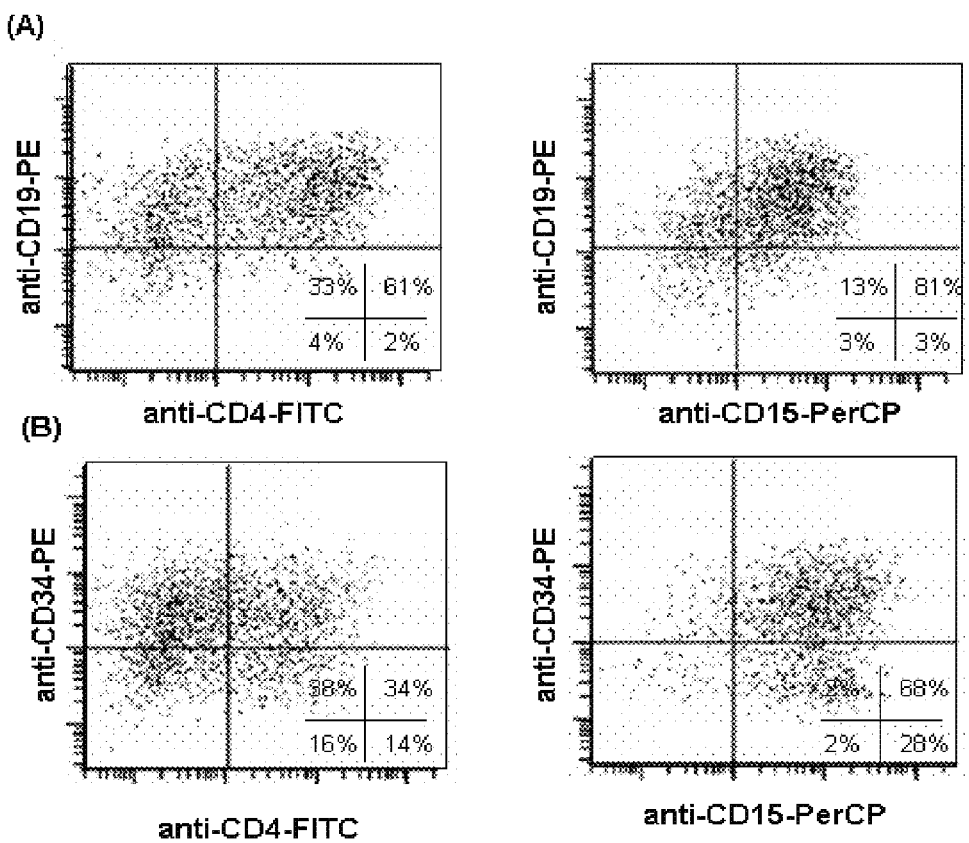

FIG. 18. CD expressions on the surface of WTM tri-hybrid cells originating from myelomonocytic progenitor cells: FIG. 18A, tri-colour staining with CD19, CD4 and CD15; and FIG. 18B, tri-colour staining with CD34 and CD15 derived from myelomonocytic progenitor and CD4 derived from effector T cells.

Figure 19:
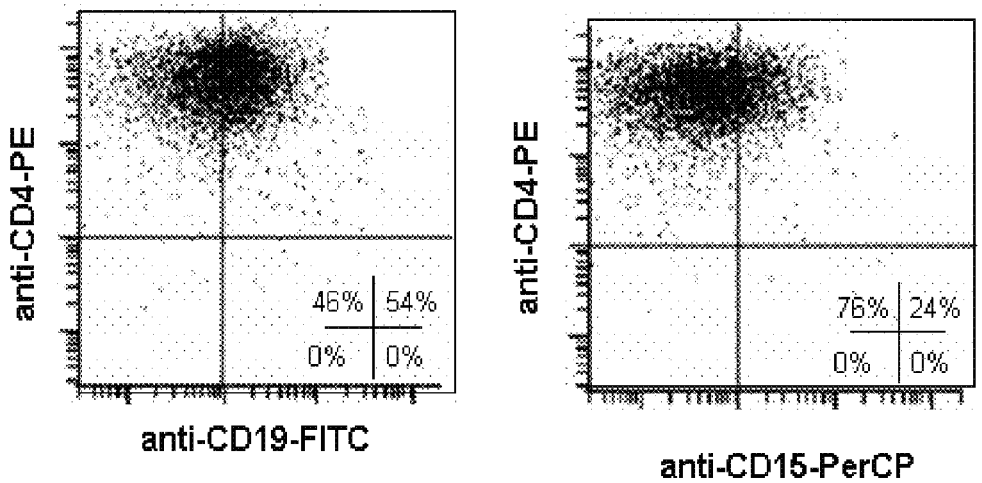

FIG. 19. The expression of lineage specific markers CD19 and CD4 and CD15 and CD4 of KWT tri-hybrid cells derived from CD4$^+$ effector T cells.

Figure 20:
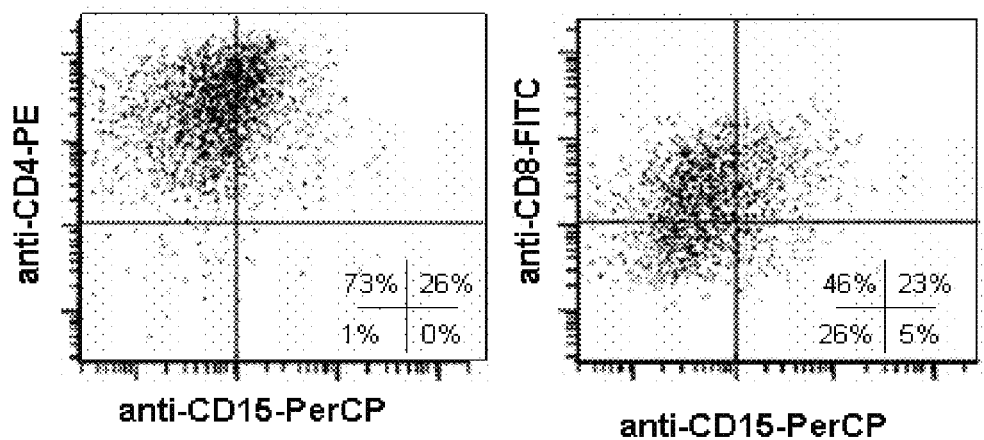

FIG. 20. Expressions of lineage specific markers CD16 and CD4 and CD15 and CD8 of KWT tri-hybrid cells derived from the double positive CD4$^+$CD8$^+$ T cells.

Figure 21:
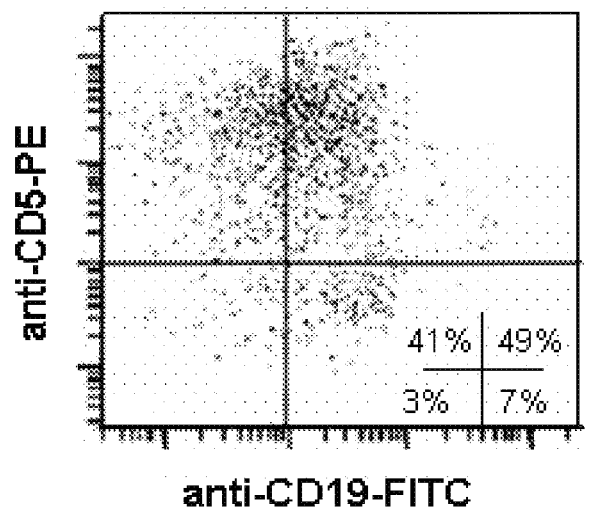

FIG. 21. An expression of lineage specific markers CD19 and CD5 of the KWT tri-hybrid cells derived from CD5$^+$ antigen-experienced T cells.

Figure 22:
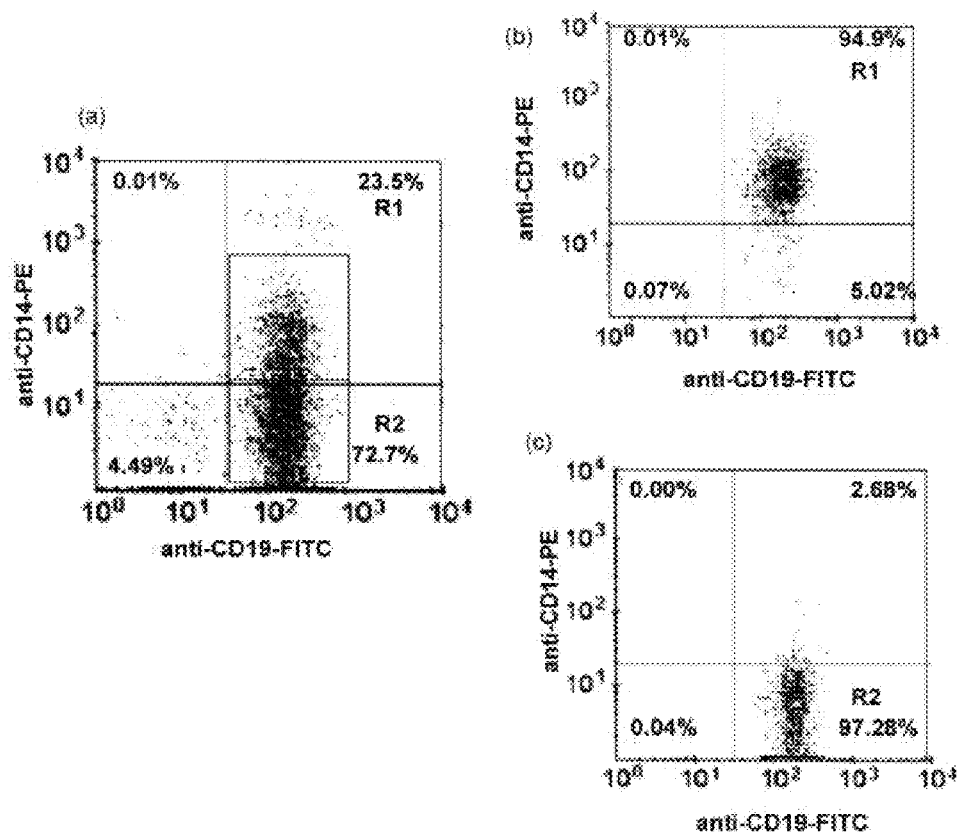

FIG. 22. Typical CD expression profile of WWM tri-hybrid cells originating from two cells each containing lymphoid oncogene and one primary monocytic cell: FIG. 22a co-expression of CD19 and CD14 on the tri-hybrid cells (R1 region) showing distinct population of CD19 positive cells which do not express CD14 (R2 region); FIG. 22a, CD14 expression on tri-hybrid cells derived from the sorted cells in R1 region and expanded in the culture for 2 months and; FIG. 22c, lack of surface CD14 on the tri-hybrid cells derived from the sorted population of R2 region 2 months later.

Figure 23:
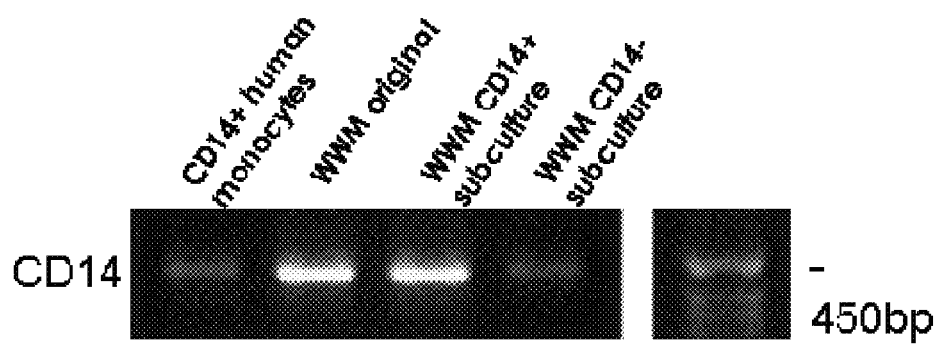

FIG. 23. Representative RT-PCR for CD14 obtained from different subpopulations of the WWM tri-hybrid cells.

Figure 24:
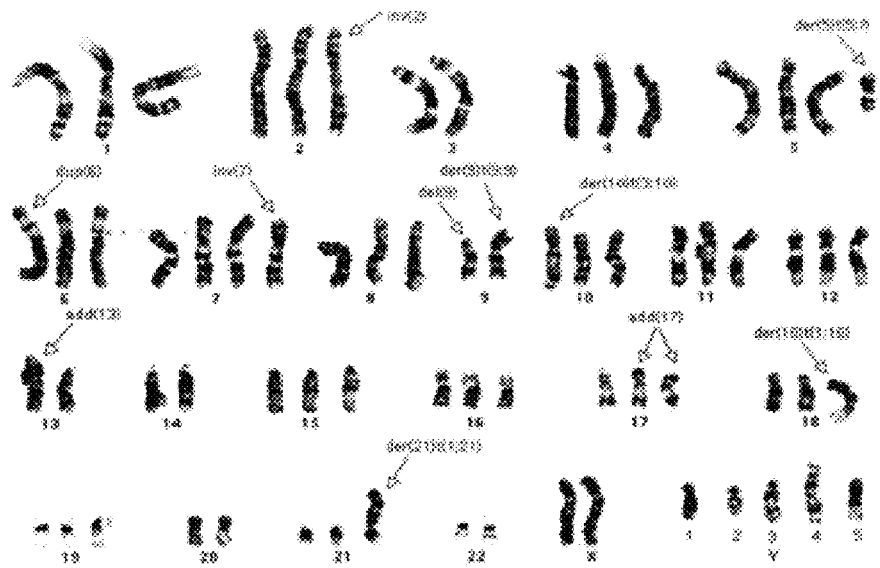

FIG. 24. A karyotyping of a single clone of K562 cells. The results indicated that K562 cell line was triploid, having a modal number of 69 chromosomes. The following chromosomal abnormalities were detected: missing one X chromosome; paracentric inversion of the long arm of chromosome 2, involving bands q33 and q35; missing chromosome 3, an additional derivative chromosome 5 with additional chromosome material of unknown origin replacing the segment from q11.2; a duplication of a segment of the short arm of chromosome 6 between bands p21.2 and p23; an additional chromosome 7 with a paracentric inversion of the short arm of chromosome 7 involving bands p13 and p22; missing one chromosome 9; a terminal deletion of the short arm of chromosome 9 from band p13; a derivative chromosome 9 resulting from a translocation involving segments from two chromosome 9's; a derivative of chromosome 10 resulting from a translocation involving segments from chromosomes 3 and 10; missing chromosome 13; additional chromosome material of unknown origin on the short arm of one chromosome 13; missing chromosome 14; additional material of unknown origin replacing the segment from p13 on two chromosome 17s; a derivative chromosome 18 resulting from a translocation involving segments from chromosomes 1 and 18; a missing one chromosome 20; a derivative chromosome 21 resulting from translocation involving segments of chromosomes 1 and 21; missing one chromosome 22; five additional different marker chromosomes.

Figure 25:
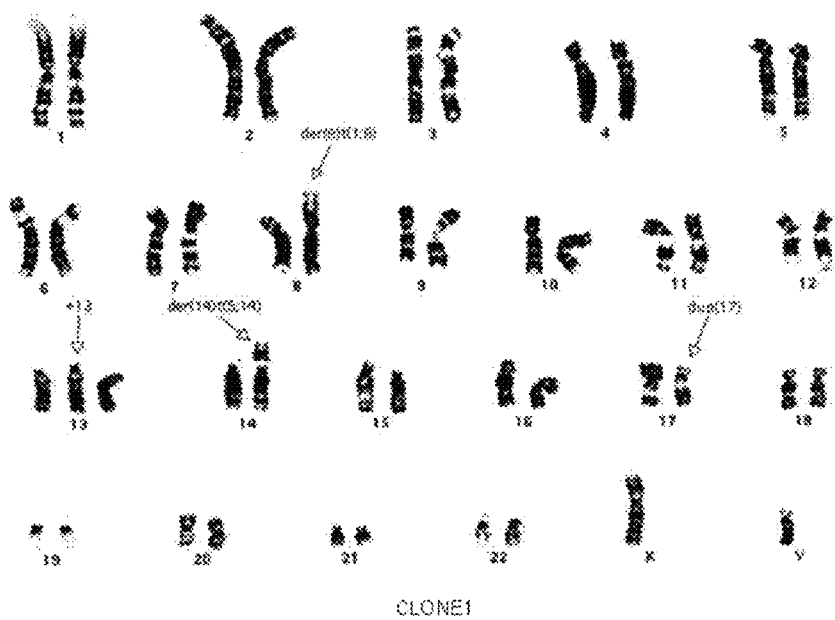

FIG. 25. A karyotyping of one of the five clones of WIL2NS cell line. In this clone (CLONE 1), the following abnormalities were detected; a derivative chromosome 8 resulting from a translocation involving segments from chromosomes 1 and 8; an extra homologue of chromosome 13; a derivative of chromosome 14 resulting from translocation involving segments from chromosomes 5 and 14; a duplication of chromosome 17 of the segment from q22-q23.

Figure 26:
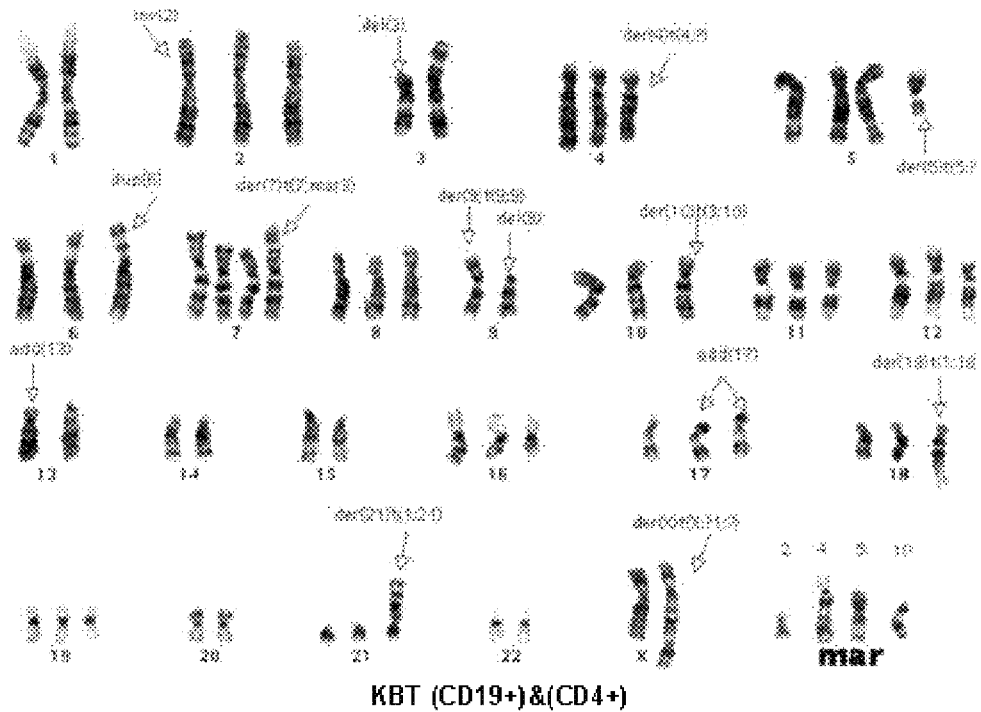

FIG. 26. A karyotyping of KBT-1 (CD19$^+$)&(CD4$^+$) tri-hybrid line, showings a single cell clone that is near triploid. The chromosome count varied from 65-66 due to random loss but had a modal number of chromosomes of 66. The following chromosome abnormalities were detected: a derivative X formed from a complex translocation involving the short arm of the X chromosome and possibly 2 other unidentified chromosomes; missing one X chromosome; paracentric inversion in the long arm of chromosome 2 involving bands q33 and q35; missing chromosome 3; deletion of chromosome 3p; a derivative chromosome 4 involving segments of chromosome 4 and another unidentified chromosome; an additional derivative chromosome 5 with additional chromosome material of unknown origin replacing the segment from q11.2; a duplication of a segment of the short arm of chromosome 6 between bands p21.2 and p23; an additional derivative chromosome 7 involving the long arm of chromosome 7 and the long arm of marker 3; missing one chromosome 13; additional chromosome material of unknown origin on the short arm of one chromosome 13; missing one chromosome 14; missing one chromosome 15; additional material of unknown origin replaces the segment from p13 on two chromosome 17s; a derivative chromosome 18 resulting from a translocation involving segments from chromosome 1 and 18; missing one chromosome 20; a derivative chromosome 21 resulting from a translocation involving segments of chromosome 1 and 21; missing chromosome 22; four additional different marker chromosomes.

Figure 27:
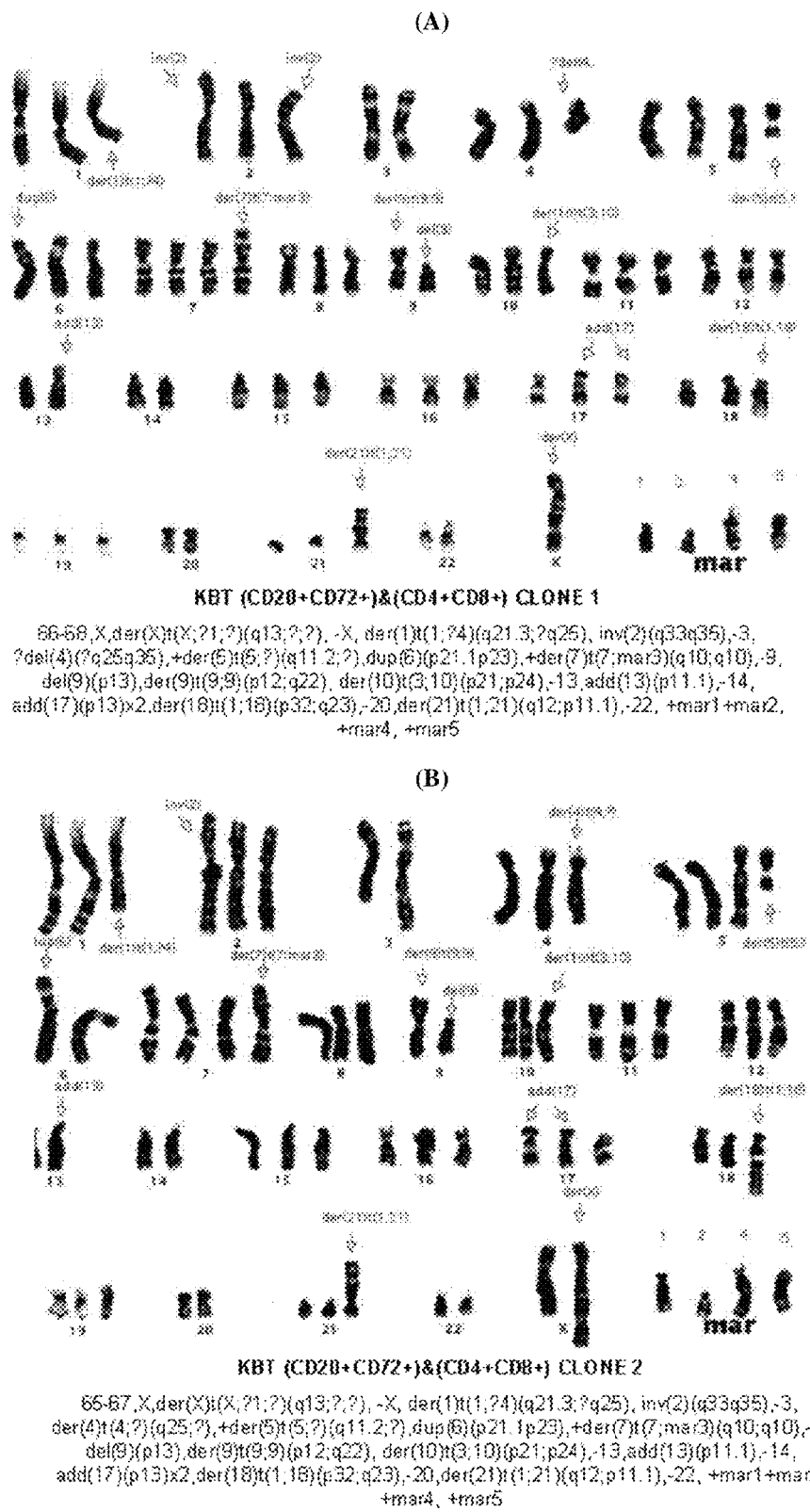
Figure 27:
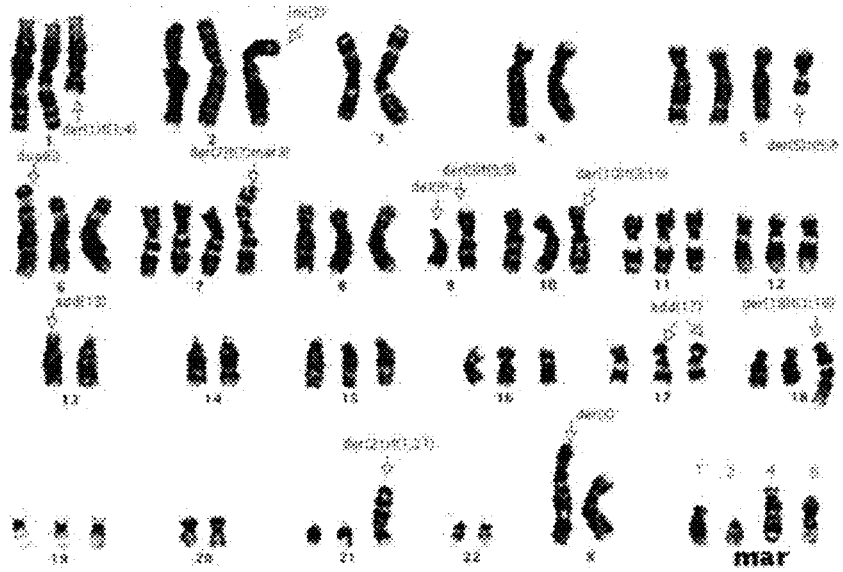
Figure 27:
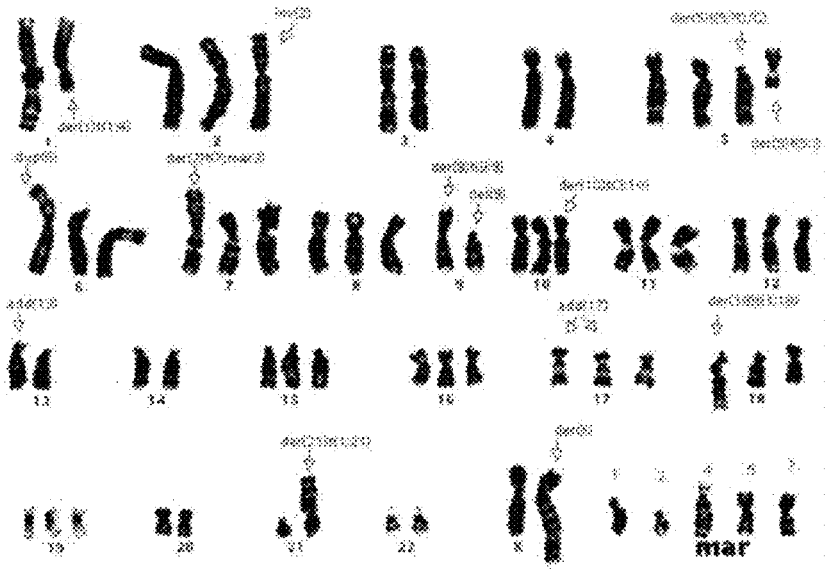

FIG. 27. Karyotype of KBT (K562&CD20$^+$CD72$^+$&CD4$^+$ CD8$^+$cells) cross-lineage tri-hybrid (or KBT-2 cross-lineage), showing four clones that are near triploid: FIG. 27A, CLONE 1 has a modal number of chromosomes of 67 and following chromosome abnormalities: a derivative X formed from a complex translocation involving the short arm of the X chromosome and possibly two other unidentified chromosomes; missing one X chromosome; a derivative chromosome 1 involving segments from chromosome 1 and most likely chromosome 4; paracentric inversion in the long arm of chromosome 2, involving bands q33 and q35; missing one chromosome 3; most likely a deleted chromosome 4 possibly be a small derivative chromosome 4; an additional derivative chromosome 5 with additional chromosome material of unknown origin replacing the segment from 11.2; a duplication of a segment of the short arm of chromosome 6 between bands p21.2 and p23; an additional derivative chromosome 7 involving long arm of chromosome 7 and the long arm of marker 3; missing one chromosome 9; a terminal deletion of the short arm of chromosome 9 from band p13; a derivative chromosome 9 resulting from a translocation involving segments from two chromosome 9s; a derivative chromosome 10 resulting from a translocation involving segments from chromosomes 3 and 10; missing one chromosome 13; additional chromosome material of unknown origin on the short arm of one chromosome 13; missing one chromosome 14; additional material of unknown origin replaces the segment from p13 on two chromosome 17s; a derivative chromosome 18 resulting from a translocation involving segments from chromosome 1 and 18; missing one chromosome 20; a derivative chromosome 21 resulting from a translocation involving segments of chromosomes 1 and 21; missing one chromosome 22; four additional different marker chromosomes; FIG. 27B, CLONE 2 contains 65 to 67 chromosomes due to random loss (modal chromosome number is 67) and has similar chromosomal characteristics to CLONE 1 with exception that deleted chromosome 4 of CLONE 1 is substituted with definite derivative chromosome 4 involving segments of chromosome 4 and another unidentified chromosome; FIG. 27C, CLONE 3 is essentially the same as CLONE 1 but the derivative chromosome 1 is missing and there is a different derivative chromosome 4 derived from segments of chromosome 1 and 4. It contains 67 to 68 chromosomes due to random loss with modal number of 67; FIG. 27D, CLONE 4 is essentially the same as CLONE 1 but there is a chromosome 1 missing and a different derivative chromosome 1 resulting from a translocation involving segments of chromosome 1 and 4. There are only two normal chromosome 540 s and a derivative chromosome 5 which appears to be a satellited 5q.

Figure 28:
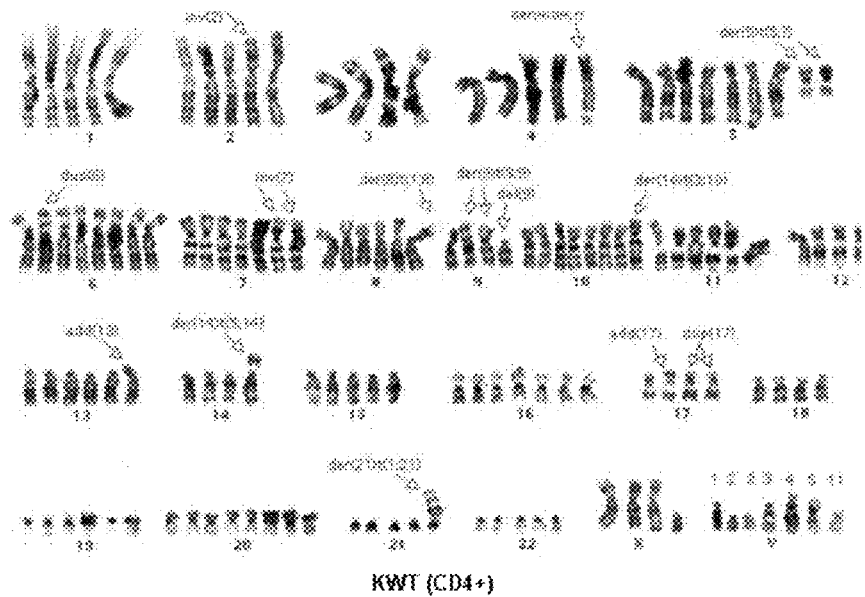

FIG. 28. A karyotyping of KWT-1 tri-hybrid line (KWT tri-hybrid derived immortal myeloid and B lymphoid cells and primary mature CD4$^+$ T helper cell), showing a single clone which is near-hexaploid with a modal number of 129 to 140 chromosomes and following chromosome abnormalities: missing two X chromosomes; missing one chromosome 1; missing one chromosome 2; paracentric inversion in the long arm of chromosome 2, involving bands q33 and q35; missing two chromosomes 3; missing one chromosome 4; a derivative chromosomes 4 with additional chromosome material of unknown origin replacing the segment from q35; one extra homologue of chromosome 5; two extra derivatives of chromosome 5 with additional chromosome material of unknown origin replacing the segment from q11.2; one extra homologue of chromosome 6; an additional chromosome 6 with a duplication of a segment of the short arm of chromosome 6 between bands p21.2 and p23; one extra homologue of chromosome 7; two chromosome 7s with a paracentric inversion of the short arm of chromosome 7 involving bands p13 and p22; a derivative chromosome 8 resulting from a translocation involving segments from chromosomes 1 and 8; missing two chromosomes 9s; a terminal deletion of the short arm of chromosome 9 from band p13; two derivative chromosome 9s resulting from a translocation involving segments from two chromosome 9s; a derivative of chromosome 10 resulting from a translocation involving segments from chromosomes 3 and 10; missing one chromosome 12; one chromosome 13 with additional chromosome material of unknown origin on the short arm of one chromosome 13; missing two chromosomes 14; a derivative of chromosome 14 resulting from a translocation involving segments from chromosomes 5 and 14; missing one chromosome 15; missing one chromosome 17; two chromosome 17s with additional material of unknown origin replacing the segment from p13 on two chromosome 17s; two chromosome 17s with a duplication in the segment from q22-q23; missing two chromosome 18s; an extra chromosome 20; a derivative chromosome 21 resulting from a translocation involving segments of chromosomes 1 and 21; missing one chromosome 22; seven additional marker chromosomes with two copies of marker chromosome 2.

Figure 29:
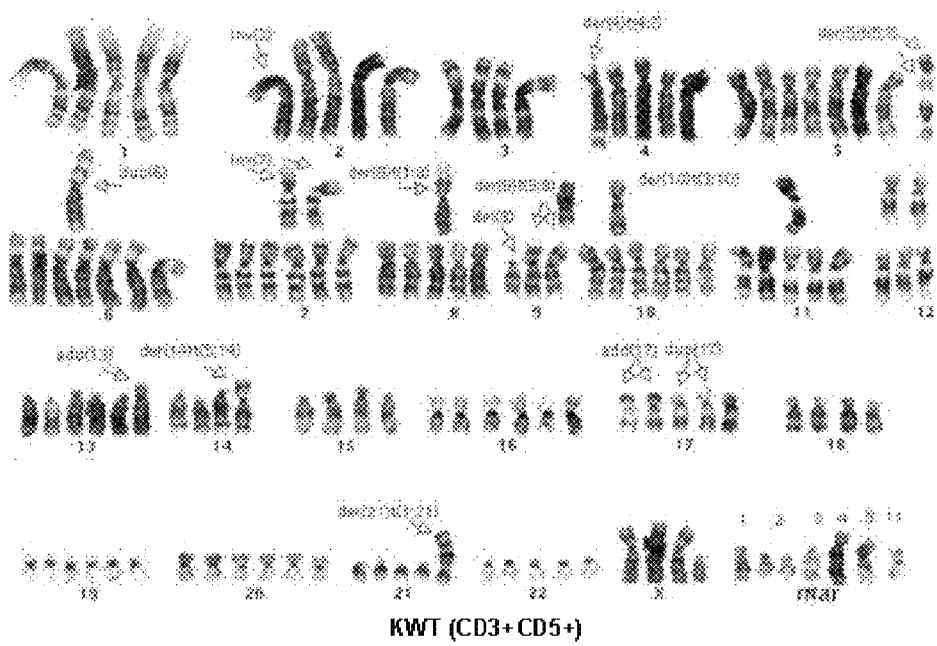

FIG. 29. A karyotyping of KWT-2 (KWT tri-hybrid line derived immortal myeloid and B lymphoid cells and primary memory CD3$^+$CD5$^+$ T cell), showing a single clone which is near-hexaploid with a modal number of 135 to 142 chromosomes and following chromosome abnormalities: missing two X chromosomes; missing one chromosome 1; missing one chromosome 2; paracentric inversion in the long arm of chromosome 2, involving bands q33 and q35; missing two chromosomes 3; missing one chromosome 4; a derivative chromosomes 4 with additional chromosome material of unknown origin replacing the segment from q35; one extra homologue of chromosome 5; two extra derivatives of chromosome 5 with additional chromosome material of unknown origin replacing the segment from q11.2; one extra homologue of chromosome 6; an additional chromosome 6 with a duplication of a segment of the short arm of chromosome 6 between bands p21.2 and p23; two chromosome 7s with a paracentric inversion of the short arm of chromosome 7 involving bands p13 and p22; a derivative chromosome 8 resulting from a translocation involving segments from chromosomes 1 and 8; missing two chromosomes 9s; a terminal deletion of the short arm of chromosome 9 from band p13; two derivative chromosome 9s resulting from a translocation involving segments from two chromosome 9s; a derivative of chromosome 10 resulting from a translocation involving segments from chromosomes 3 and 10; missing one chromosome 12; one chromosome 13 with additional chromosome material of unknown origin on the short arm of one chromosome 13; missing two chromosomes 14; a derivative of chromosome 14 resulting from a translocation involving segments from chromosomes 5 and 14; missing one chromosome 15; missing one chromosome 17; two chromosome 17s with additional material of unknown origin replacing the segment from p13 on two chromosome 17s; two chromosome 17s with a duplication in the segment from q22-q23; missing two chromosome 18s; an extra chromosome 20; a derivative chromosome 21 resulting from a translocation involving segments of chromosomes 1 and 21; missing one chromosome 22; eight additional marker chromosomes with two copies of marker chromosome 2.

Figure 30:
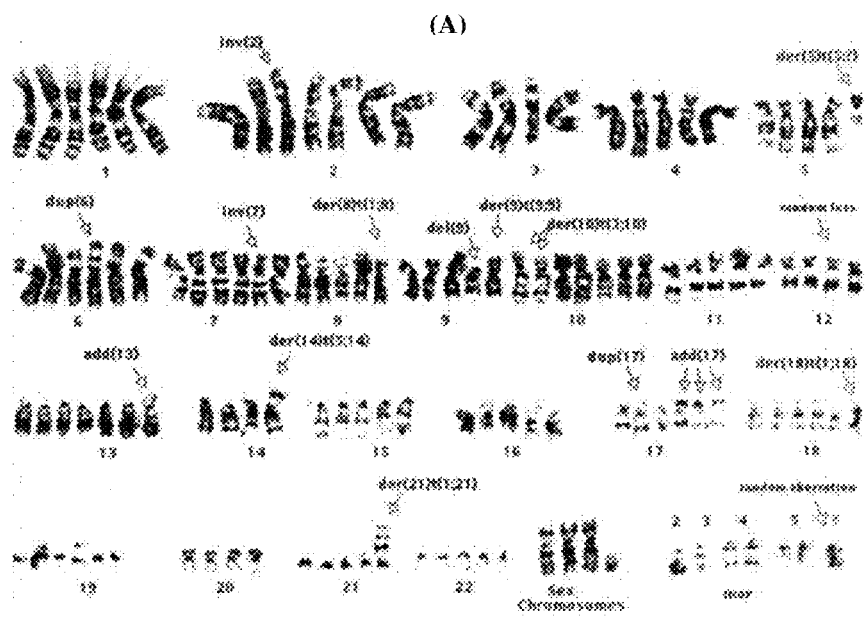
Figure 30:
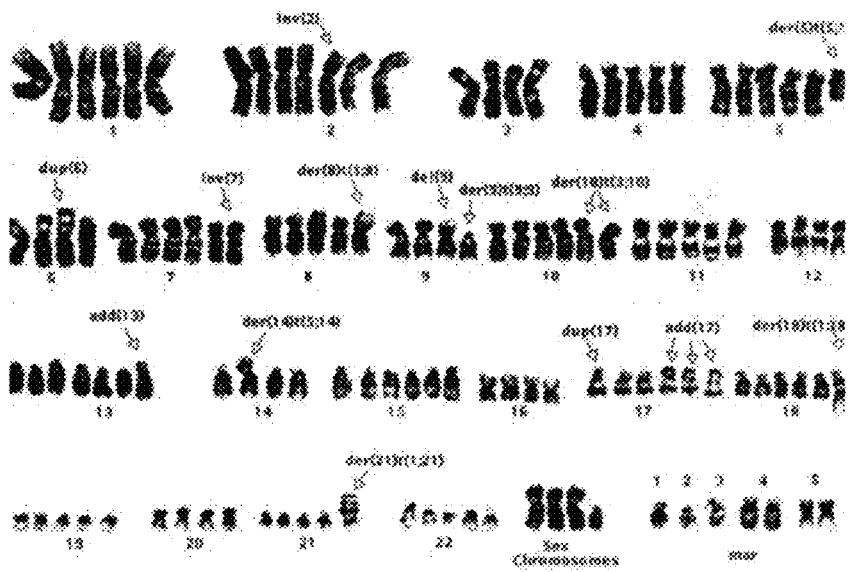
Figure 30:
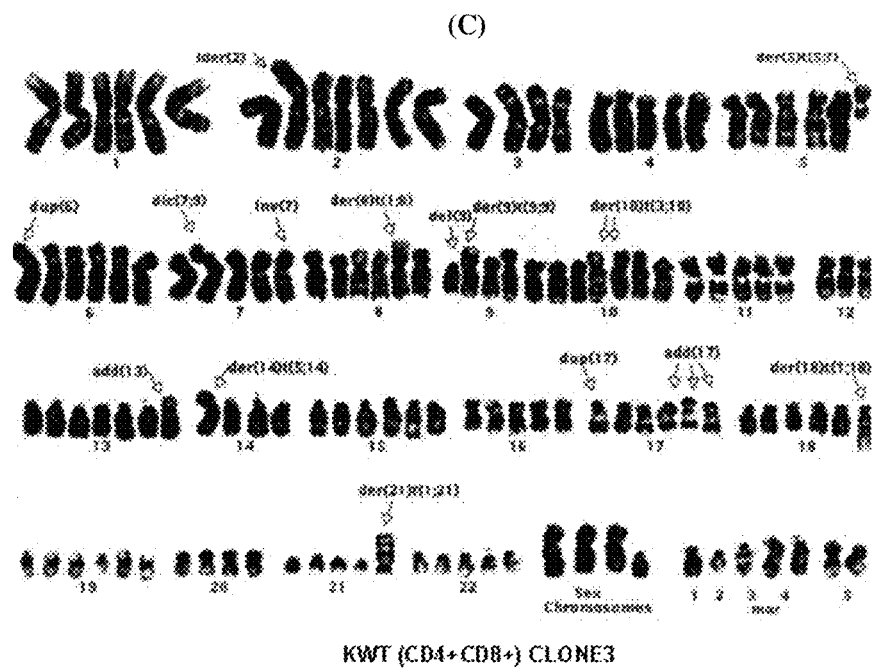

FIG. 30. Karyotypings of KWT-3 tri-hybrid line (KWT tri-hybrid derived immortal myeloid and B lymphoid cells and primary double positive CD4$^+$CD8$^+$ T cell), showing three clones which are hyperpentaploid with a modal chromosome number of 124 to 139. FIG 30A, CLONE 1 has following chromosome abnormalities: three X chromosomes and a single Y chromosome; an additional chromosome 1; two additional chromosome 2; paracentric inversion in the long arm of chromosome 2, involving bands q33 and q35; missing one chromosome 3; an additional derivative of chromosome 5 resulting from a translocation involving chromosome 5 and chromosome of unknown origin; an additional chromosome 6; a duplication of a segment of the short arm of chromosome 6 between bands p21.2 and p23; an additional paracentric inversion of the short arm of chromosome 7 involving bands p13 and p22; a derivative chromosome 8 resulting from a translocation involving segments from chromosomes 1 and 8; a terminal deletion of the short arm of chromosome 9 from band p13; a derivative chromosome 9 resulting from a translocation involving segments from two chromosome 9s; two additional chromosome 10; two derivative of chromosome 10s resulting from a translocation involving segments from chromosomes 3 and 10; two additional chromosome 13; an additional chromosome material of unknown origin on the short arm of one chromosome 13; missing one chromosome 14; a derivative of chromosome 14 resulting from a translocation involving segments from chromosomes 5 and 14; an additional material of unknown origin replacing the segment from p13 on three chromosome 17s; two chromosome a duplication of chromosome 17 in the segment from q22-q23; an additional chromosome 18; a derivative chromosome 18 resulting from a translocation involving segments from chromosome 1 and 18; an additional chromosome 19; missing one chromosome 20; a derivative chromosome 21 resulting from a translocation involving segments of chromosomes 1 and 21; five additional marker chromosomes with two copies of each marker chromosome 4 and 5. FIG. 30B CLONE 2 has similar chromosome abnormalities to that of CLONE1 except that it lost one chromosome 9. FIG. 30C, CLONE 3 contains the same chromosome abnormalities as CLONE 2 except for paracentric inversion in the long arm of chromosome 2 is replaced with an isoderivative chromosome 2 resulting from the formation an isochromosome involving a derivative chromosome 2 that was generated by a paracentric inversion in the long arm, involving bands q33 and q35.

Figure 31:
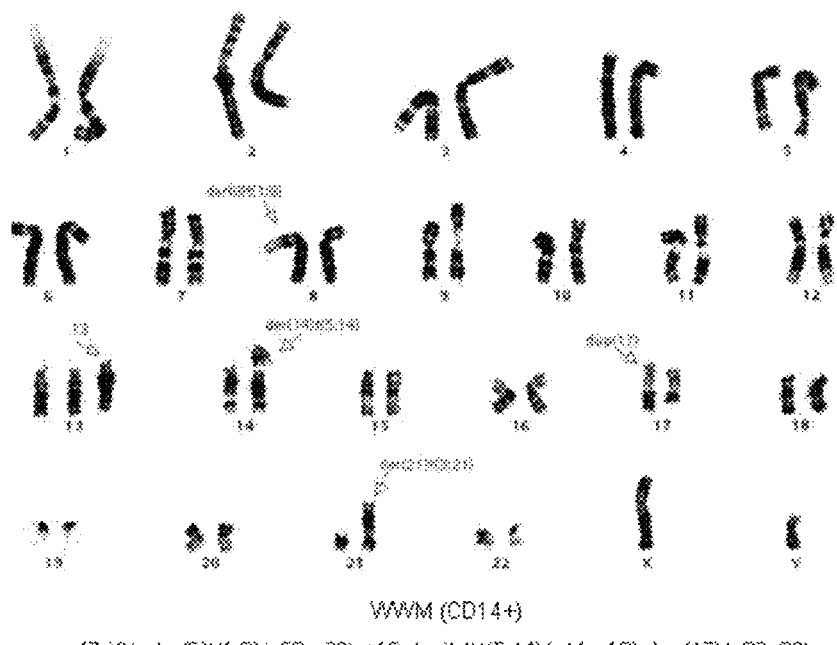
Figure 31:
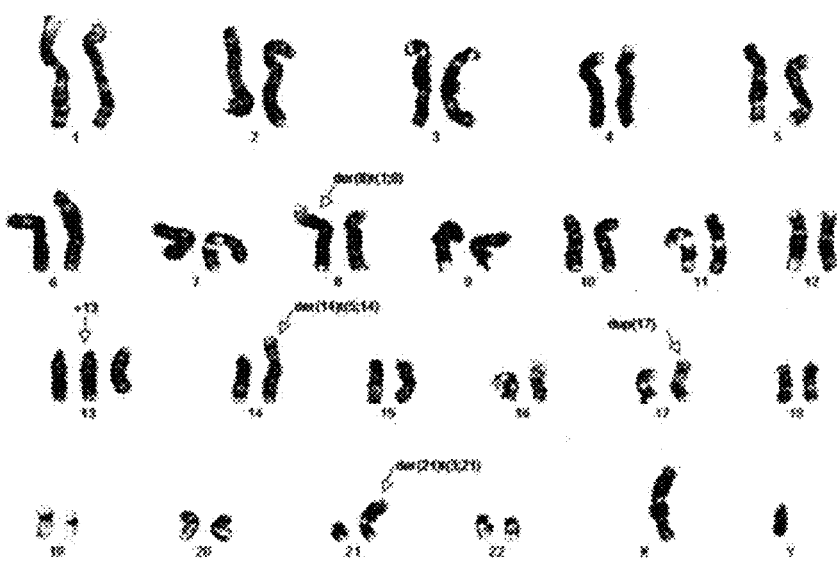

FIG. 31. Karyotypings of WWM tri-hybrids (FIG. 31A) and its CD14 enriched subline (FIG. 31B) showing a single dominant clone which increase its presence from 55% in the original WWM tri-hybrid to 95% in its CD14 enriched subline. Each has a modal number of 47 chromosomes and following chromosome abnormalities: a derivative of chromosome 8 resulting from a translocation involving segments from chromosomes 1 and 8; an extra homologue of chromosome 13; a derivative if chromosome 14 resulting from a translocation involving segments from chromosomes 5 and 14; a duplication of chromosome 17 of the segment from q22-23; a derivative chromosome 21 resulting from a translocation involving segments from chromosomes 3 and 21. The only difference between original WWM tri-hybrid and its CD 14$^+$ enriched subline is that these abnormalities are present in only 55% of cells in original WWM and 95% cells of CD14 enriched subline. The rest of the cells in WWM tri-hybrid range from near triploid (with random chromosome loss) to near tetraploid (with random chromosome loss).

Figure 32:
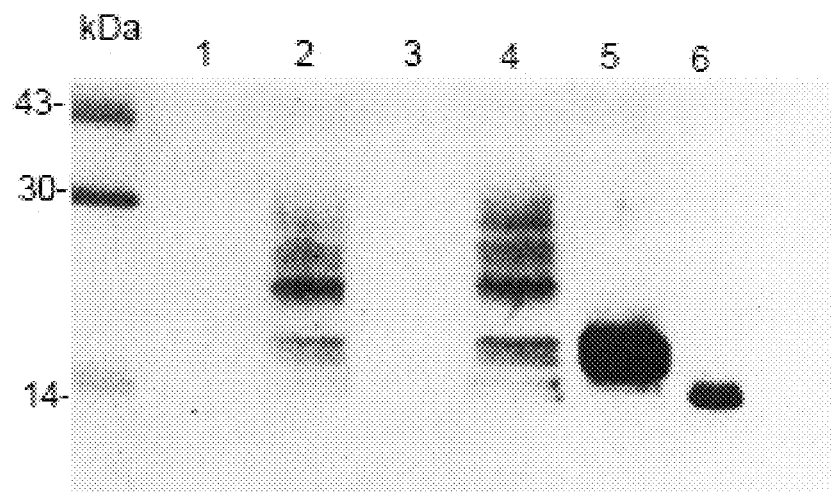

FIG. 32. Western blot of supernatants from ProGM cultures. Lanes 1 and 2 were loaded with supernatants of non-activated and activated 4 day human T lymphocyte cultures respectively. Lanes 4 and 5 contained supernatants of ProGM cultures grown in the absence or presence of tunicomycin, respectively. The supernatant of non-GM-CSF expressing cells was used in Lane 3. As reference, recombinant hGM-CSF (10 ng) derived from E. coli was used in Lane 6.

Figure 33:
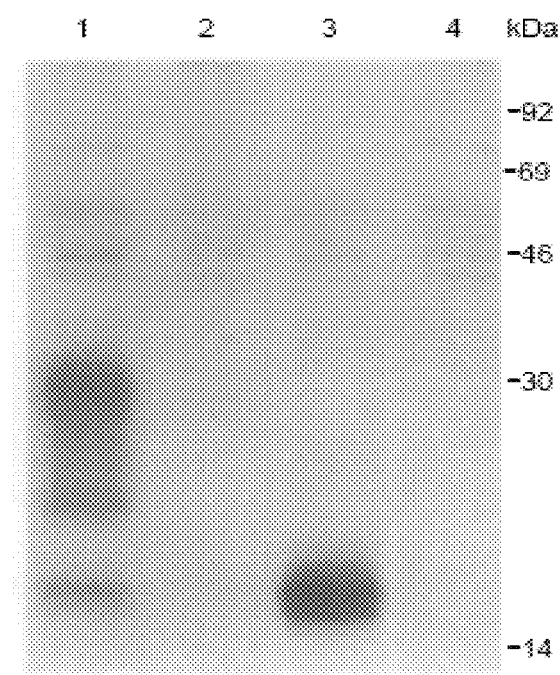

FIG. 33. Gel electrophoresis of human GM-CSF produced by the ProGM hybrid line. The cell supernatants of the ProGM hybrid line obtained from the samples which were cultured with (lanes 3 and 4) and without (lanes 1 and 2) tunicamycin were subjected to immunoprecipitation with rat anti-human GM-CSF antibody (lanes 1 and 3) and rat anti-mouse GM-CSF antibody (lanes 2 and 4). The proteins were visualized by silver staining.

Figure 34:
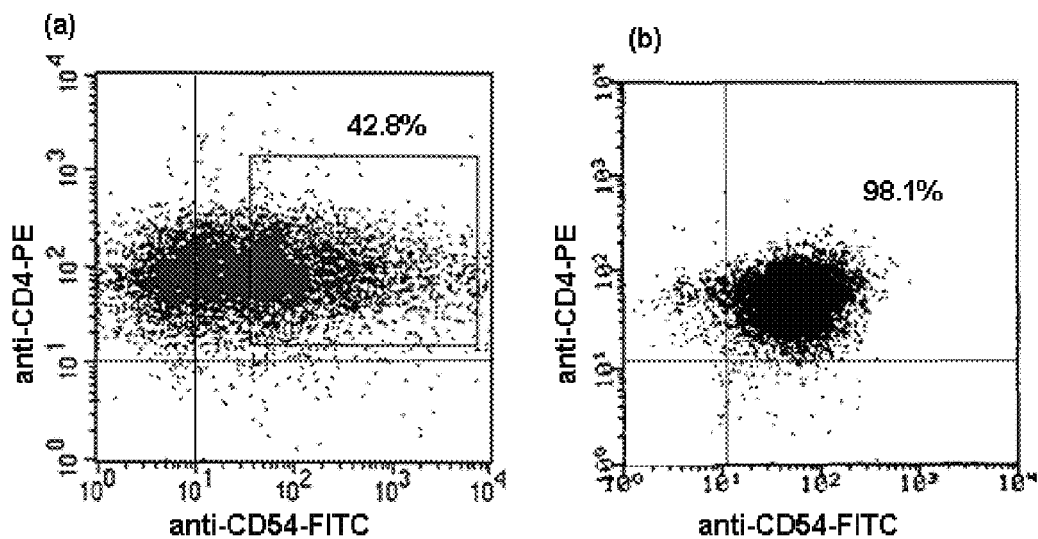

FIG. 34. Expression of CD4 and CD54 on the surface of ProCD54 cells line and its CD54 enriched sub-line, ProCD54EX: FIG. 34a, 100% of ProCD54 cells retained the expression of CD4. Approximately 72% of the cell population was also positive for CD54 ranging from low to high levels of expression. 42% of cell population with characteristics of CD4$^+$CD54$^+$ phenotype with mid to high levels of CD54 expression was gated and sorted out, and FIG. 34b, analysis of CD4 and CD54 expression of the surface of the sorted CD4$^+$CD54$^+$ sub-line of original ProCD54 shows that 98% of the cells are still positive for both markers after more than 6 months of culture.

Figure 35:
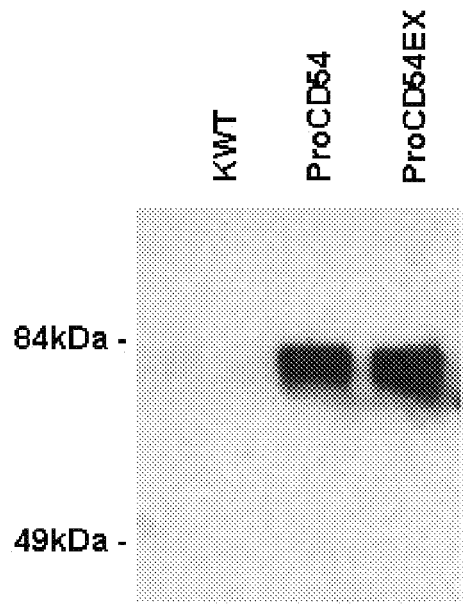

FIG. 35. Western blot of soluble human CD54 secreted by ProCD54 and ProCD54EX cells. The cells of the KWT tri-hybrid partner cell line were used as control. Both ProCD54 and ProCD54EX cells shed soluble form of CD54 of approximately 82 kDa.

Figure 36:
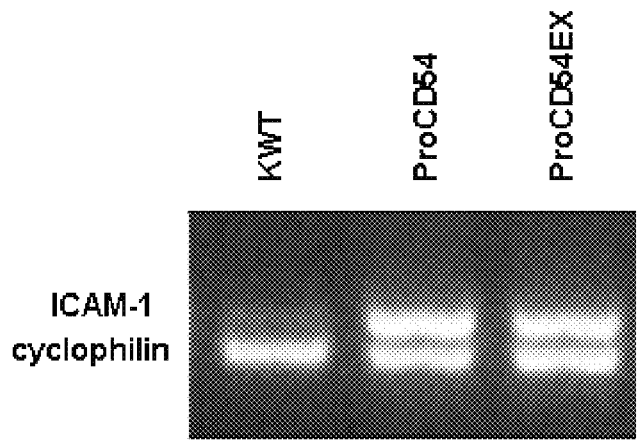

FIG. 36. An RT-PCR analysis of ICAM-1 gene expression in ProCD54 and ProCd54EX cells.

Figure 37:
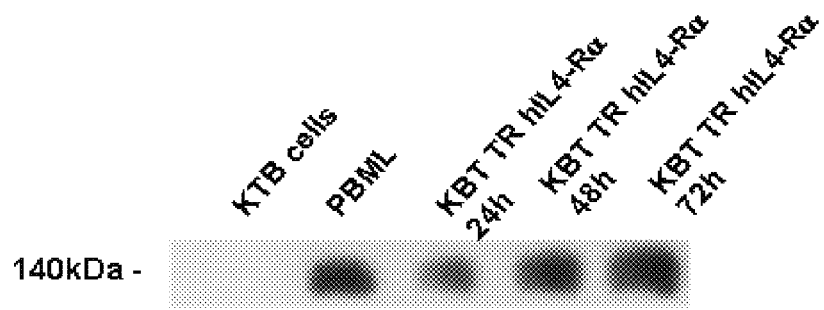

FIG. 37. Western blot analysis of cell extracts from a KBT tri-hybrid cell line transiently transfected with hIL4—Rα chain, 24, 48 and 72 hours after transfection. Human PBML stimulated with 100 ng/ml hIL4 and non-transfected KBT cells were used as a positive and negative control for hIL4—Rα chain, respectively.

Figure 38:
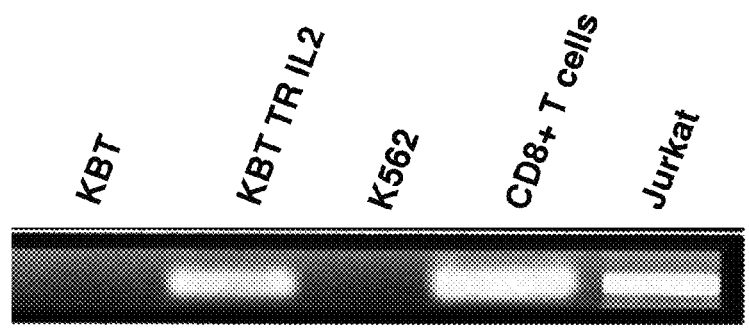

FIG. 38. A PCR output for the detection of hIL-2 mRNA in the KBT tri-hybrid cells transfected with hIL-2. The levels of expression are similar to those obtained from CD8$^+$ human T lymphocytes and Jurkat cells. Non-transfected KBT cells and K562 cells were used as negative controls.

Figure 39:
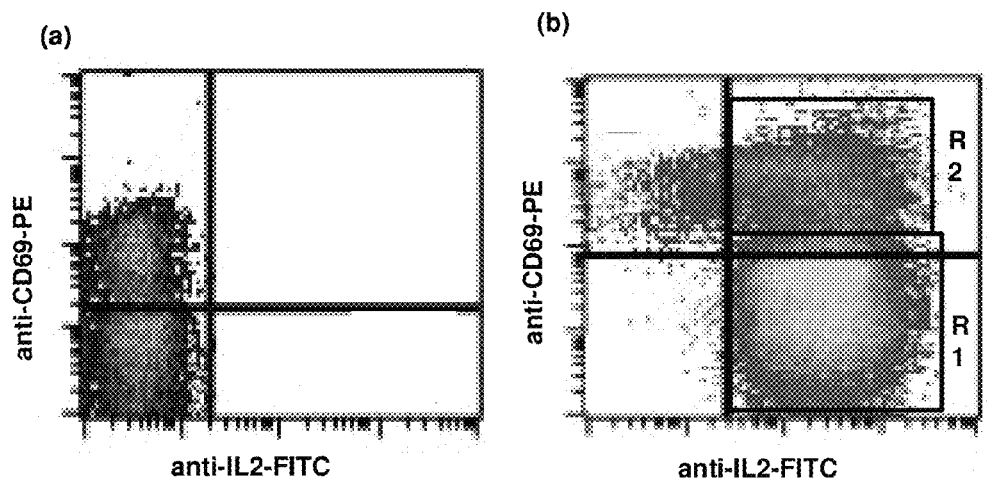

FIG. 39. The FACS analysis for intracellular hIL-2 in (FIG. 39a) original KBT tri-hybrid cells and (FIG. 39b) KBT TR-IL2 cells. Approximately 41% of the KBT cells were positive for CD69 activation molecule. 92% of the KBT TR-IL2 cells stained positive for intracellular hIL-2 (R1+R2). The hIL-2 negative cells were part of CD69 positive population, whereas CD69 negative cells were all positive for intracellular hIL2.

Figure 40:
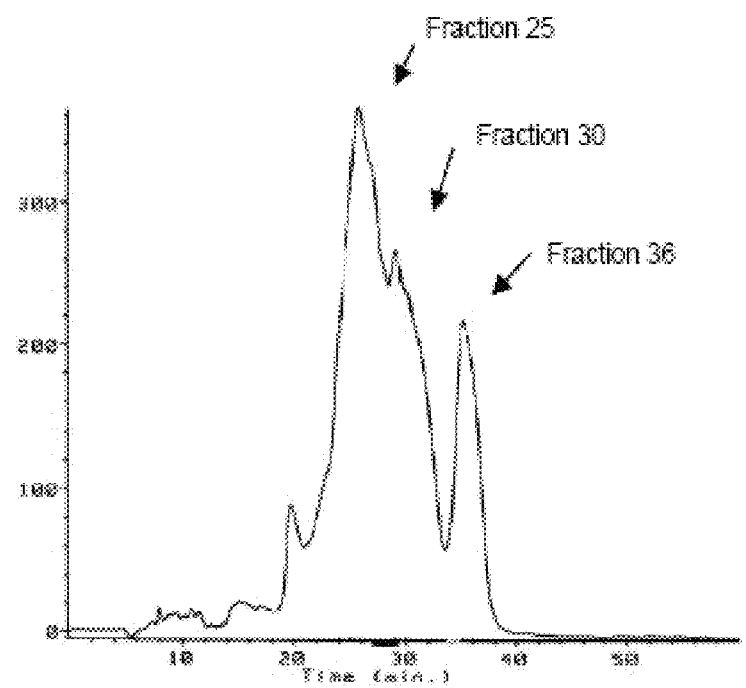

FIG. 40. Resulting elution profile after RP-HPLC following affinity absorption for hGM-CSF.

Figure 41:
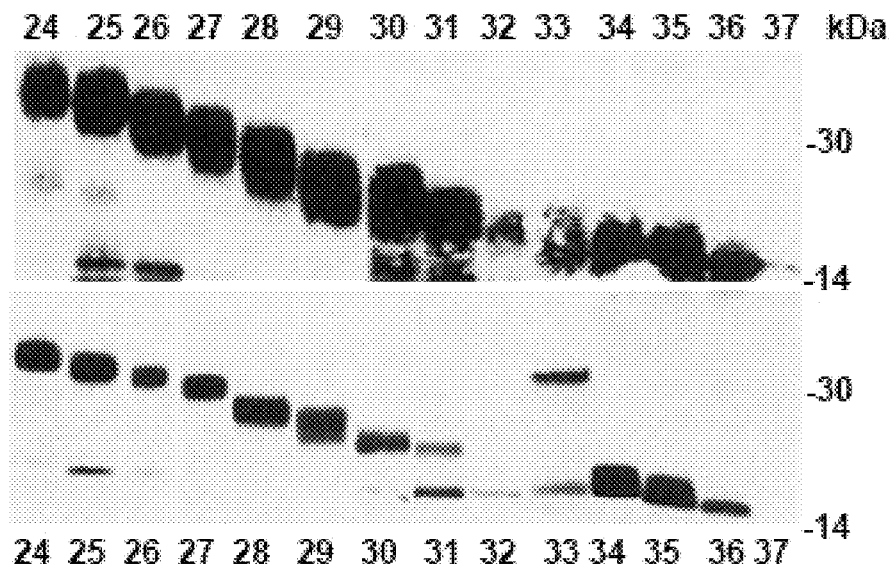

FIG. 41. SDS-PAGE (lower panel) and Western blot (upper panel) of fractions collected after RP-HPLC following affinity immunoabsorption for hGM-CSF. Western blot revealed changes in molecular weight profile of hGM-CSF secreted by Pro-GM-SF between fractions. Fractions eluted at 24 to 28 minutes corresponded to a first peak on RP-HPLC elution profile, fractions collected between 29 and 31 minutes represented second peak whereas the third peak falls into the fractions collected between 34 to 36 minutes.

Figure 42:
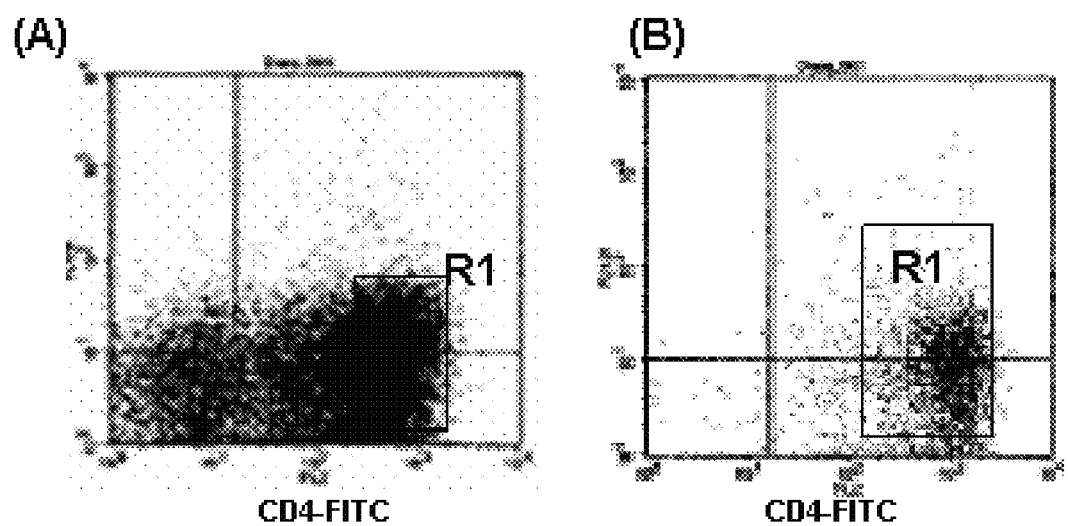

FIG. 42. Separation of CD4$^+$ cells from the culture of PHA activated human lymphocyte culture: FIG. 42A, the cells labelled with anti human CD4-FITC were gated (R1) and sorted from the rest of the cell population. The sorted cells were further analysed for purity; FIG. 42B, 100% of the cells in sorted population were CD4 positive.

Figure 43:
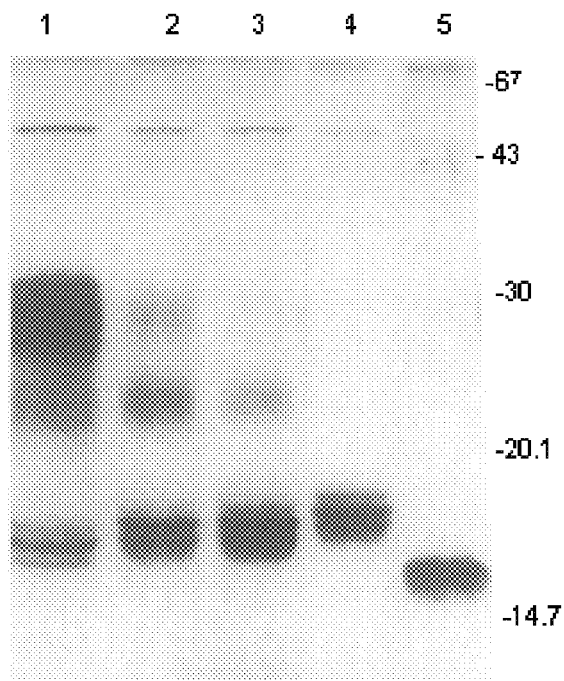

FIG. 43. Gel Electrophoresis of deglycosylated hGM-CSF derived from Pro-GMsf. The purified hGM-CSF was exposed to PHGase F digestion for different period of time. Lane 1—0 min, lane 2—10 min, lane 3—20 min, lane 4—40 min of incubation. Lane 5—recombinant human GM-CSF derived from E. coli. Proteins were visualized by silver staining. Molecular weight markers are indicated.

Figure 44:
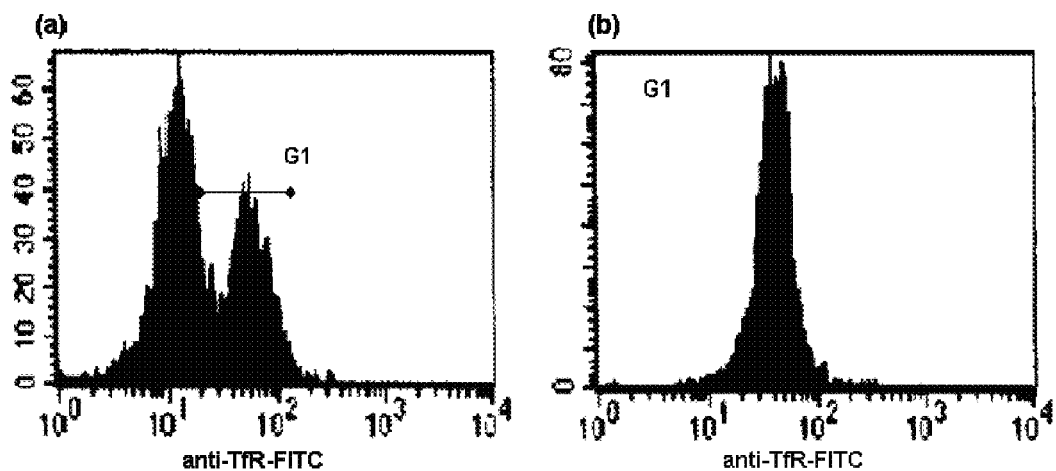

FIG. 44. Identification and sorting of TfR$^+$ cells of mouse myeloma Sp2 cell line. The TfR$^+$ cells were gated and sorted out as shown in FIG. 44a. The identified TfR$^+$ sorted cells were collected for purity analysis as shown in FIG. 44b.

Figure 45:
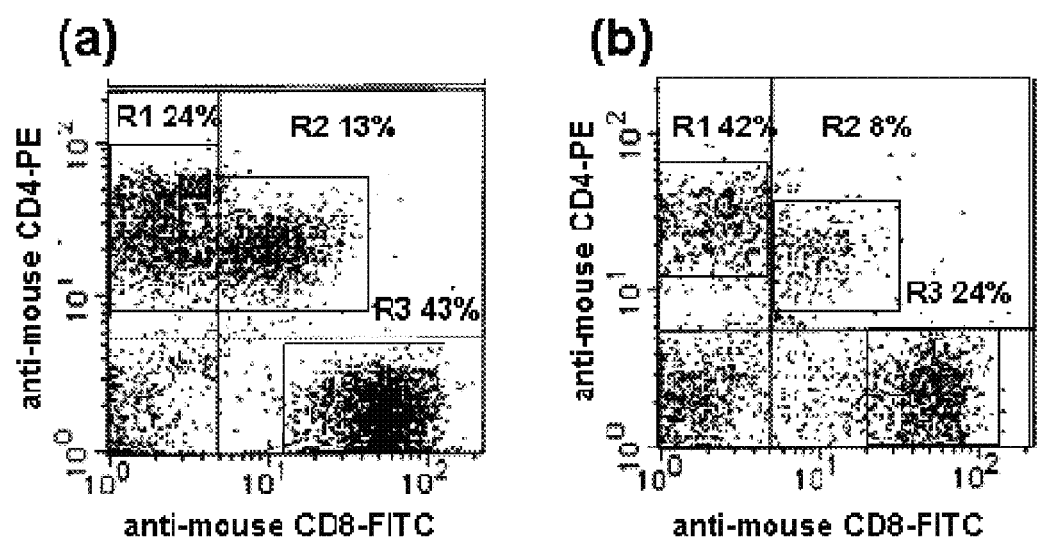

FIG. 45. FACS profiles of mouse mononuclear cells from (FIG. 45a) peripheral blood and
(FIG. 45b) spleen stained with anti-mouse CD4 and CD8. The gated regions R1 and R3 represent single positive effector helper (CD4$^+$CD8$^{31}$) and cytotoxic (CD8$^+$CD4$^-$) T cells, whereas R2 contains double positive (CD4$^+$CD8$^+$) T cells.

Figure 46:
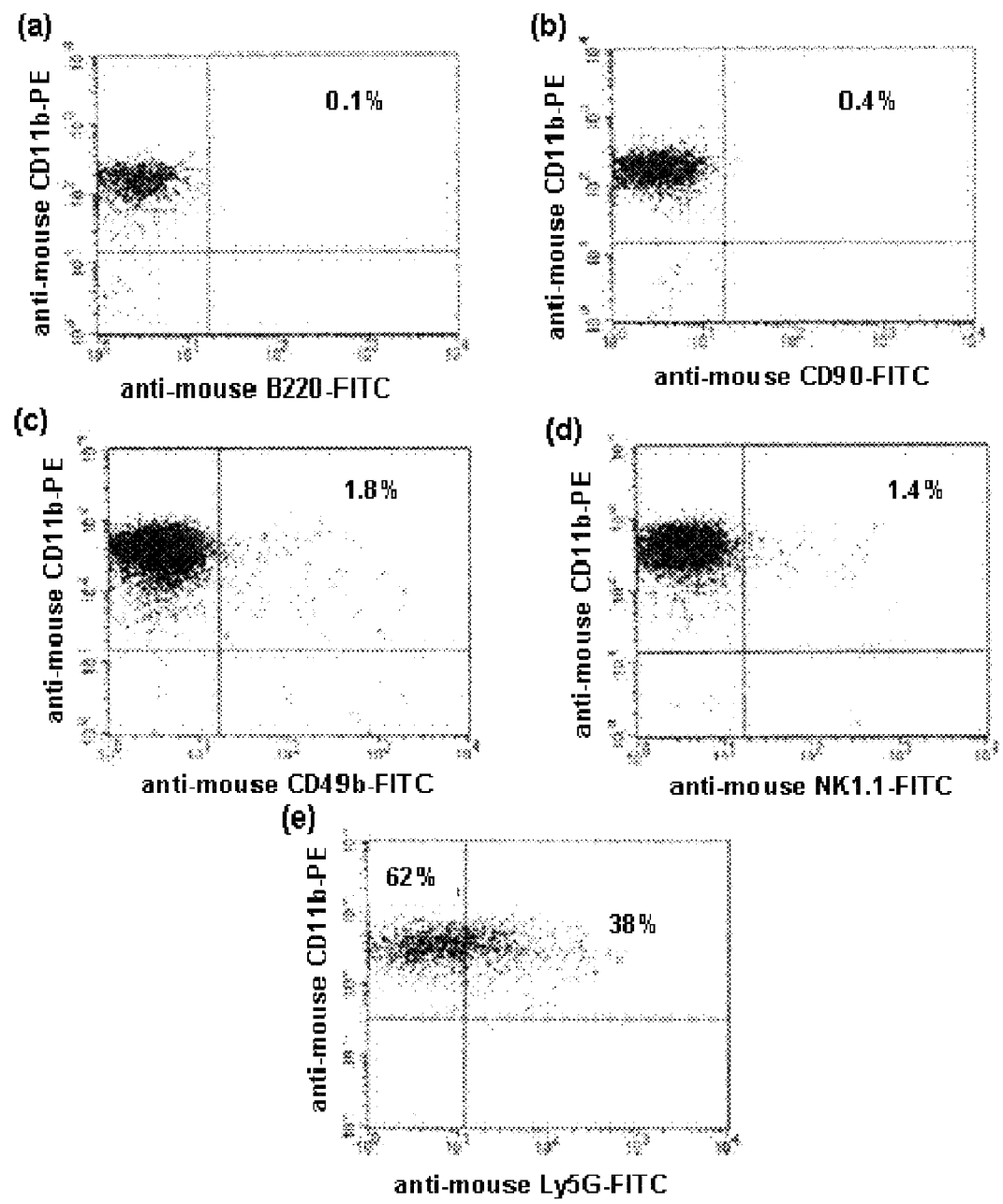

FIG. 46. Purity profiles of mouse monocytes isolated from peripheral blood by negative selection with magnetic beads. The isolated cells were tested for expression of CD11b and B220 (FIG. 46a), CD11b and CD90 (FIG. 46b), CD11b and CD49 (FIG. 46c), CD11b and NK1.1 (FIG. 46d) and CD11b and Ly5G (FIG. 46e), 100% of the isolated cells were positive for CD11b and at the same time more than 98% of these cells were negative for B220, CD90, CD49b and NK1.1. Approximately, 38% of CD11b$^+$ cells expressed Ly5G on their surface at low levels.

Figure 47:
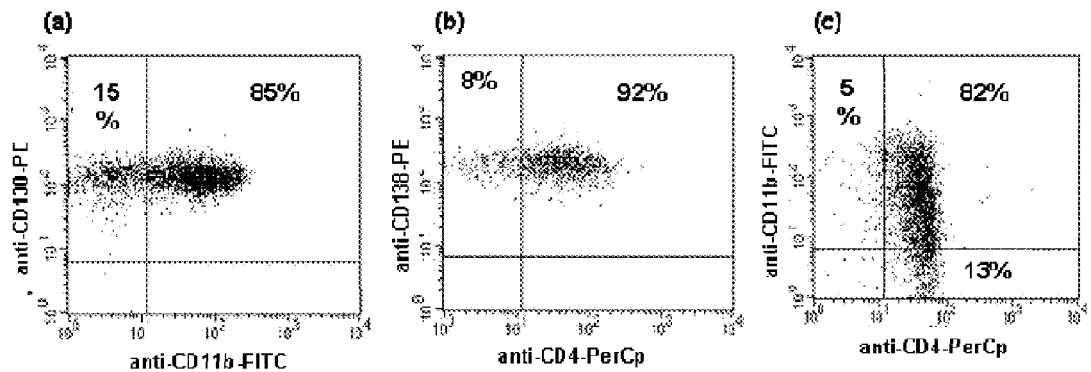

FIG. 47. FACS profiles of CD138 and CD11b expression (FIG. 47a), CD138 and CD4 expression (FIG. 47b) and Cd11b and CD4 expression (FIG. 47c) on STmMm tri-hybrid derived from one lymphoid immortal cell of Sp2, primary mouse CD4$^+$ T cell and CD11b$^+$ monocyte. The phenotype of B lymphoid lineage was confirmed by expression of CD138 on 100% of the tri-hybrid cells, (a) and (b) At least 82% of the cell population expressed all three CD markers, with only 5% of cells being CD138 positive without co-expressing either CD4 or CD11b.

Figure 48:
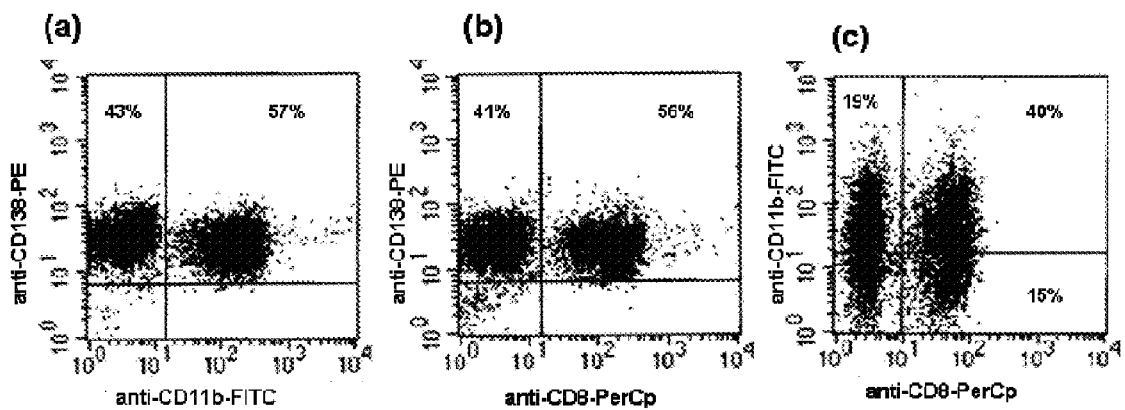

FIG. 48. Typical FACS profiles of CD138 and CD11b expression (FIG. 48a), CD8 and CD138 expression (FIG. 48b) and CD11b and CD8 expression (FIG. 48c) on STmMm tri-hybrid derived from one mouse lymphoid immortal cell of Sp2, primary mouse cytotoxic CD8$^+$ T cell and mouse CD11b$^+$ monocyte. Whilst the expression of mouse CD138 was confirmed on 97-100% of the tri-hybrid cells (a) and (b), the co-expression of T cell and monocyte markers was detected on 56% and 57% of tri-hybrid cell population, respectively. Approximately 40% of the entire tri-hybrid population co-expressed all three markers (c) and only 14% expressed neither CD8 nor CD11b on their surface.

Figure 49:
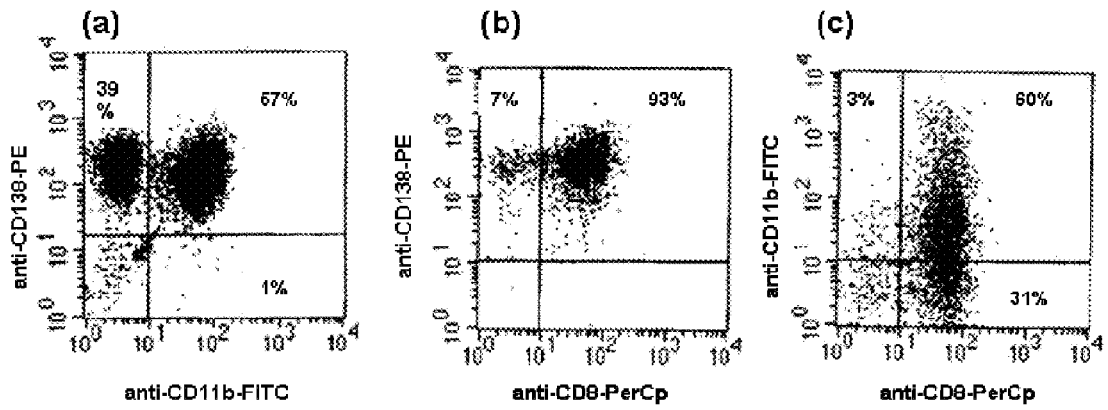

FIG. 49. Typical FACS profiles of CD138 and CD11b expression (FIG. 49a), CD8 and CD138 expression (FIG. 49b) and CD11b and CD8 expression (FIG. 49c) on STmMm tri-hybrids derived from one mouse lymphoid immortal cell of Sp2, one primary mouse double positive CD4+CD8+ T cell and one primary mouse CD11b+ monocyte. 98-100% of tri-hybrid cell population were positive for CD138 with 93% of the population also positive for CD8 (b). Approximately 57-60% of the entire cell population were simultaneously positive for CD138, CD8 and CD11b.

FIG. 47. FACS profiles of CD138, CD4 and Cd11b expression on STmMm tri-hybrid derived from one lymphoid immortal cell of Sp2, primary mouse CD4$^+$ T cell and CD11b$^+$ monocyte. The phenotype of B lymphoid lineage was confirmed by expression of CD138 on 100% of the tri-hybrid cells, (a) and (b) At least 82% of the cell population expressed all three CD markers, with only 5% of cells being CD138 positive without co-expressing either CD4 or CD11b.

FIG. 48. Typical FACS profiles of CD138, CD8 and CD11b expression on STmMm tri-hybrid derived from one mouse lymphoid immortal cell of Sp2, primary mouse cytotoxic CD8$^+$ T cell and mouse CD11b$^+$ monocyte. Whilst the expression of mouse CD138 was confirmed on 97-100% of the tri-hybrid cells (a) and (b), the co-expression of T cell and monocyte markers was detected on 56% and 57% of tri-hybrid cell population, respectively. Approximately 40% of the entire tri-hybrid population co-expressed all three markers (c) and only 14% expressed neither CD8 nor CD11b on their surface.

FIG. 49. Typical FACS profiles of CD138, CD8 and CD11b expression on STmMm tri-hybrids derived from one mouse lymphoid immortal cell of Sp2, one primary mouse double positive CD4$^+$CD8$^+$ T cell and one primary mouse CD11b$^+$ monocyte. 98-100% of tri-hybrid cell population were positive for CD138 with 93% of the population also positive for CD8 (b). Approximately 57-60% of the entire cell population were simultaneously positive for CD138, CD8 and CD11b.

Figure 50:
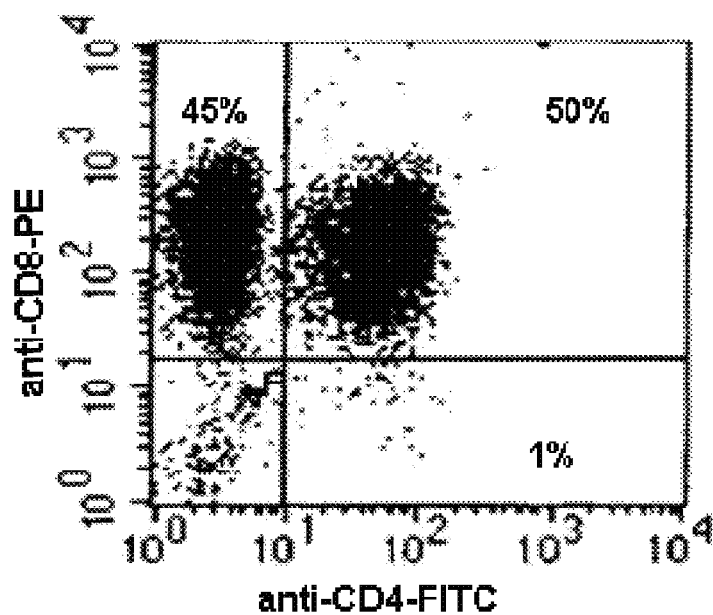

FIG. 50. A typical profile of CD4 and CD8 expression on the surface of STmMm tri-hybrids derived from one mouse lymphoid immortal cell of Sp2, one primary mouse double positive CD4$^+$CD8$^+$ T cell and one primary monocyte. Whilst 95% of cells were positive for CD8, only 50% of the tri-hybrid population co-expressed CD4 and CD8. Notably, practically entire CD4$^+$ population was also positive for CD8.

Figure 51:
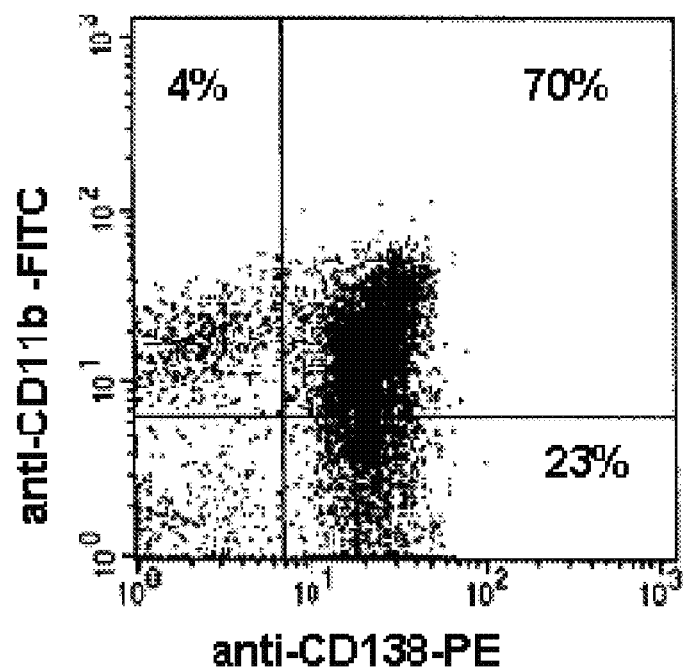

FIG. 51. A typical profile of CD138 and CD11b expression on the surface of SSMm tri-hybrids where 93% of the tri-hybrid population show positive staining for CD138 with 70% of cells co-expressing CD11b.

Figure 52:
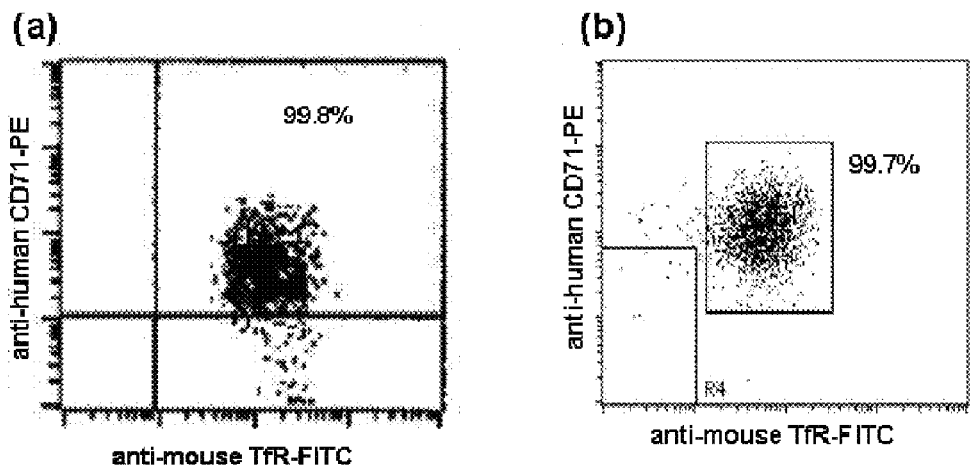

FIG. 52. Typical profiles of human CD71 and mouse TfR expression on the surface of SWMm (FIG. 52a) and SWMh (FIG. 52b) tri-hybrids. Regardless of the mouse or human source of the monocyte, 100% of tri-hybrids were positive for both human and mouse transferrin receptor.

Figure 53:
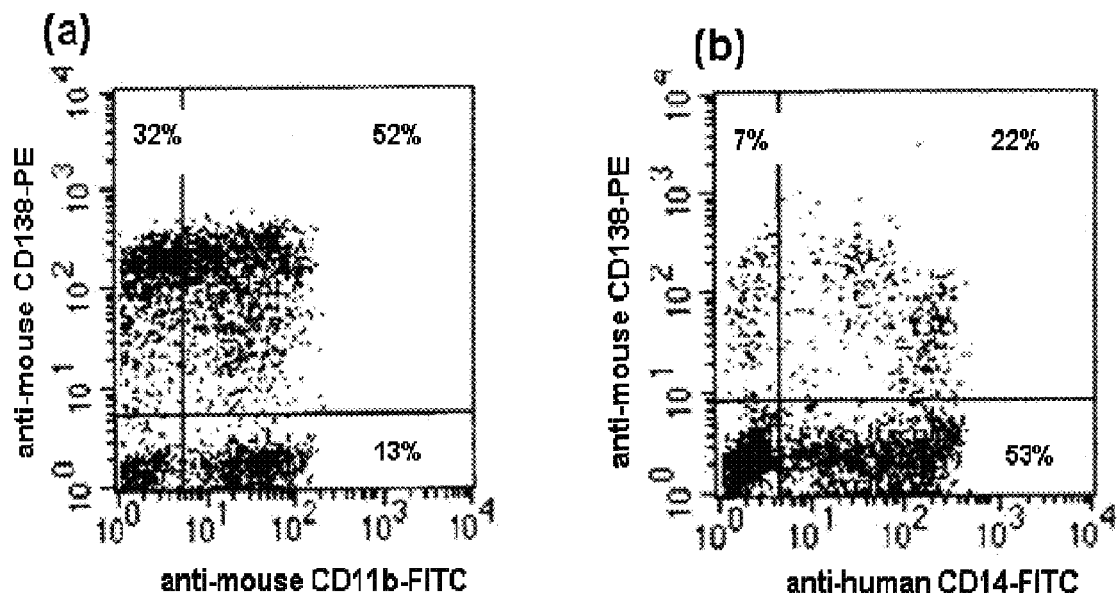

FIG. 53. Typical profiles of mouse CD138 expression on SWMm (FIG. 53a) and SWMh (FIG. 53b) tri-hybrids and either mouse CD11b or human CD14. The expression of mouse CD138 appears to be dependent on the mouse or human source of the monocyte. Whilst 84% of SWMm tri-hybrids were positive for mouse CD138, only 29% of SWMh had it on their surface.

Figure 54:
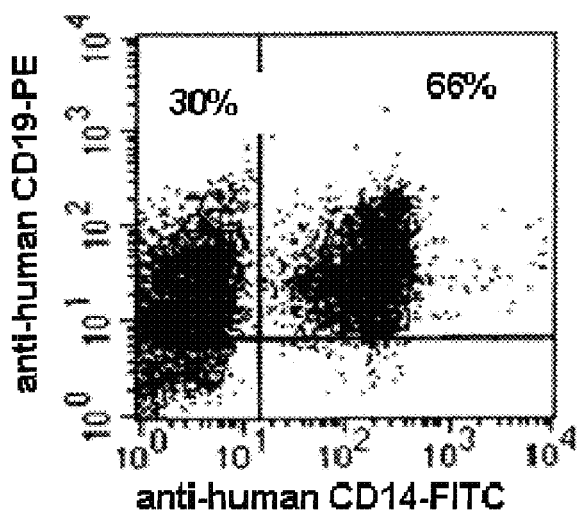

FIG. 54. A FACS profile of human CD19 and human CD14 expression on the surface of SWMh chimeric tri-hybrids shows 96% of the cells express human CD19 with 66% co-expressing human CD 14.

Figure 55:
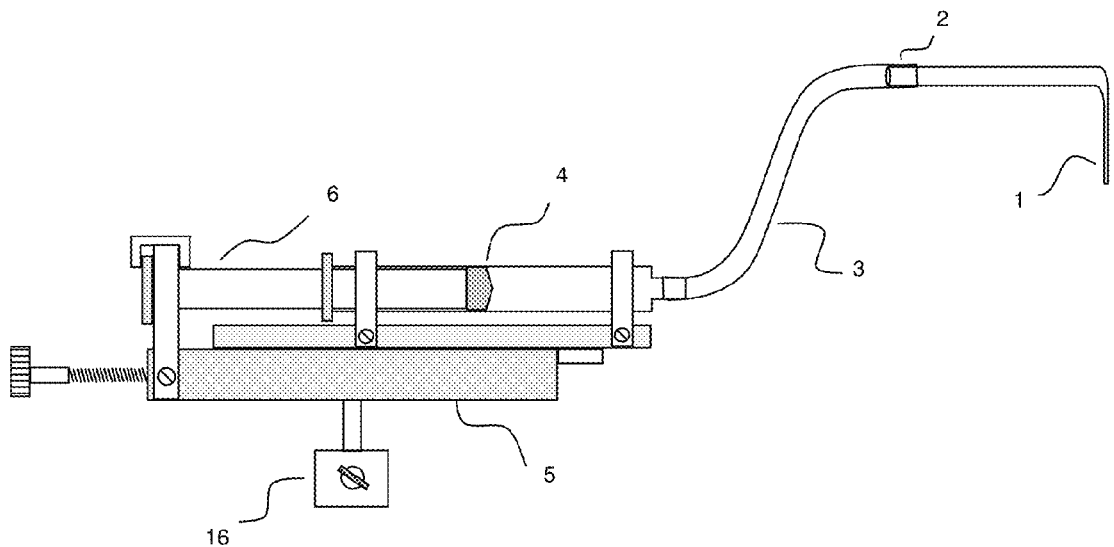
Figure 56:
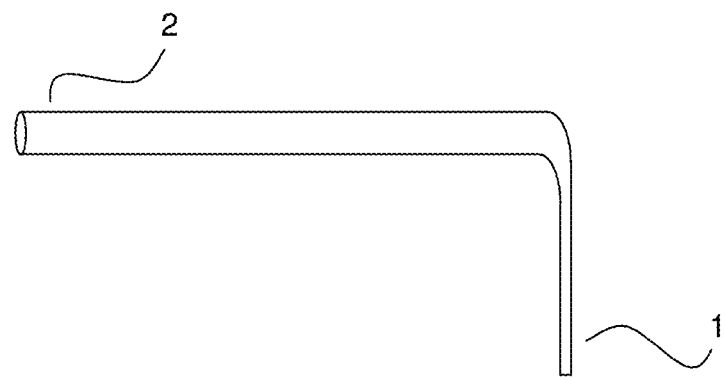
Figure 57:
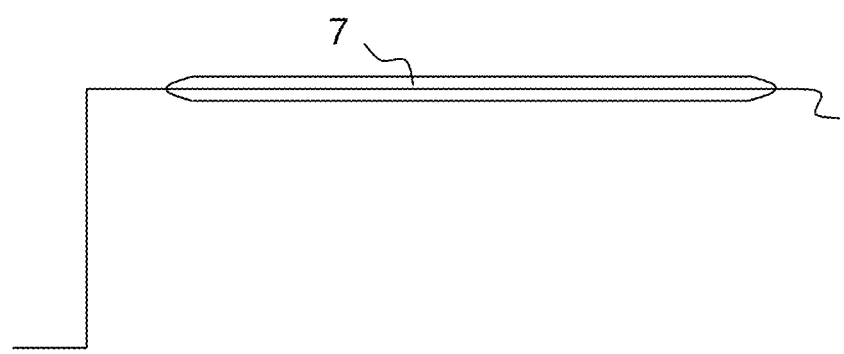
Figure 58:
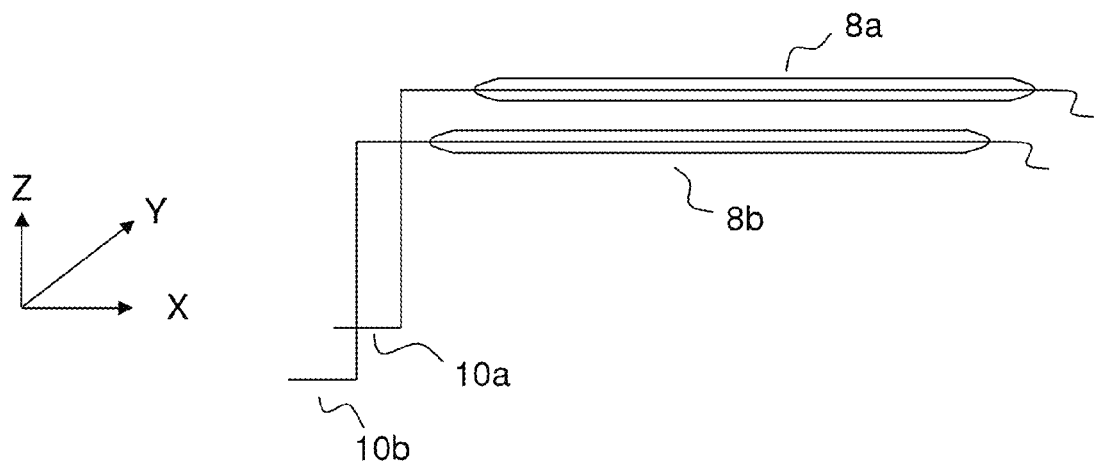
Figure 59:
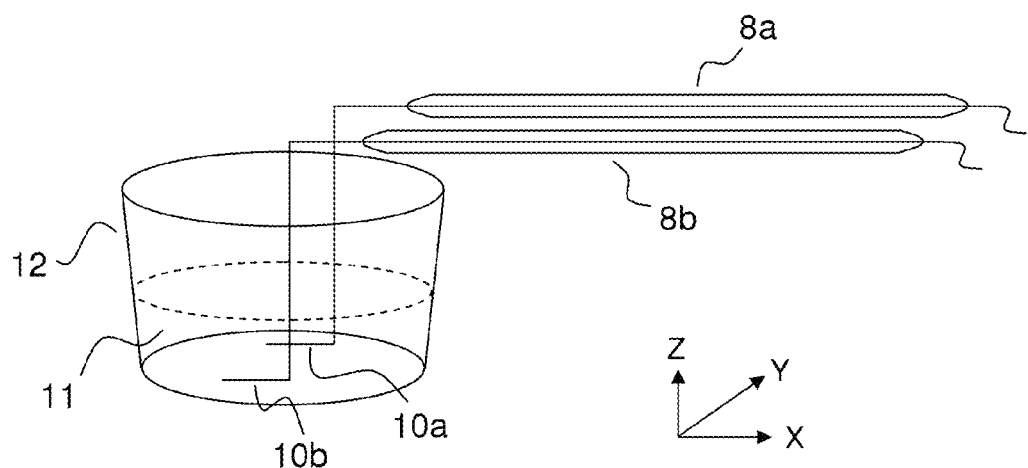
Figure 60:
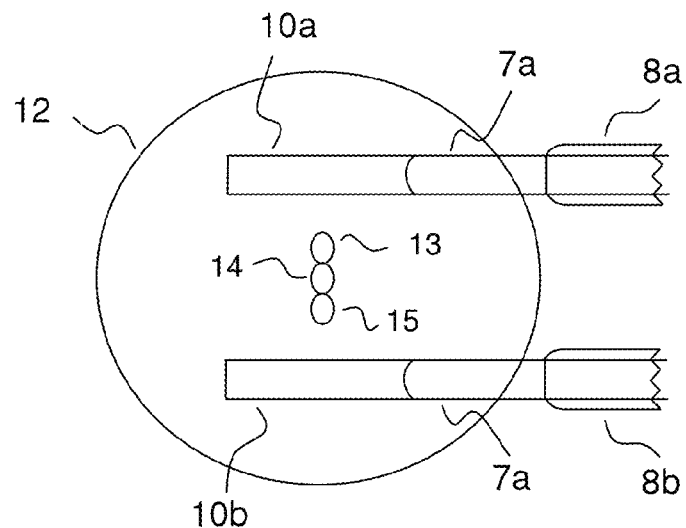
Figure 61:
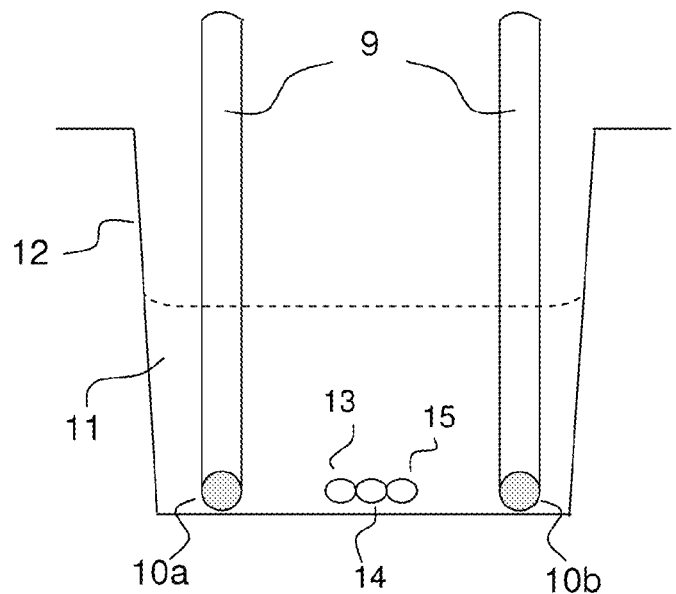
Figure 62:
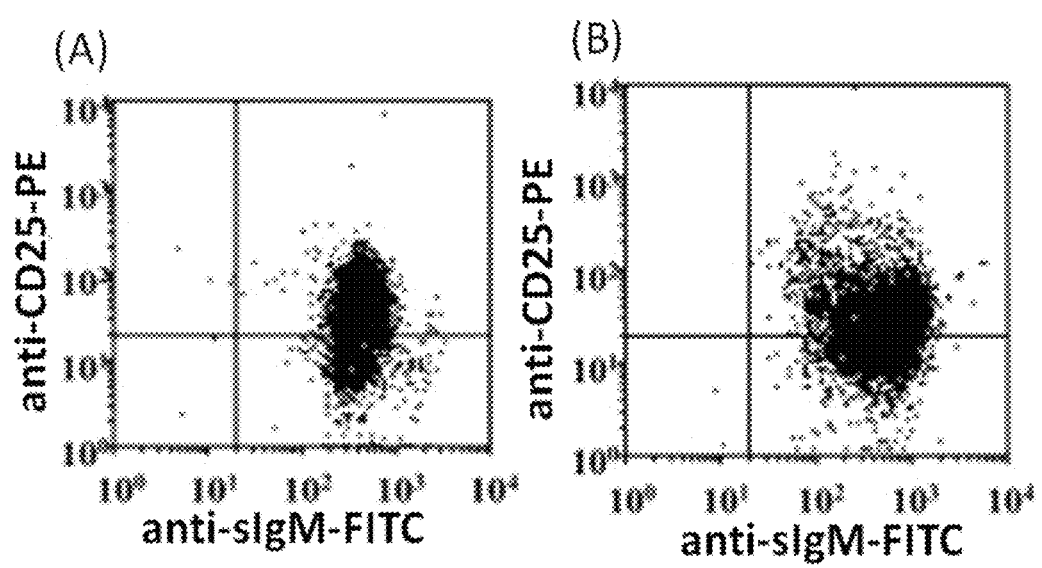

FIG. 55. A single-cell manipulation/delivery system.
FIG. 56. A glass micro-pipette.
FIG. 57. A micro-electrode.
FIG. 58. Two parallel micro-electrodes.
FIG. 59. Two micro-electrodes in a well of a tissue culture plate.
FIG. 60. A top-view of a well containing 3 cells intermediate 2 microelectrodes.
FIG. 61. A side-view of the well of FIG. 60.
FIG. 62. Expression of CD25 and sIgM on the surface of hybrid cells created by hybridization of one KBT cell and one shIgM$^+$CD25$^+$B cell before (FIG. 62A) and after (FIG. 62B) stable transfection with second protein hIL-2.

DESCRIPTION OF THE INVENTION

A preferred embodiment of the invention is further described by the following non-limiting examples with reference to the accompanying figures.

EXAMPLE 1

1. Cell Selection, Cell Manipulation and Single-cell Cloning

The following examples describe cell preparations including selection and isolation (or sorting) of mammalian cell lines and primary cells used for the creation of cross-lineage tri-hybrids, and for the expression of desired proteins. The choice of particular selection technique to obtain pure population of cells with specific characteristics or use of a particular marker (or markers) for the isolation of the cells of a particular phenotype is not in anyway restrictive but rather indicative. Other cellular markers or sorting procedures can be used to deliver similar results.

1.1. Selection of Cells as a Source of Oncogene from Mammalian Cell Lines

All immortal cell lines (see below) were grown in suspension culture under standard (normal) conditions in a $CO_2$ incubator at 37° C. in humidified 5% $CO_2$ atmosphere using modified RPMI1640 (Roswell Park Memorial Institute medium) with $NaHCO_3$ (JRH Biosciences), 20 mM Hepes (Sigma), 4 mM L-glutamine (Sigma) and supplemented with 10% Foetal calf serum, FCS, (JRH Biosciences). Unless stated otherwise, the tissue culture medium (TC medium) described here is the standard medium to culture all the immortal cell lines, primary cancer cells, primary cell cultures and established tri-hybrid cell lines for the present invention. In general, all the cell lines, primary cancer cells and primary cells used were cultured in antibiotics-free environment. However, when there was a suspicion of a high risk of bacterial and/or fungal contamination, 2% penicillin (5000 units)/streptomycin (5 mg) solution (Sigma) was included in the standard medium.

Human Cell Lines

Human cell lines that may be used in this invention are as follows: —
- a) Common myeloid progenitor lineage, K562 (a cell line derived from a human chronic myelogenous leukaemia),
- b) T lymphoid lineage, MOLT4 (human T lymphoblast), and
- c) B lymphoid lineage, WIL2NS (human B lymphoblast).

Non-human Cell Line(s)

A non-human cell line that may be used in this invention is a mouse myeloma cell line-Sp2 (B lymphocyte plasma cell).

1.1.1. Single-cell Delivery System

Cell isolation or sorting, cell manipulation and single-cell cloning are essential processes throughout this invention. Here we describe a single-cell delivering system which was established for manipulating and/or cloning a single cell of interest. The cell delivery system (FIG. 55) consists mainly of a glass micro-pipette, a 1 ml syringe and a one-dimensional coarse manipulator. FIG. 56 shows a glass, L-shape micro-pipette used for picking up a single cell of interest. The pipette was made of a haematocrit capillary tube, 75 millimetres (mm) in length, with an outer and an inner diameter of 1.5 mm and 1.10 mm, respectively. By using heat, one end of the tube was pulled such that the tip (1) with an inner diameter of approximately 250-300 micrometres ($\mu m$) and the wall of the tip of approximately 30 $\mu m$ thick was obtained. The other end of the micro-pipette remained unmodified (2). In the cell delivery system (FIG. 55), a syringe (4) is mounted on a coarse manipulator, which is in turn mounted on a magnetic stand (16). The system works in such a way that the plunger (6) of the syringe can be forced to move very slowly, either forward or backward relatively to the syringe. In order to manipulate a single cell of interest, the syringe must be connected to the unmodified end of the micro-pipette (2) as shown in the figure using a flexible, medical grade tube (3). The single-cell delivering system must be sterilised by flushing several times with 70% alcohol and finally filled up without air bubbles with an appropriate tissue culture medium or solution, whatever needed, prior to any cell manipulation.

1.1.2. Single-cell Cloning

Clones of cells from each cell line were established by single cell cloning. A technique of cloning or manipulating a single cell of any biological cells, for example, cells of K562 cell line, used in this invention is described below.

5 $\mu l$ of cell suspension of K562 cells were taken out from its culture at the log-phase and deposited into a well of a tissue culture 96-well plate (TC plate, Becton and Dickinson or BD), which contained 150 $\mu l$ of TC medium. The well was designated a "cell-storing well". The plate was placed on an XY microscope stage of an inverted microscope (Axiovert 40C, Carl Zeiss). Prior to single cell manipulating/cloning process, a micro-pipette (FIG. 56) was completely filled up with TC medium without air bubbles. The micro-pipette, the tubing and the syringe of the single-cell delivery system (FIG. 55) were mounted on a one-dimensional coarse manipulator (Narishege). The micro-pipette tip (1) was arranged in such a way that the tip was located in the centre of the optical view of the microscope. To manipulate and clone a single cell of K562, the micro-pipette was inserted into the cell-storing well. By moving the plunger of the syringe very slowly in a sucking direction, a single cell of K562 was deposited in the micro-pipette. The micro-pipette was retracted from the cell-storing well. By moving the microscope stage laterally from the cell-storing well to an adjacent well, designated "a cloning well", and by subsequently inserting the micro-pipette into this cloning well, the single cell in the micro-pipette was then gently released from the micro-pipette. This was achieved by moving the plunger of the syringe very slowly in a releasing direction. The process of withdrawing a single cell from the cell-storing well and depositing the single cell into the cloning well was repeated numerous times until 60 single-cell clones per TC plate were obtained. The cloning plate was incubated in a humidified incubator (Thermoline Scientific), operated at 37° C. with 5% $CO_2$, for a period of 10 days. The medium in each cloning well was replenished with fresh TC medium regularly during the incubation period. Cell proliferation of each clone from each cloning well was recorded every 24 hours. At the end of the incubation period, a number of clones of K562 cells were established. A clone with the highest proliferation rate or the highest level of a marker of interest that expressed on the cell surface, for example, CD71 transferrin receptor on K562 cells, was selected for tri-hybrid production or further experiments.

1.1.3. Sorting of $CD71^+$ Cells

As an example, the method below describes a cell selection and sorting of CD71 positive cells from K562 cell line using a fluorescence-activated cell sorter (FACS).

Figure 1:
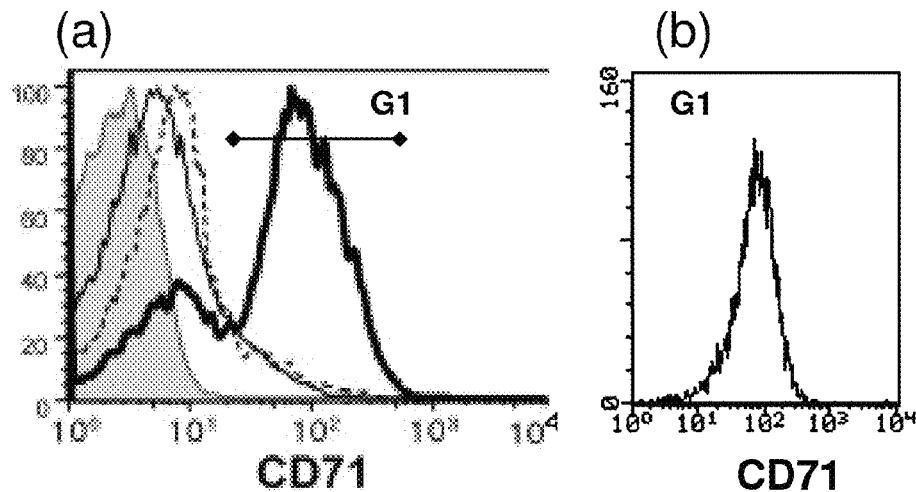
FIG. 1. Identification and sort-purified $CD71^+$ K562 cells. The $CD71^+$ cells were gated and sorted out as shown in FIG. 1a. The identified $CD71^+$-sorted cells were collected for purity analysis as shown in FIG. 1b.

$1\times10^5$ K562 cells suspended in 100 $\mu l$ of a phosphate buffer solution (Dulbeco PBS) containing 2% bovine serum albumin, BSA, (Sigma) were incubated in the dark with 20 $\mu l$ of either phycoerythrin (PE) conjugated anti-CD71 (BD Pharmingen) or PE conjugated isotypic control antibodies IgG2a,κ (BD Pharmingen) for 30 minutes at room temperature. The incubation mixture was diluted with 1 ml of PBS and the stained cells were collected by centrifuging at 300 g for 10 minutes. Following an additional wash with 1 ml of PBS, the stained cells were suspended in 1 ml of PBS and analysed immediately using a FACS (BD FACSCalibur). FIG. 1 shows profiles of $CD71^+$ cells of K562 cell line. The $CD71^+$ positive cells were gated and sorted out (FIG. 1a). Approximately, 65% of original K562 population were positive for CD71. The sorted cells were centrifuged at 300 g for 10 minutes and suspended in 1 ml of PBS for further experiments. 100 ml of suspended CD71$^+$-sorted cells were collected for purity analysis as shown in FIG. 1b. A purity of 99% of CD71$^+$ sorted cells was obtained. Following cell sorting, the CD71$^+$ cells of K562 cell line were either used for further experiments or placed in the culture under standard culture conditions and marked as CD71-enriched K562 cells. The same methodology was used to establish CD71-enriched WIL2NS and CD71-enriched MOLT4 cultures.

1.1.3.1. Sorting of CD71$^+$ Cells of Myelomonocytic Lineage from K562 Culture

To ensure the myelomonocytic phenotype of the cells for cell hybridisation experiments, CD71$^+$ K562 cells were further enriched for CD15$^+$ cells using FACS analysis and followed by sorting.

For this purpose, CD71-enriched K562 cells obtained from the process described in Section 1.1.3 were labelled with PE anti-human CD71 and FITC anti-human CD15 (BD Pharmingen). 1×10$^5$ washed CD71-enriched K562 cells suspended in 100 µl of PBS containing 2% BSA were incubated in the dark with 20 µl of either anti-human CD71-PE and anti-human CD15-FITC antibodies or negative isotypic control antibodies or FITC and PE labelled negative isotypic control antibodies for 30 minutes at room temperature. The incubation mixture was diluted with 1 ml of PBS and the stained cells were collected by centrifuging at 300 g for 10 minutes. Following an additional wash with 1 ml of PBS, the stained cells were suspended in 1 ml of PBS and analysed immediately using a FACSCalibur (BD).

Figure 2:
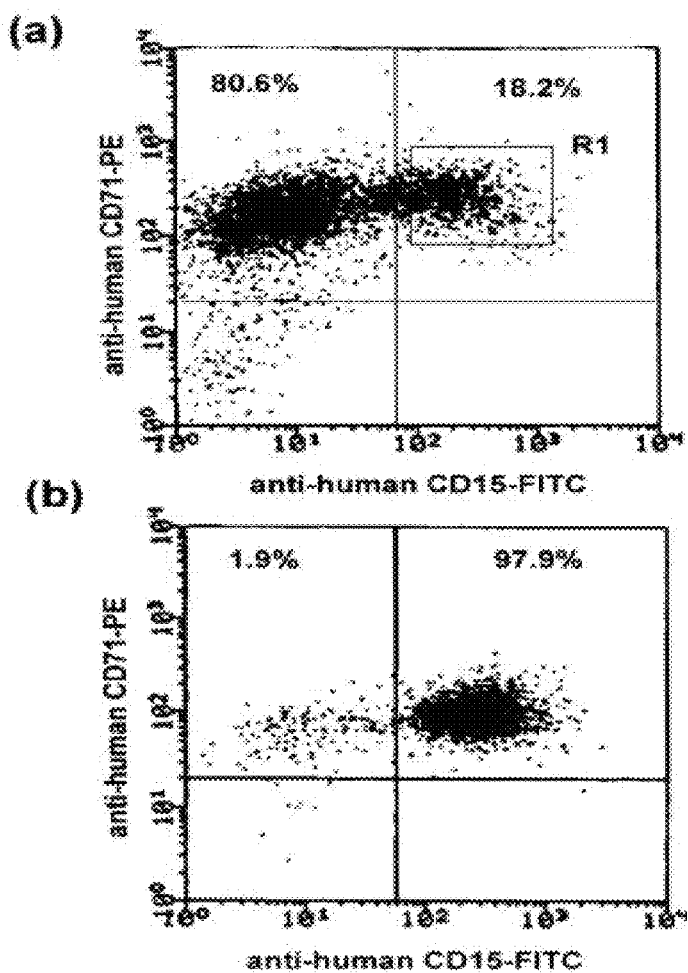
FIG. 2. FACS profiles of CD15 and CD71 positive K562 cells.

A typical FACS profile is shown in FIG. 2a. After 5 months in the culture, 99% of the CD71-enriched K562 cells remained positive for CD71, which approximately 18% expressed surface CD15. The cells positive for both CD71 and CD15 were gated (FIG. 2a) and sorted out. The sorted cells were collected by centrifuging at 300 g for 10 minutes and suspended in 1 ml of PBS for further experiments. 100 µl of suspended CD71$^+$CD15$^+$ sorted cells were collected for purity analysis. Following two months culture, the sorted cells were re-analysed for co-expression of CD71 and CD15 (FIG. 2b). The results indicate that that approximately 98% of the purified cells retained both CD71 and CD15. It was found that some of the cells which earlier expressed both CD71 and CD15 on the surface had lost their CD15 expression (FIG. 2b) suggesting that commitment to myelomonocytic lineage in K562 cells is not stable and reversible.

1.1.4. Selection of Transferin Receptor Positive Cells from Mouse Sp2 Cell Line

When mouse myeloma cell line Sp2 was used in the creation of tri-hybrids, the population was enriched for cells expressing mouse transferin receptor (TfR), analogue of human CD71.

Essentially the same protocol as in Section 1.1.3 was followed, describing enrichment of human cell lines for CD71$^+$ cells, except that FITC-conjugated rat anti-mouse TfR antibodies (Abcam) was used instead of PE-conjugated mouse anti-human CD71. The isotype controls were adjusted accordingly.

FIG. 44 shows profile of TfR$^+$ cells of Sp2 cell line. The TfR$^+$ positive cells were gated and sorted out (FIG. 44a). Approximately, 45% of original Sp2 population were positive for TfR. The sorted cells were centrifuged at 300 g for 10 minutes and suspended in 1 ml of PBS for further experiments. 100 ml of suspended TfR$^+$-sorted cells were collected for purity analysis as shown in FIG. 44b. A purity of 99.5% of TfR sorted cells was obtained. Following cell sorting, the TfR$^+$ cells of Sp2 cell line were either used for further experiments or placed in the culture under standard culture conditions and marked as TfR-enriched Sp2 cells.

1.2. Selection of Cells as a Source of Oncogene from Primary Cancer Cells

As an example, the method below describes the selection of transformed cells of the myelogenous lineage from bone marrow samples obtained from patients with acute myelogenous leukaemia (AML). The same method could also be applied to select cells of other lineages from bone marrow samples of corresponding blood malignancies.

Bone marrow aspirates from patients with AML were obtained after informed consent. The samples were extracted from the patients whose diagnosis of AML was established prior to conducting experiments. AML mononuclear cells were isolated using the same density gradient centrifugation procedure as described in Section 1.3.1, and CD34$^+$ cells from the samples were sorted or isolated using a FACS.

To stain or label the mononuclear cells obtained above, 10 µl of a mouse anti-human CD34-PE antibody (BD Pharmingen) or a PE isotype control antibody (BD Pharmingen) were added to 100 µl of a given aliquot of 1×10$^6$ mononuclear cells in a staining medium (PBS+5% BSA). For a given aliquot, the staining mixture was incubated for 30 minutes on ice. 10 ml of ice-cold staining medium was added to the cell pellet and centrifuged for 7 min at 350 g and 4° C. Supernatants were aspirated and then the cell pellet was re-suspended by flicking the tube in which a comparable volume of ice-cold staining medium was added. The stained cells were centrifuged and washed once more in ice-cold staining medium. The labelled cells were suspended in staining medium and applied to FACS. After setting appropriate sorting gates for CD34$^+$ cell population, the cell fractions were collected.

For enrichment cultures, 40×10$^3$ cells of the CD34$^+$-enriched cells were plated in 12 well plates pre-coated with synthetic extracellular matrix. The cells were expanded in complete TC medium supplemented with 57 mM of β-mercaptoethanol (Sigma), 1 mM hydrocortisone, and 20 ng/ml of human IL-3 and human G-CSF. After 48 hours in the culture, the cells were further selected for CD15 expression using FACS.

For fluorescence-cell staining, a mouse anti-human CD15-FITC (BD Pharmingen) and a mouse anti-human CD34-PE (BD Pharmingen) were used and a similar cell staining method described earlier in this Section was also employed. The stained samples were analysed using a FACS. After setting appropriate sorting gates for CD34 and CD15 positive cell population (CD34$^+$CD15$^+$) or for CD34 positive and CD15 negative cell population (CD34$^+$CD15$^-$), the fractions were collected.

Figure 3:
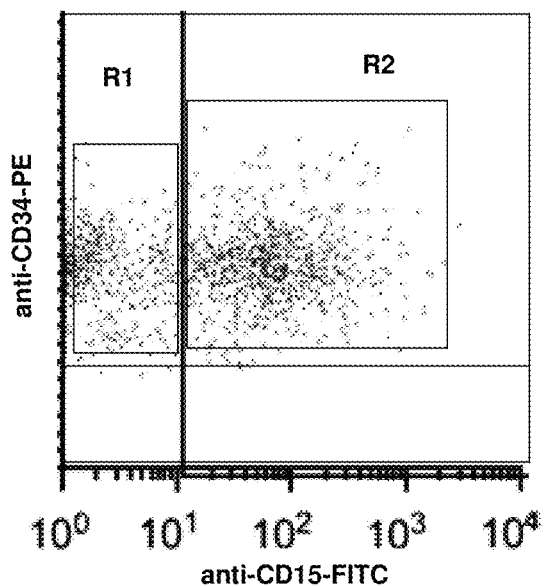
FIG. 3. Expression of CD15 on $CD34^+$ AML mononuclear cells.

The profile of CD15 expression on the CD34$^+$ AML cells after 48 hours in culture is shown in FIG. 3. Approximately, 54% of AML mononuclear cells tested positive for CD15 whilst maintaining their CD34 expression, whereas the rest of the cell population retained its CD34 expression without committing to myelomonocytic lineage. The CD34$^+$CD15$^+$ cells were used in experiments for creating tri-hybrids.

1.3. Primary Cells

Primary cells can be derived from any lymphoid tissues such as peripheral blood, cord blood, spleen, bone marrow, thymus, tonsils, and regional lymph nodes. As a first step, all lymphoid tissues were processed to isolate mononuclear cells.

1.3.1. Isolation of Human Mononuclear Cells from Bone Marrow, Peripheral Blood or Umbilical Cord Blood Peripheral blood samples were collected from healthy individuals after informed consent. Each blood sample was collected in heparinised tubes (Vacutainer, BD), pooled, and diluted in RPMI1640.

Human bone marrow aspirates were obtained from patients who underwent bone marrow biopsies and had normal bone marrow without any blood abnormalities. The samples were diluted at a ratio of 1:3 with RPMI1640.

Human umbilical cord blood samples were obtained from normal full-term vaginal deliveries after informed consent. Each cord blood was collected with a heparinised 60 ml syringe after delivery of the infant and ligation of the cord, prior to expulsion of the placenta. Each sample was diluted in RPMI1640.

Peripheral blood mononuclear cells (PBMCs), bone marrow mononuclear cells (BMMCs) and umbilical cord blood mononuclear cells (UCBMCs) were prepared by density centrifugation over Ficoll-Paque (Amersham Pharmacia). In brief, 10 ml of Ficoll-Paque were layered under 20 ml of cell suspension using cannulae tube attached to a 20 ml syringe. The sample cells were centrifuged at 1,700 rpm (700 g) for 40 minutes at 4° C. The cells in the interface were collected and washed in 50 ml of RPMI1640 by centrifugation at 2,000 rpm (1,000 g) for 10 minutes. The supernatant was discarded and pelleted cells were re-suspended in 40 ml of RPMI1640 and centrifuged at 1,300 rpm (400 g) for 10 minutes. The red blood cells and platelets were removed by lysis with 0.83% (wt/vol) $NH_4Cl$ and a second centrifugation over Ficoll-Paque diluted at a ratio of 1:2 with PBS, respectively.

The isolated mononuclear cells were used for culturing or analysis and sorting into cell specific fractions through a FACS or a magnetic bead separation system.

1.3.2. Isolation of Human Mononuclear Cells from Solid Lymphoid Tissues

The method below describes the procedure used in this invention for isolating mononuclear cells from spleen, thymus, tonsil or regional lymph nodes. A method for cell staining and sorting is also given.

Spleen samples were obtained from organ transplant donors following the national ethical guidelines. Blocks of spleen, approximately 2×2×3 cm each, were kept at 4° C. in RPMI 1640 until isolation of the splenocytes. Each block was cut into small pieces through the mesh of a sterile sieve using the plunger of a syringe. The cells were then dissociated enzymatically by digestion with 20 U/ml type VII collagenase (Sigma) and 20 U/ml DNase (Sigma) in complete medium for 30 minutes at room temperature. The cell aggregates were further dissociated by the addition of EDTA to attain 10 mM and agitation for 5 minutes at room temperature. The splenocytes were then washed with complete medium twice to spot enzymatic digestion and re-suspended in RPMI 1640. These conditions did not affect surface molecule expression compared to non-enzymatic dissociation procedures (McIlroy et al 1995). Spleen mononuclear cells were isolated from these splenocyte suspensions by density gradient centrifugation as described in Section 1.3.1 except for the removal of red blood cells. The spleen mononuclear cells were re-suspended in RPMI1640 and cell concentration was adjusted to $1×10^6$ cells per ml. Cell viability was above 98% as determined by trypan blue exclusion.

Thymuses were obtained from children undergoing cardiac surgery after informed consent of their parents. The thymocytes were isolated from the thymuses by disrupting the thymus tissue and flushing the thymocytes out of the tissue with a syringe filled with RPMI1640 medium. The thymocytes were purified by density gradient-centrifugation as described above.

Tonsils were obtained from patients undergoing tonsillectomy for inflammatory disorders, following informed consent. The tissue samples were stored on ice in complete medium and 250 µg/ml gentamicin and processed within 3 hours. The tonsillar tissue was cut into pieces after the epithelial layer was removed and the tissue blocks were gently aspirated through a cut-off transfer pipette. The tonsillar cells were then isolated using the same procedure as described previously in the isolation of splenic mononuclear cells.

1.3.3. Isolation of Lineage Specific Primary Cells from Mononuclear Cells Derived from Various Tissues Human cells of B lymphoid lineage, T lymphoid lineage and myeloid lineage were isolated by standard procedures using FACS analysis and cell sorting or magnetic cell sorting. Non-limiting examples of cell staining and sorting for the isolation of lineage specific primary cells from various tissues are given below.

1.3.3.1. Isolation of B Cells, Helper T Cells and Myelomonocytic Cells from Human Spleens and Peripheral Blood The tissue samples were initially processed to extract a mononuclear cell population as described in Section 1.3.1. Fluorescence-cell staining followed by cell sorting was then performed within 4 hours of the isolation of the mononuclear cell population. The cells were suspended in complete medium under standard culture conditions (see Section 1.1) until staining.

1.3.3.1.1. Cell Staining and Sorting of Primary Mature B Cells, Effector T Cells and Myelomonocytic Cells Derived from Various Tissues Below are examples of staining and sorting of B and T cells from primary cells. Usually, the selections of B cells and helper T cells were based on the surface expressions of CD19 and CD4, respectively, whereas myelomonocytic cells on the surface expression of CD14 and/or CD16.

In brief, 10 µl of each of mouse anti-human CD19-FITC antibody (BD Pharmingen) and mouse anti-human CD4-PE antibody (BD Pharmingen) or appropriate isotype control were added to a 100 µl aliquot of mononuclear cells in staining medium (PBS+5% BSA), containing $1×10^5$ cells per aliquot. For a given aliquot of mononuclear cell population, the staining mixture was incubated for 30 minutes on ice. 10 ml of ice-cold staining medium was added to the staining mixture and centrifuged for 7 minutes at 350 g and 4° C. The supernatant was aspirated and then the cell pellet was re-suspended by flicking the tube in which a comparable volume of ice-cold staining medium was added. The stained cells were centrifuged and washed once more in ice-cold staining medium. The process was repeated for other aliquots. The stained cells were analysed using a FACS. At least 20,000 gated events were analysed for each sample. After setting appropriate sorting gates for CD19 positive B cell population ($CD19^+CD4^-$) or for CD4 positive T cell population ($CD4^+CD19^-$), the fractions were collected. 1 ml of each fraction was collected for purity analysis and the rest of each fraction was re-suspended in complete medium for further experiments.

1.3.3.1.2. Recovery and Analysis of Sorted Cell Populations

A small number of cells ($\leq 5×10^5$ cells) were sorted directly into microcentrifuge tubes with appropriate adapters. Prior to sorting, a small volume (0.1 to 0.2 ml) of supplemented RPMI1640 was added to the recovery tubes in order to mix with the sorted sample and improve viability of sorted cells. After sorting, provided the number of recovered cells permitted, 20 µl of each sorted cell sample was diluted at 1:10 with staining medium for re-analysis to verify its purity. An acceptable purity was ≥95%. Further 20 to 40 μl of FCS per ml of sorted sample was added and followed by centrifugation for 7 min at 350 g, 4° C. The cells were then re-suspended in the standard tissue culture medium. If sufficient cells were available, they were counted to determine yield.

A FACS profile of spleen samples labelled with anti-human CD19-FITC and anti-human CD4-PE is shown in FIG. 11a, whereas the profiles of purity analysis of sorted CD19$^+$ B cells and CD4$^+$ T cells are shown in FIGS. 11b and 11c (see KBT hybrid characterization). The cell purity in the fractions exceeded 98% for CD19$^+$ cells and 96% for CD4$^+$ cells.

The sorting and purity profiles for CD19$^+$ and CD4$^+$ cells from peripheral blood were essentially similar to those from spleen samples, only fewer numbers of each cell population were obtained.

For the isolation of human monocytes and myelomonocytic cells, the mononuclear cell population was first depleted of CD14 negative cells using human CD14 magnetic beads, MACS (Miltenyi Biotec GmbH), according to the manufacturer's instructions. Positively selected CD14 cells were further stained or labelled with mouse anti-human CD16-PE (BD Pharmingen) and mouse anti-human CD14-PerCP (BD Pharmingen) antibodies. The methods of cell staining & sorting and recovering sorted cells have been described above (see Section 1.3.3.1.1 and 1.3.3.1.2).

Figure 4:
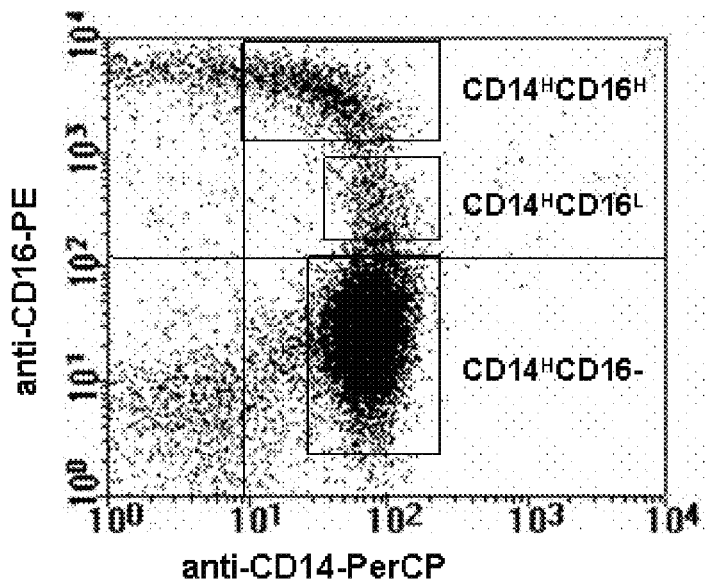
FIG. 4. A FACS profile of CD16 and sorting gates for different populations of $CD14^+$ cells isolated by CD14 magnetic beads (MACS).

The stained samples were analysed using a FACS. At least 20,000 gated events were analysed. Approximately 86% of the total cells positively selected for CD14 using MACS beads were positive for CD14. The CD14$^+$ population was further separated into three groups based on expression of CD16: CD14$^H$CD16$^-$ representing majority of the CD14$^+$ cells; minority population of CD14$^H$CD16$^L$ and CD14$^H$CD16$^H$ cells. The cell purity in the fractions exceeded 98% for CD14$^H$CD16$^-$, 96% for CD14$^H$CD16$^L$ and 92% for CD14$^H$CD16$^H$. After setting appropriate sorting gates, the following cell populations were collected: CD14$^H$CD16$^-$, CD14$^H$CD16$^L$ and CD14$^H$CD16$^H$ cell fractions. FIG. 4 shows a FACS profile of CD14 enriched samples labelled with mouse anti-human CD16-PE and mouse anti-human CD14-PerCP.

The methods of cell sorting and purification of CD14$^+$ cells from spleen tissues were essentially the same as for those from peripheral blood samples, except a fewer numbers of each cell population were obtained.

1.3.3.2. Isolation of CD5 Positive (Antigen-Experienced) B Cells and Cd5 Negative (Naïve) B Cells from Human Umbilical Cord Blood Mononuclear cells were prepared from umbilical cord blood samples as described in Section 1.3.1. Fluorescence-cell staining followed by cell sorting was performed within 4 hours of the isolation of mononuclear cell population. In this particular example, sorting of CD5 negative (naïve) B cells and CD5 positive (antigen-experienced) B cells from human umbilical cord blood, was carried out using a mouse anti-human CD5-FITC antibody (BD Pharmingen), a mouse anti-human CD19-PE antibody (BD Pharmingen) or appropriate isotype control according to the method described previously (Section 1.3.3.1.1).

Figure 5:
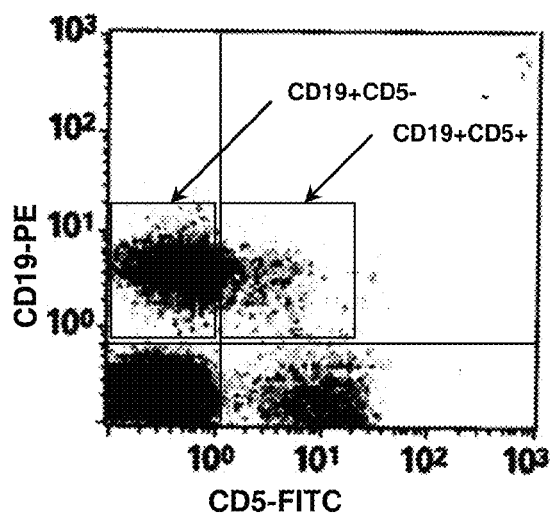
FIG. 5. A FACS profile of umbilical cord blood mononuclear cells stained with mouse anti-human CD19 and mouse anti-human CD5 antibodies.

The stained samples were analysed using a FACS. At least 20,000 gated events were analysed for each sample. After setting appropriate sorting gates for CD5 negative B cell population (CD19$^+$CD5$^-$) or for CD5 positive B cell population (CD19$^+$CD5$^+$) population, a number of fractions were collected. FIG. 5 shows a typical profile of the samples stained with mouse anti-human CD19 and mouse anti-human CD5.

The percentage of B cells in the sample ranged from 4 to 19.2% and CD5$^+$ B cells ranged from 0.8 to 7.2% of total circulated lymphocytes.

Figure 6:
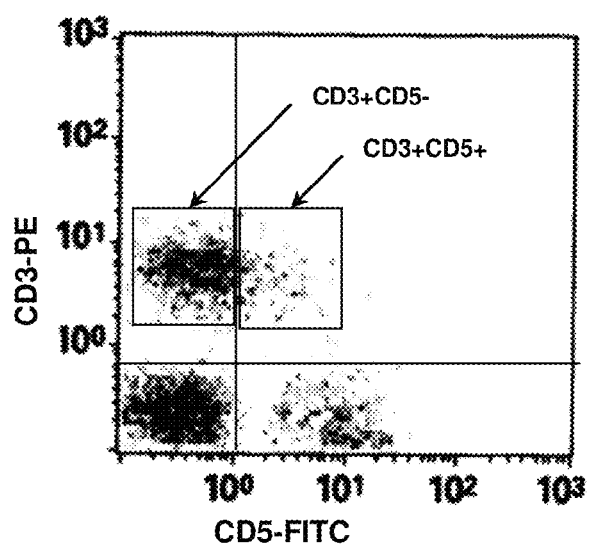
FIG. 6. A FACS profile of mononuclear umbilical cord blood cells stained with mouse anti-human CD3 and mouse anti-human CD5 antibodies.

1.3.3.3. Isolation of CD5 Positive (Antigen-experienced) T Cells and Cd5 Negative (Naïve) T Cells from Human Umbilical Cord Blood Mononuclear cells were extracted from umbilical cord blood samples using a similar method as described in Section 1.3.1. Fluorescence-cell staining followed by cell sorting was performed within 4 hours of the isolation of mononuclear cell population. In this particular example for sorting of CD5 positive (antigen-experienced) T cells and CD5 negative (naïve) T cells from human umbilical cord blood, was carried out using a mouse anti-human CD5-FITC antibody (BD Pharmingen), a mouse anti-human CD3-PE antibody (BD Pharmingen) or appropriate isotype control according to the method of cell described previously (Section 1.3.3.1.1). The stained cells were analysed using a FACS. At least 20,000 gated events were analysed. The sorting gates were set to collect fractions containing either CD5 negative T cells (CD3$^+$CD5$^-$) or CD5 positive T cells (CD3$^+$CD5$^+$). FIG. 6 shows a typical profile of the samples stained with mouse anti-human CD3 and mouse anti-human CD5 antibodies.

Recovering and Analysing Sorted Populations

Effectively, the same method used to recover and analyse the sorted populations has been described in Section 1.3.3.1.2.

The percentage of T cells in the samples ranged from 1.7 to 13.5% and CD5$^+$ T cells ranged from 0.4 to 1.3% of total circulated lymphocytes.

Figure 7:
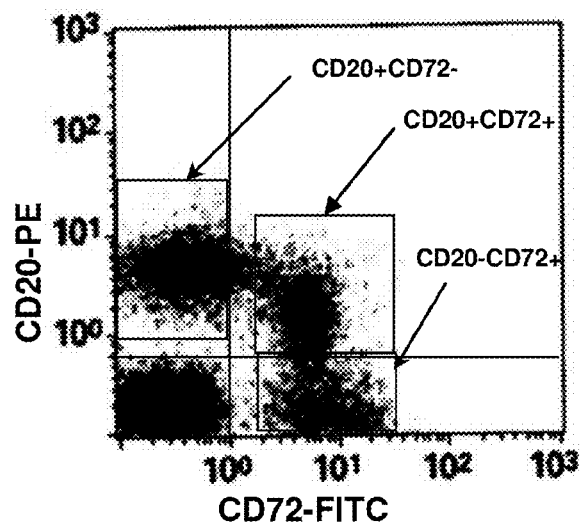
FIG. 7. A FACS profile of bone marrow mononuclear cells stained with mouse anti-human CD20 and mouse anti-human CD72 antibodies.

1.3.3.4. Isolation of Early B Cells, Activated and Resting B Cells Based on CD 20 and CD 72 Expressions from Human Bone Marrow Mononuclear Population Mononuclear cells were extracted from bone marrow using the method described previously (Section 1.3.1). The fluorescence-cell staining followed by cell sorting was performed within 4 hours of the isolation of mononuclear cell population. Staining and sorting the activated B cells is described previously in Section 1.3.3.1.1. Specifically, 10 μl of a mouse anti-human CD72-FITC antibody (BD Pharmingen) and 20 μl of a mouse anti-human CD20-PE antibody (BD Pharmingen) or appropriate isotype control (PE mouse IgG2b,κ antibodies) were used. The stained cells were analysed using a FACS. The sorting gates were set to collect fractions containing either CD20 positive population comprising pre-B cells, resting and activated B cells, follicular dendritic cells (CD20$^+$CD72$^-$) or CD72 positive cell population comprising early B cells (CD20$^-$CD72$^+$) or activated B cells (CD20$^+$CD72$^+$). FIG. 7 represents a typical profile of the samples stained with mouse anti-human CD20 and mouse anti-human CD72 antibodies.

Recovering and Analysing Sorted Populations

Effectively, the same method as described in Section 1.3.3.1.2 was applied to recover and analyse sorted cells.

Typically, approximately 10-15% of bone marrow mononuclear cell population was positive for both CD20 and CD72; 9-12% of cells were positive for CD20 but negative for CD72; and approximately 8% were positive for CD72 only.

1.3.3.5. Isolation of Thymocyte Subpopulations by Magnetic Bead Sorting

Using the MACS CD4 Multisort kit (Miltenyi Biotec GmbH), CD4$^-$CD8$^-$ double negative thymocytes, CD4$^+$CD8$^+$ double positive thymocytes, and CD4$^+$ and CD8$^+$ single positive thymocyte cell populations were sorted out according to the manufacturer's instructions. Briefly, thymocytes collected using a similar method as that described in Section 1.3.2 were incubated with CD4 Multisort CD4 microbeads for 30 minutes. After washing with 5 mM EDTA and 0.5% BSA in PBS, the labelled cells were separated on magnetic columns. The positively selected thymocytes, which were retained on the magnetic column, contained $CD4^+$ single positive and $CD4^+CD8^+$ double positive cell populations, whereas the CD4 depleted cell population, which was eluded through the column, contained $CD8^+$ single positive and $CD4^-CD8^-$ double negative cells. To remove microbeads from the CD4 positively selected cell populations, the cells were incubated with MACS Multisort release reagent. After 20 minutes, the digestion was stopped, and the cells were labelled for 30 minutes with CD8 microbeads. The $CD4^+CD8^+$ double positive thymocytes were obtained by positive selection, whereas $CD4^+$ single positive cells were found in the depleted cell population. The CD4 depleted cell population was incubated for 30 minutes with CD8 microbeads. After applying labelled cells on a magnetic column, $CD8^+$ single positive cells could be separated from the $CD4^-CD8^-$ double negative thymocytes. The purities of the four different thymocyte subpopulations were evaluated by flow cytometric analysis. The accepted purity was more than 95%.

1.3.3.6. Isolation of $CD54^+$ T Cells from Human Tonsils.

Figure 8:
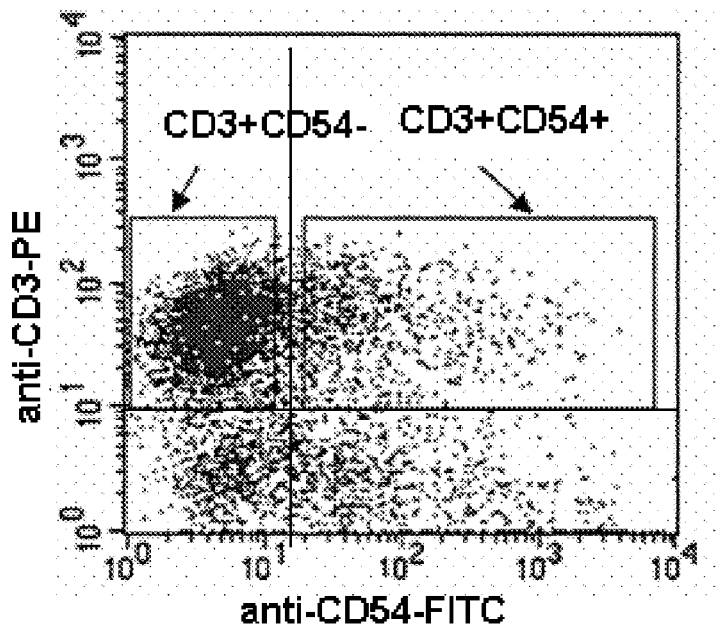
FIG. 8. A typical FACS profile of tonsillar mononuclear cells for CD3 and CD54.

Mononuclear cells were extracted from human tonsils using the method described in Section 1.3.2. The fluorescence-cell staining followed by cell sorting was performed within 4 hours of the isolation of the mononuclear cell population. $CD54^+$ T cells (intercellular adhesion molecule-1 or ICAM-1) were extracted from the mononuclear tonsillar cell population, using a mouse anti-human CD3-PE antibody (BD Pharmingen) and a mouse anti-human CD54-FITC antibody (BD Pharmingen) or an appropriate isotype control were chosen using the cell staining/sorting method as described in Section 1.3.3.1.1. The stained cells were analysed using a FACS. The sorting gates were set to collect fractions containing either $CD3^+$ T cells (i.e. $CD3^+CD54^-$ cells) or activated $CD54^+$ T cells (i.e. $CD3^+CD54^+$ cells). FIG. 8 shows a FACS profile of the samples stained with mouse anti-human CD3 and mouse anti-human CD54 antibodies. The $CD3^+$ cells were used for the creation of a cross lineage tri-hybrid, whereas $CD54^+$ activated T cells were used for expression experiments.

The results showed that whilst T cells constituted the majority (82%) of mononuclear cells isolated from tonsils, only 9% were $CD54^+$ T cells.

1.3.4 Isolation of Mouse Mononuclear Cells 8-12 week old BALB/c mice were maintained in the specific pathogen-free animal facilities. Prior to tissue extraction the mice were euthanized by $CO_2$ exposure. Peripheral blood was obtained by axillary or femoral artery puncture and collected in heparin-coated tubes. The isolation of mononuclear cell population was performed using the same protocol as described in Section 1.3.1 for isolation of human peripheral blood mononuclear cells. Mouse spleens were mechanically disrupted and mononuclear cells were isolated using procedure for isolation of human splenic mononuclear cells as described in Section 1.3.2.

1.3.5. Isolation of Lineage Specific Primary Cells from Mouse Mononuclear Cells

Mouse cells of T lymphoid lineage and myeloid lineage were isolated by standard procedures using FACS analysis and cell sorting or magnetic cell sorting. Non-limiting examples of cell staining and sorting for the isolation of lineage specific primary mouse cells are given below.

1.3.5.1. Isolation of Effector T Cells from Mouse Spleens and Peripheral Blood

The selections of different effector T cells were based on the surface expressions of CD4 and CD8.

10 µl of each of mouse anti-mouse CD4-PE antibody (BD Pharmingen) and rat anti-mouse CD8-FITC antibody (BD Pharmingen) or appropriate isotype control were added to a 100 µl aliquot of either spleen or peripheral blood mononuclear cells in staining medium (PBS+5% BSA), containing $1 \times 10^5$ cells per aliquot. For a given aliquot of mononuclear cell population, the staining mixture was incubated for 30 minutes on ice. 10 ml of ice-cold staining medium were added to the staining mixture and centrifuged for 7 minutes at 350 g and 4° C. The supernatant was aspirated and then the cell pellet was resuspended by flicking the tube in which a comparable volume of ice-cold staining medium was added. The stained cells were centrifuged and washed once more in ice-cold staining medium. The process was repeated for other aliquots. The stained cells were analysed using a FACS. At least 20,000 gated events were analysed for each sample. The typical FACS profiles of staining mouse peripheral blood and spleen mononuclear cells are shown in FIGS. 45(*a*) and 45(*b*), respectively. Both lymphoid tissues contained single positive CD4 or CD8 T cells and double positive T cells but varied in cell representation. For example, the largest population in peripheral blood contained $CD8^+CD4^-$ cytotoxic T cells (43%), whereas mononuclear spleen cells were mainly represented by $CD4^+CD8^-$ helper or regulatory T cells (42%). After setting appropriate sorting gates for CD4 positive population (region R1), for CD8 positive population (region R3) or double positive cell population (region R2), the fractions were collected. 1 ml of each fraction was collected for purity analysis and the rest of each fraction was re-suspended in complete medium for further experiments. The purities for each fraction were above 98%.

1.3.5.2. Isolation of Monocytes from Mouse Peripheral Blood

Mouse monocytes were isolated from peripheral blood mononuclear population by using negative selection with magnetic beads (Miltenyi Biotec). The mononuclear cells were suspended in magnetic cell sorting buffer (PBS, 01% wt/vol BSA, and 0.5 mM EDTA and incubated with a mixture of antibody MicroBeads including antibodies against T cells (CD90), B cells (B220), and NK cells (CD49b) according to the manufacturer's protocol. The cells were then run through a LD-negative selection column. The negative (monocyte) fraction was collected. To determine purity, the cells were stained with PE conjugated antibodies to CD11b and FITC conjugated antibodies to CD90, B220, CD49b, NK1.1 and Ly6G (BD Pharmingen). The monocytes were identified as $CD11b^+CD90^-B220^-CD49b^-NK1.1^-Ly6G^{-/(low)}$ and the purity profile was confirmed by FACS. The purity profile of mouse monocyte population is shown in FIG. 46. 100% of cells were positive for CD11b whilst more than 98% of them were negative for B220, CD90, CD49b, and NK1.1. Approximately 38% of CD11b positive cells expressed Ly6G at low levels.

EXAMPLE 2

2. Generation of Primary Cells Secreting Desired Proteins

The methods used for generating primary human cells that secrete desired proteins are given in the following Sections. These cells were either used for cell hybridisation experiments or as controls in analytical experiments or as a reference for analysis of proteins expressed in tri-hybrid expression system.

2.1. Generation of Lymphocytes Secreting Human GM-CSF

Umbilical cord blood lymphocytes were first separated by gradient density centrifugation as described in Section 1.3.1 and then activated in culture with phytohaemagglutinin (PHA) followed by cell expansion in IL-2 (1000 U/ml). The production of human GM-CSF was analysed by ELISA. The concentrations from the production ranged between 15 to 40 ng/ml/$10^6$ cells.

A total of 300,000 PHA-activated human lymphocytes were incubated in the dark with mouse anti-human CD4 antibody conjugated with FITC (Sigma) at concentrations according to the manufacturer's instructions for 30 min at 4° C. The activated human T cells were analysed and selected using a FACS (FACS VantageSE, BD). FIG. 42 (*a*) shows a typical profile of CD4+ T cells in PHA-activated lymphocyte cultures, where FIG. 42 (*b*) shows purity of 100% for CD4+ sorted cells.

2. 2. Generation of Human Lymphocytes Secreting IgM and IgG

Purified B cells (see Section 1.3.3.1) were seeded at 3.75× $10^5$ cells/ml in wells of 96 round bottom well plates (Corning) coated with mouse anti-human CD154 antibody (BD Pharmingen). The cells were cultured in complete RPMI1640 medium supplemented with 10% heat inactivated ultra-low IgG FBS (Gibco/BRL) and 100 U/ml interleukin 4 (IL-4) (R&D systems) and 50 ng/ml interleukin 10 (IL10) added after day 3 in the culture. The cultures were replenished by replacing half of the culture medium every 2 to 3 days. Cell viability and counts were evaluated in triplicate by trypan blue exclusion using hemocytometer. At day 5 and day 10, cultured lymphocytes were harvested, washed twice in PBS and analysed by FACS using mouse anti-human CD19-PE, mouse anti-human IgM-FITC or mouse anti-human IgG-FITC antibodies (all from BD Pharmingen). All stainings were achieved with 1 µg of each antibody per 1×$10^6$ cells at 4° C. In all analysis, more than 95% of cells were double-negative with markers set according to isotype-matched negative control staining. The regions containing dead cells and debris were excluded from analysis. All analyses were done by gating 5000 to 10000 living cells.

Figure 9:
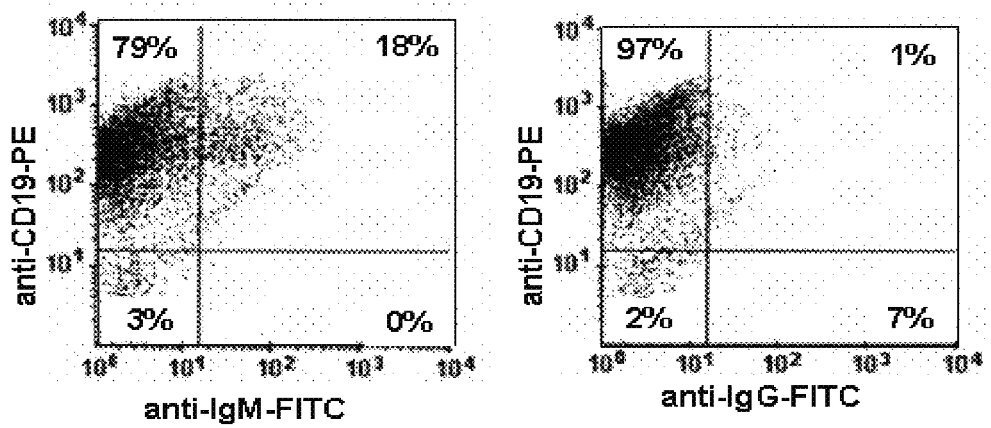
FIG. 9. Identification of IgM and IgG positive cultured lymphocytes.
Figure 9:
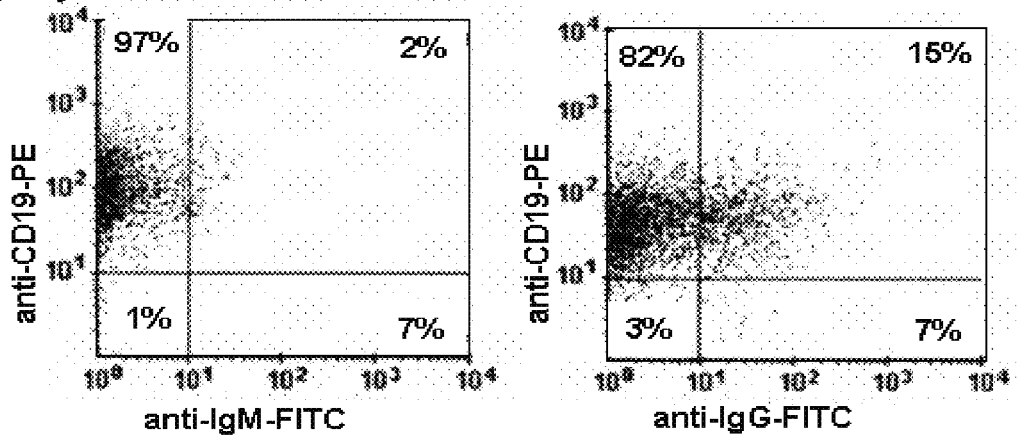

Typical profiles of IgM and IgG positive cells in the cultured lymphocytes are shown in FIG. 9. After 5 day in the culture 18% of CD19+ cells were IgM positive and only 1% had detectable IgG on the surface, whereas after 10 days the percentage of IgM positive lymphocytes reduced to only 2% whilst the percentage of IgG positive cells increased to 15%. After setting appropriate gates the IgM positive and IgG positive fractions were sorted out for Ig expression experiments.

IgM and IgG concentrations in the culture were determined by a standard ELISA using 96 ELISA well plates and plastic-absorbed goat-affinity-purified antibodies to human µ and γ chains. The bound antibodies were revealed with HRP-conjugated sheep anti-human Ig antibodies. All antibodies were from Sigma. ABTS was used as a substrate and optical densities were measured at 405 nm. Table 1 summarises the levels of IgM and IgG detected in the B lymphocyte culture after 5 and 10 days.

TABLE 1

| Period in culture | IgM, ng/$10^6$ cells | IgG, ng/$10^6$ cells |
|---|---|---|
| 5 days | 2480 ± 182 | 850 ± 92 |
| 10 days | 1215 ± 260 | 1914 ± 101 |

The production of IgM declined after 5 day in the culture whereas IgG production increased.

EXAMPLE 3

3. Somatic Cell Hybridisation

Several methods of somatic cell hybridisation are well known in the art. These include but are not limited to, for example, a biological method using fusagenic virus such as Sendai virus (Kohler and Milstein, 1975), a chemical means using polyethylene glycol (PEG) (Wojciersyn, et al, 1983), and an electrical method using electric fields (Neil, and Zimmermann, 1993). Each method can induce or cause the plasma membranes of cells of interest to be reversibly permeable and to hybridise.

Regardless of cell hybridisation methods mentioned above, two essential steps are, in principle, required in order to achieve cell hybridisation. First, the plasma membranes of the cells to be hybridised must be brought into good cell membrane contact. Second, a reversible breakdown of the plasma membranes at the point of contact must be simultaneously induced.

For the electrical cell hybridisation method, the cells of interest can be brought into good cell membrane contact by using an alternating-current electric field (AC field) with an appropriate field frequency and then be induced to hybridise when they are exposed to a short electric pulse simultaneously with the AC field.

To elaborate further, the electrical cell hybridisation involves the following physical phenomena; dielectrophoresis (DEP) and an electrical breakdown of the plasma cell membranes.

Dielectrophoresis (Pohl, 1978) is a phenomenon which describes the movement of dielectric particles such as biological cells when they are suspended in an appropriate solution and subject to a non-uniform AC electric field of an appropriate frequency. It is well documented that the movement of cells can be described as a (i) translation or migration of dielectric particles, for example at field frequencies between 0.5-2.0 megahertz (MHz) for Sp2 cells suspended in 100 mM sorbitol (Mahaworasilpa, 1992) and (ii) rotation of dielectric particles (Mahaworasilpa, 1992), for example at field frequencies between 2-10 kilohertz (kHz) for Sp2 cells suspended in 100 mM sorbitol. A non-uniform field can be generated by applying an electric field across a pair of electrodes, for instance, electrical, cylindrical wires that can be arranged in a number of configurations. The configuration most widely used is a parallel electrode configuration (FIG. 58). In the presence of a non-uniform field, DEP can cause dielectric particles (i.e. biological cells) to attract one another and simultaneously migrate towards the regions of the most intense field. As a result, it forms a chain or string of cells and, in turn, it induces good cell membrane contact. It is evident that the mutual attraction of cells is strongly promoted when the cells are suspended in solutions of moderately low electrical conductivity.

The electrical breakdown of cell membranes can be induced when the cells suspended in a suitable hybridisation solution are exposed to an electric pulse with an appropriate pulse amplitude and width (Zimmermann, 1982). A range of pulse widths, for example, square pulses of 1 to 200 microseconds (pee) is widely used, depending upon the types of cells to be hybridised.

3.1. Electrical Cell Hybridisation System

In certain embodiments of this invention, an electrical cell technique may be used to create hybridised cells, such as tri-hybrids.

3.1.1. Cell Manipulation System

In order to manipulate individual cells of interest prior to cell hybridisation, the single-cell manipulation/delivery system described previously (Section 1.1.1) was used throughout this invention.

3.1.2. Microelectrodes

In this invention two L-shape microelectrodes were used. FIG. 57 shows a microelectrode which was made of an uncoated nickel alloy, 128 µM in diameter (7). The shaft of the microelectrode was covered with a haematocrit capillary tube, 1.5 mm outer diameter (8). The L-shape Section of the microelectrode (9 and 10) was configured to allow a consistent area of the surface of both the horizontal and vertical Sections of the electrode to be exposed to a medium or an appropriate solution (Mahaworasilpa, 1992). Prior to the cell hybridisation process, two microelectrodes were mounted on two fine micromanipulators, one for each microelectrode. These microelectrodes were arranged in such a way that a parallel electrode configuration of each electrode was obtained (FIG. 58). Each fine micromanipulator was hydraulically driven and allowed movement as fine as 0.5 µm to be made in the X, Y or Z direction.

3.1.3. Cell Chamber and Configuration

FIG. 59 shows two parallel electrodes in a well of a standard 96-well TC plate, the well serves as a cell hybridisation chamber in certain embodiments of this invention. To perform cell hybridisation the microelectrodes were submerged in an appropriate medium (11) contained with the well (12) of a standard 96-well tissue culture plate. FIG. 60 and FIG. 61 show a top view and a lateral-view of the parallel electrode configuration respectively, where, for example three pre-selected cells to be hybridised are placed in between the parallel electrodes in such a way that they can be induced to align or form a chain of cells in the presence of an appropriate AC electric field.

EXAMPLE 4

4. Examples of Cross-lineage Tri-hybrid Productions by Electrical Cell Hybridisation Method The following Sections provide examples of the creation of tri-hybrid cell lines obtained by hybridising cells from either different lineages or cell types or same lineages/or cell types but different phenotypes. Each stable tri-hybrid underwent analysis to confirm that it simultaneously possessed phenotypic characteristics of parent cells. The confirmation was based on the analysis of lineage specific cell surface markers, intracellular expression of lineage specific markers, presence of RNA transcripts of lineage specific markers, karyotyping, and/or secretion of lineage specific proteins. The examples below illustrate the most typical phenotypic characteristics of cross-lineage tri-hybrids. However, these examples are in no way limited to a particular marker chosen.

4.1. Cross-lineage Tri-hybrid Production from Three Immortal Cells Derived from Myeloid, T and B Lymphoid Lineages—KMW.

This type of cross-lineage tri-hybrid was created by hybridising one myeloid K562 cell, one T lymphoid MOLT4 cell and one B lymphoid WIL2NS cell. The cross-lineage tri-hybrid so obtained was labelled as a KMW line (followed by its serial number). The following steps for the process of KMW cross-lineage tri-hybrid production, the solutions (hybridisation, culture and recovery media) and the parameters used in this invention are described below.

4.1.1. Cell Preparation for KMW Cross-Lineage Tri-hybrid Production

K562, WIL2NS, and MOLT4 cell lines were cultured in our standard medium (see Section 1.1). As a routine, each cell line was passaged every 3 days. Prior to cell hybridisation, the stable clone of each cell type which had the highest proliferation rate was established using the procedure described in Section 1.1.2. In some experiments, $CD71^+$-enriched cell populations established as described in Section 1.1.3 were used. Also, on some occasions, the $CD15^+$ cells of $CD71^+$-enriched K562 population (Section 1.1.3.1) were used.

4.1.2. Cell Hybridisation Protocol for KMW Cross-lineage Tri-hybrid Production

A few wells of a TC 96-well plate were used as cell hybridisation wells. Each well was filled with approximately 150 µl of hybridisation medium, which consisted of 240 mM sorbitol (Sigma), 2.0 mM $KH_2PO_4$ (Sigma), 0.4 mM $CaCl_2$ (Sigma), 0.2 mM $Mg(C_2H_3O_2)_2$ (Sigma) and 0.2 mM $Ca(C_2H_3O_2)_2$ (Sigma), supplemented with 0.2% bovine serum albumin, BSA (Sigma). Prior to electrical cell hybridisation, the cells of the pre-selected clone of each cell type were washed once in a hybridisation medium for a few minutes and transferred to a well containing the fresh hybridisation medium. The well was designated as a pre-hybridisation well. Before the cell hybridisation process, a single and washed cell of each selected clone was manipulated according to Section 1.1.1 such that only three cells, one from each selected clone, were positioned in between a pair of identical, parallel electrodes, which was submerged to the bottom of the well (as shown in FIG. 61). The separation of the electrodes was set at 400 micrometres (i.e. 400 µm).

To achieve electrical cell hybridisation, firstly, an alternating current (AC) field with a frequency of 0.8 MHz and a field strength of circa 50-60 kilovolts per meter (e.g. 50-60 kV/m) was applied between the electrodes for a few seconds until the three cells were induced to attract to one another by dielectrophoresis, DEP, and form a string of cells. This process caused the cells to make good cell membrane contact. The cells were arranged in such a way that K562 cell was in the middle of the cell alignment (see FIG. 60 or 61). Then, two electric square pulses, with an interval of 3 seconds between the pulses, were applied simultaneously with the AC field. Each pulse with an intensity of circa 170 kV/m and a pulse width of 75 micro-seconds (e.g. 75 µsec) was used. After the completion of the second square pulse, the AC field was kept on continuously for another 5 seconds, resulting in cell hybridisation into a single cross-lineage tri-hybridised cell. For certain embodiments of this invention, it was observed that hybridisation of the three cells might not take place simultaneously, i.e. hybridisation of two out of the three cells frequently occurred first followed by the hybridisation of the third cell. In some cases an additional square pulse was required to obtain a complete three-cell hybridisation. The newly created cross-lineage tri-hybrid cell was then transferred from the hybridision well to a recovery well, which was located in a different row from that of the hybridisation wells. Each recovery well contained 150 µl standard TC medium (see Section 1.1). Each newly established cross-lineage tri-hybrid cell was incubated, one cross-lineage tri-hybrid cell per recovery well, in a humidified incubator, operated at 37° C. and 5% $CO_2$ content, for seven days. Most of the cross-lineage tri-hybrids were found to divide within 36 hours after the cell hybridisation event. At the end of the incubation period, the medium in each recovery well was appropriately replenished with fresh standard medium. This stimulated cell proliferation of each cross-lineage tri-hybrid clone. Two or three days later dividing or surviving cells were identified from each recovery well and were plated into the wells of a standard 24-well TC plate, giving rise to a set of cross-lineage tri-hybrid clones. Each cross-lineage tri-hybrid clone was cultured in the 24-well plate for another week before being transferred into a 25 $cm^2$ TC flask, containing 10 millilitres (ml) of our standard culture medium (see Section 1.1) and being labelled appropriately for further analysis. The entire process of electrical cell hybridisation and cross-lineage tri-hybrid recovery process was repeated for a number of times in order to create a batch of stable cross-lineage tri-hybrid cells.

4.1.3. Confirmation of KMW Cross-lineage Tri-hybrid Status Expressions of CD Markers An example of the verification of an established KMW cross-lineage tri-hybrid cell line is given below.

After a KMW cross-lineage tri-hybrid cell line had been established under normal culture conditions for 6 months, the cross-lineage tri-hybrid cell population was analysed for the expression of lineage specific CD markers.

A tri-colour FACS analysis was utilised to verify co-expressions of the following CD markers: CD19 originating from WIL2NS, CD15 originating from K562 and CD4 originating from MOLT4.

In brief, 100 μl of KMW cross-lineage tri-hybrid cells at concentration of $1\times10^6$ cells/ml in PBS containing 5% BSA were suspended in 100 μl of PBS and incubated for 30 min at 4° C. with 0.5 mg/100 ml mouse anti-human CD15-PerCP, 0.25 mg/100 ml mouse anti-human CD4-PE and 1.0 mg/100 ml mouse anti-human CD19-FITC antibodies or an appropriate isotype control. All mouse anti-human antibodies were acquired from BD Pharmingen. After extensive washing with PBS, the labelled cells were analysed using FACSCalibur flow cytometer and CellQuest Pro software.

FIG. 10 shows FACS profile of the KMW cross-lineage tri-hybrid cell line, which suggests that the KMW cross-lineage tri-hybrid cells, where lineage specific characteristics come from immortal phenotypes, contain heterogeneous cell populations of mixed phenotypes, with myeloid being predominant. However, 62% of KMW cells shared myeloid and T lymphoid phenotypes and 28% of KMW cells express T and B lymphoid phenotypes.

4.2. Cross-lineage Tri-hybrid Production from One Immortal Myeloid and Two Primary Lymphoid Cells—KBT The cross-lineage tri-hybrid was created by somatic cell hybridisation of one myeloid K562 cell, one primary human B cell and one primary human T cell. The cross-lineage tri-hybrid was dubbed KBT followed by serial number.

4.2.1. Cell Preparation for KBT Cross-lineage Tri-hybrid Production

The preparation of K562 cells prior to the creation of KBT cross-lineage tri-hybrid has been described previously (Section 4.1.1). The primary cells used in the creation of KBT cross-lineage tri-hybrids included (i) mature B cells ($CD19^+$) derived from spleen, peripheral blood or umbilical cord blood; early B cells ($CD20^-CD72^+$) derived from bone marrow; activated B cells ($CD20^+CD72^+$) derived from bone marrow; antigen experienced B cells ($CD19^+CD5^+$) derived from umbilical cord blood and (ii) helper T cells ($CD4^+$) derived from spleen, peripheral blood, umbilical cord blood and thymus, cytotoxic T cells ($CD8^+$) derived from spleen, peripheral blood, umbilical cord blood and thymus; antigen-experienced T cells ($CD3^+CD5^+$) derived from umbilical cord blood; $CD3^+$ T cells from umbilical cord blood; double negative T cells ($CD3^+CD4^-CD8^-$) derived from thymus, double positive T cells ($CD3^+CD4^+CD8^+$) derived from thymus were used in experiments. The isolation of various primary lymphoid cells from various lymphoid tissues has been described previously in Section 1.3.

4.2.2. Cell Hybridisation Protocol for KBT Cross-lineage Tri-hybrid Production

The cell hybridisation protocol for KBT cross-lineage tri-hybrid production is similar to that used for KMW cross-lineage tri-hybrid production (Section 4.1.2), except that the medium and the AC electric fields and pulses varied. The hybridisation medium used in these experiments consisted of 230 mM sorbitol, 1.8 mM $KH_2PO_4$, 0.5 mM $CaCl_2$, 0.2 mM $Mg(C_2H_3O_2)_2$ and 0.3 mM $Ca(C_2H_3O_2)_2$, supplemented with 0.3% BSA. An AC field of 0.5 MHz and 65-75 kV/m was applied simultaneously with a train of three square pulses at a 3-second interval, each with a pulse width of 100 μsec and strength of 175-185 kV/m. The AC field was switched on continuously for another 5 sec after the completion of the third square pulse resulting in the hybridisation of the cells to produce a cross-lineage tri-hybrid cell. The protocols for the recovery and the establishment of a stable line of this newly formed cross-lineage tri-hybrid cell were described in Section 4.1.2.

4.2.3. Confirmation of KBT Cross-lineage Tri-hybrid Status Expressions of CD Markers on Cell Surface A KBT Cross-lineage Tri-hybrid Cell Line Established from One Immortal Myeloid (K562) Cell, One Primary Mature B Cell and One Primary Effector T Helper Cell After a cross-lineage tri-hybrid cell line, for example, had been established under normal culture conditions for a few months, the cell line was analysed for the expression of lineage specific CD markers. The cells of KBT cell line were labelled with mouse anti-human CD19 and CD4 antibodies using the same protocols as described in cell preparation prior to hybridisation (Section 1.3.1.1). FIG. 11(d) shows FACS profiles (CD19 and CD4 labels) of a KBT cross-lineage tri-hybrid cell line established from one immortal myelomonocytic cell and 2 primary cells. Typically, more than 95% of cells in such a stable cross-lineage tri-hybrid expressed CD markers for both B and T cells with the density similar to that of parent, primary cells.

A KBT Cross-lineage Tri-hybrid Cell Line Established from One Immortal Myeloid Cell (K562) and 2 Primary Antigen-Experienced Lymphoid Cells (B and T Cells)

In another embodiment a KBT cell line derived from cell hybridisation of one K562 cell, one antigen-experienced B and one antigen-experienced T cell was established. The cells were analysed for co-expression of CD19, CD3 and CD5 using a FACS.

In brief, the cells were labelled with mouse anti-human CD5-FITC and mouse anti-human CD19-PE or mouse anti-human CD4-PE antibodies using the same protocols as in cell preparation prior to cell hybridisation (Section 1.3.1.1). FIG. 12 shows FACS profiles of cells of such KBT cross-lineage tri-hybrid cell line. The results show that 5-10% of KBT cell population retained its memory of antigen exposure by maintaining cell surface expression of CD5 molecule whilst being positive for CD3 or/and CD19. Also at least 83% of CD5 negative cell population co-expressed both B lineage (CD19) and T lineage (CD3) markers.

A KBT Cross-lineage Tri-hybrid Cell Line Established from One Immortal Myeloid Cell (K562), an Activated B Cell and One Primary Double Positive Uncommitted Effector T Cell In another embodiment a KBT cell line derived from cell hybridisation of one K562, one T cell (double positive for $CD4^+$ and $CD8^+$) isolated from thymus and one activated B cell ($CD20^+$ and $CD72^+$) (explained in section 1.3.34) isolated from bone marrow was established. The cells were analysed for co-expressions of CD4, CD8, CD20 and CD72 on the cell surface.

In brief, the KBT cross-lineage tri-hybrid cells were either labelled with antibody combination of mouse anti-human CD4-PE and mouse anti-human CD72-FITC antibodies or mouse anti-human CD20-PE and mouse anti-human CD8-FITC antibodies or mouse anti-human CD4-PE and mouse anti-human CD8-FITC antibodies using the same protocol as described for isolation of primary lymphocytes (Section 1.3.3.1.1). FIG. 13 shows FACS profiles of such cross-lineage tri-hybrid cells.

The results (see FIG. 13) showed that 99% of KBT cross-lineage tri-hybrid cells expressed either of double positive T cell derived CD4 or CD8 on its surface where 66-71% of cells were being positive for CD4 and 88-89% of cells were being positive for CD8. In 60% of these cells, the expression of CD4 and CD8 was concurrent. Whilst being positive for CD4 derived from double positive thymocytes, 61% of cells were also positive for CD72 derived from activated B cells of bone marrow. However, 94% of cross-lineage tri-hybrid population expressed CD72 on their surface. On the other hand, 31% of CD8 positive cross-lineage tri-hybrid cells co-expressed CD20. The total number of CD20 positive cells was 39%.

4.3. Cross-lineage Tri-hybrid Production from One Immortal Lymphoid, One Primary Lymphoid Cell and One Primary Myelomonocytic Cell—WTM Here is an example of creation of a cross-lineage tri-hybrid cell line from one immortal human B lymphoid cell (WIL2NS), one primary human T cell and one primary human monocyte. The cross-lineage tri-hybrid line was labelled as WTM followed by serial number.

4.3.1. Cell Preparation for WTM Cross-lineage Tri-hybrid Production

The preparation of WIL2NS cells used in the creation of WTM cross-lineage tri-hybrids was described previously in Section 4.1.1. The primary cells include $CD14^+CD16^-$ or $CD14^+CD16^L$ monocytes derived from spleen and peripheral blood; helper T cells ($CD4^+$) derived from spleen, peripheral blood, umbilical cord blood and thymus; cytotoxic T cells ($CD8^+$) derived from spleen, peripheral blood, umbilical cord blood and thymus; antigen experienced T cells ($CD3^+CD5^+$) and $CD3^+$ T derived from umbilical cord blood; double negative T cells ($CD3^+CD4^-CD8^-$) and double positive T cells ($CD3^+CD4^+CD8^+$) derived from thymus, were used in these experiments. The isolation of various primary lymphoid cells from various lymphoid tissues has been described previously (Section 1.3.3). In certain embodiments, $CD34^+CD15^+$ myelomonocytic progenitor cells derived from bone marrow were used instead of CD14 positive monocytes.

4.3.2. Cell Hybridisation Protocol for WTM Cross-lineage Tri-hybrid Production

The cell hybridisation protocol for WTM cross-lineage tri-hybrid production was similar to that used for KMW cross-lineage tri-hybrid production (see Section 4.1.2), except that the medium varied. The hybridisation medium used in these experiments consisted of 235 mM sorbitol, 1.8 mM $KH_2PO_4$, 0.5 mM $CaCl_2$, 0.3 mM $Mg(C_2H_3O_2)_2$, and 0.25 mM $Ca(C_2H_3O_2)_2$ (Sigma), supplemented with 0.3% BSA. The exact electrical protocol as described in Section 4.2.2 was used for the production of WTM. The protocols for the recovery and the establishment of a stable line of this newly formed cross-lineage tri hybrid cell were described in Section 4.1.2.

4.3.3. Confirmation of WTM Cross-lineage Tri-hybrid Status Expressions of CD Markers A WTM Cross-lineage Tri-hybrid Cell Line Established from One Immortal Lymphoid Cell (WIL2NS), One Primary T Cell and One Primary Monocyte A WTM cell line derived from cell hybridisation of one WIL2NS cell, one primary T cell and one monocyte was established. After the cross-lineage tri-hybrid cell line had been cultured under normal conditions (see Section 1.1) for 6 months, the cross-lineage tri-hybrid cell population was analysed for the expression of lineage specific CD markers. Tri-colour FACS analysis was utilised to verify for co-expression of CD19 originating from WIL2NS, CD14 originating from primary monocytes and CD4 originating from primary T cell when these primary T cells were used for hybridization.

In brief, 100 ml of the WTM cross-lineage tri-hybrid cells at concentration of $1\times10^6$ cells/ml in PBS containing 5% BSA were suspended in 100 μl PBS were incubated for 30 min at 4° C. with labelled monoclonal antibodies (0.5 mg/100 ml CD14-PerCP, 0.25 mg/100 ml CD4-PE, and 1.0 mg/100 ml CD19-FITC, all acquired from BD Pharmingen) or the appropriate isotype control. After extensive washing with PBS, the labelled cells were analysed using FACSCalibur flow cytometer and CellQuest Pro software.

FACS Profiles of WTM cross-lineage tri-hybrid cells are shown in FIG. 14. Whilst the levels of the expression CD19, marker which derived from immortal cell appeared to be consistent among the cross-lineage tri-hybrid cell population, the expressions of markers originating from primary cells seemed to vary. In this particular example, the cell populations can be divided into the three subgroups based on the intensity of CD14 and CD4 expressions: (i) $CD4^HCD14^L$; (ii) $CD4^HCD14^H$; (iii) $CD4^LCD14^H$. Each of these populations can be subsequently isolated by standard techniques such as FACS, MACS or single cell cloning, etc. and expanded into separate cross-lineage tri-hybrid cultures processing phenotypic characteristics different from each other whilst maintaining in-culture homogeneity.

A WTM Cross-lineage Tri-hybrid Cell Line Established from One Immortal Lymphoid Cell (WIL2NS), One Primary Antigen-experienced T Cell and One Primary Monocyte When $CD5^+$ antigen-experienced T cells were used to generate a WTM cross-lineage tri-hybrid cell line, the expression of CD5 concurrently with CD19 and CD14 was verified by using tri-colour FACS analysis. The protocol was essentially the same as for described above except mouse anti-human CD19-PE and mouse anti-human CD5-FITC antibodies were employed instead of mouse anti-human CD19-FITC and mouse anti-human CD4-PE antibodies. FACS profiles of these CD expressions on the cross-lineage tri-hybrid cells are shown in FIG. 15. The analysis showed that whilst the level of CD19 expression derived from immortal cell and responsible for B cell phenotype appeared to be consistent around 91-99% of the cell population, the expression of CD5 derived from antigen-experienced T cells and CD14 derived from primary monocytes varied among the WMT hybrid cells. Only 63% of CD19 positive cells were also positive for CD5 and 79% of CD19 positive cells were positive for CD14. Notably, the level of CD14 expression varied among such WMT cross-lineage tri-hybrid cells from low to high. On the other hand, the cell population was clearly divided on the $CD5^+$ and $CD5^-$ cross-lineage tri-hybrid cells.

A WTM Cross-lineage Tri-hybrid Cell Line Established from One Immortal Lymphoid Cell (WIL2NS), One Primary Cytotoxic T Cell and One Primary Monocyte When cytotoxic CD8 positive T cells were used to create a WTM cross-lineage tri-hybrid line, the FACS analysis was performed to verify co-expression of CD19, CD8 and CD14 using the same tri-colour labelling protocol as described earlier in this Section. FIG. 16 shows FACS profiles of CD19, CD8 and CD14 expressions on the cells of this WTM cross-lineage tri-hybrid cell line. The expression of CD19 and its level remained constant among these WMT cross-lineage tri-hybrid cells, whereas only 46% of these cells co-expressed CD8 derived from primary cytotoxic T cells at low levels and 41% co-expressed CD14 derived from primary monocyte. Notably, the level of CD14 expression among these WMT cells varied from low to high.

A WTM Cross-lineage Tri-hybrid Cell Line from One Immortal Lymphoid Cell (WIL2NS), One Primary Double Positive T Cell and One Primary Monocyte When double CD positive T cells (CD4$^+$CD8$^+$) derived from thymuses were used for the creation of a WTM cross-lineage tri-hybrid cell line, the analysis of CD4 and CD8 co-expression was utilised in addition to the analysis of CD19, CD8 and CD14 expressions. FIG. 17 shows a FACS profile for the co-expression of CD4 and CD8 on the cells of the cross-lineage tri-hybrid cell line. In this instance where double positive T cells were used, 96% of WTM cross-lineage tri-hybrid cells were positive for both CD4 and CD8. The expression profile of CD19 and CD14 on the WTM cross-lineage tri-hybrid cells derived from CD4$^+$CD8$^+$ positive T cells was essentially similar to those WTM cross-lineage tri-hybrid cells derived from cytotoxic CD8 positive effector T cells.

A WTM Cross-lineage Tri-hybrid Cell Line Established from One Immortal Lymphoid Cell (WIL2NS), One Primary T Cell and One Primary Myelomonocytic Progenitor Cell When CD34$^+$CD15$^+$ myelomonocytic cells derived from bone marrow were used to generate a WTM cross-lineage tri-hybrid cell line, the surface markers for CD19 (B lineage), CD3 (T lineage), CD15 (myeloid lineage) and CD34 (progenitor cell) were analysed. In brief, the cells of this WMT cross-lineage tri-hybrid cell line were labelled with combination of mouse anti-human CD19-PE, mouse anti-human CD4-FITC (BD Pharmingen) and mouse anti-human CD15-PerCP antibodies or with a combination of mouse anti-human CD34-PE, mouse anti-human CD4-FITC and mouse anti-human CD15-PerCP antibodies. The cell staining was performed according to the protocols described earlier (Section 1.3.3.1.1). Typical expression profiles of WTM cross-lineage tri-hybrid cells originating from CD34$^+$CD15$^+$ myelomonocytic progenitor cell are shown in FIG. 18. The analysis showed that approximately 81% of WTM cross-lineage tri-hybrid cells shared B lineage and myelomonocytic phenotypes (CD19$^+$CD15$^+$) and 61% of CD 19$^+$ were also positive for CD4, T lineage marker. 34% of CD4$^+$ cross-lineage tri-hybrid cells retained also CD34 on their surface and 68% of CD34$^+$ tri hybrid cells expressed CD15. Interestingly, 28% of CD34$^+$ cross-lineage tri-hybrid cells did not retain expression of CD15 even though both CD34 and CD15 come from the same source (myelomonocytic progenitor cell).

4.4. Cross-lineage Tri-hybrid Production from One Immortal Myeloid Cell, One Immortal Lymphoid Cell and One Primary Lymphoid T Cell.—KWT This type of cross-lineage tri-hybrid production was created by cell hybridisation of one immortal myeloid cell (K562), one immortal B lymphoid cell (WIL2NS) and one primary human T cell. The cross-lineage tri-hybrid of this kind was dubbed KWT followed by serial number.

4.4.1. Cell Preparation for KWT Cross-lineage Tri-hybrid Production

The preparations of K562 and WIL2NS cells for these cell hybridisation experiments have been described in Sections 4.1.1. Prior to cell hybridisation, a stable clone of each cell type, exhibiting the highest proliferation rate was established using the procedure described in Section 1.1.1. In certain embodiments, CD71$^+$-enriched cell populations as described in Section 1.1.3 were used. In further embodiments, CD15$^+$ cells of CD71$^+$-enriched K562 population selected as described in Section 1.1.3.1 were used. The primary cells used for the creation of KWT cross-lineage tri-hybrids included helper T cells (CD4$^+$) derived from spleen, peripheral blood, umbilical cord blood and thymus; cytotoxic T cells (CD8$^+$) derived from spleen, peripheral blood, umbilical cord blood and thymus; antigen experienced T cells (CD3$^+$CD5$^+$) and CD3$^+$ T cells derived from umbilical cord blood; double negative T cells (CD3$^+$CD4$^-$CD8$^-$) and double positive T cells (CD3$^+$CD4$^+$CD8$^+$) derived from thymus were used in these experiments (see Section 1.3)

4.4.2. Cell Hybridisation Protocol for KWT Cross-lineage Tri-hybrid Production

The cell hybridisation protocol for KWT cross-lineage tri-hybrid production was similar to that used for KMW cross-lineage tri-hybrid production (see Section 4.1.2).

4.4.3. Confirmation of KWT Cross-lineage Tri-hybrid Status Expression of CD Markers A KWT Cross-lineage Tri-hybrid Cell Line Established from One Immortal Myeloid Cell (K562), One Immortal Lymphoid (WIL2NS) and One Primary T Cell A KWT cell line derived from cell hybridisation of one K562 cell, one WIL2NS cell and one primary T cell was established. After the cross-lineage tri-hybrid cell line had been stable under normal culture conditions for 6 months, the cross-lineage tri-hybrid cell population was analysed for the expression of lineage specific CD markers. A tri-colour FACS analysis was utilised to identify for co-expression of CD15 originating from K562, CD19 originating from WIL2NS and CD4 originating from primary effector T helper cell. The protocol for cell staining of KWT cross-lineage tri-hybrid cells was essentially the same as described for KMW cross-lineage tri-hybrids (Section 4.1.3). FACS profiles of KWT cross-lineage tri-hybrid cells derived from CD4$^+$ effector T cells are shown in FIG. 19. The majority of KWT cross-lineage tri-hybrid cells demonstrated mixed phenotypic characteristics of myelomonocytic, B and T lymphoid lineages. 100% of KWT cross-lineage tri-hybrid cells expressed CD4 on the cell surface, a marker of T lymphoid lineage, which is derived from primary effector T cell, whilst 54% of these cells were simultaneously positive for B lineage marker CD19 derived from immortal cell of WIL2NS line and 24% of these CD4$^+$CD19$^+$ cells were positive for CD15 derived from immortal myelomonocytic progenitor cell line K562.

A KWT Cross-lineage Tri-hybrid Cell Line Established from One Immortal Myeloid Cell (K562), Immortal Lymphoid Cell (WIL2NS) and One Double Positive T Cell When double positive T cells (CD4$^+$CD8$^+$ cells) were used to generate a KWT cross-lineage tri-hybrid line, the expression profile of both CD4 and CD8 derived from primary thymocytes was also analysed. The protocol for CD profiling was essentially the same as described above for KWT cross-lineage tri-hybrids derived from CD4$^+$ T cells, except mouse anti-human CD8-FITC antibody was used instead of mouse anti-human CD19-FITC antibody. The typical CD expression profiles of the cross-lineage tri-hybrid cells derived from the double positive (CD4$^+$CD8$^+$) T cells are shown in FIG. 20. The results showed that 99% of KWT cross-lineage tri-hybrid cells were positive for CD4$^+$ and 69% were positive for CD8, with 26% of CD4$^+$ cells being positive for CD15 myelomonocytic cell marker and 23% of CD8$^+$ cells being positive for CD15 meaning that CD4$^+$CD8$^+$CD15$^+$ cells represented approximately 23% of the total cell population (because almost 100% of the cells are CD4$^+$, the double positive CD8$^+$CD15$^+$ population would also be positive for CD4). As in KWT tri-hybrid derived from CD4$^+$ effector T cells, the CD19$^+$ cells represented 52% of the total cell population with 22% of them co-expressing CD15. Thus, the entire CD15$^+$ cell population co-expressed CD4, CD8 and CD19 meaning 22-23%.

A KWT Cross-lineage Tri-hybrid Cell Line Established from One Immortal Myeloid Cell (K562), Immortal Lymphoid Cell (WIL2NS) and CD5 Positive Antigen-experienced T Cell When CD5 positive antigen-experienced T cells were used to generate a KWT cross-lineage tri-hybrid line, the expression of CD5 was analysed. The KWT hybrid cells were labelled with mouse anti-human CD19-HTC and mouse anti-human CD5-PE antibodies using the same protocol as used for analysis of WTM cross-lineage tri-hybrids except for reversion of fluorescent conjugates between mouse anti-human CD19 and mouse anti-human CD5 antibodies (Section 4.6). The results shown in FIG. 21 showed that 90% of the KWT cross-lineage tri-hybrid cells were positive for CD5 originating from antigen-experienced T cell and 49% of the CD5 cells were also positive for CD19 originating from WIL2NS cells (B cells). The total percentage of CD19$^+$ cells among the cross-lineage tri-hybrid cells was around 56%.

4.5. Cross-lineage Tri-hybrid Production from Two Immortal Lymphoid Cells (WIL2NS) and One Primary Monocyte—WWM This type of cross-lineage tri-hybrid production was created by somatic cell hybridisation of two immortal lymphoid cells (WIL2NS) and one primary human monocyte. The cross-lineage tri-hybrid was labelled as WWM followed by serial number.

4.5.1. Cell Preparation for WWM Cross-lineage Tri-hybrid Production

WIL2NS cell line was cultured in the same procedure as described in Section 4.1.1.

In certain embodiments, CD71$^+$-enriched cell populations established as described in Section 1.1.3 were used. Human monocytes were isolated from mixed lymphocytes sourced from spleen, peripheral blood or umbilical cord blood. The isolation of monocytes was based on the expression of CD14 marker and in some instances low levels of CD16 expression either FACS or magnetic beads as described earlier in Section 1.3.3.1.1. There appeared to be no difference in hybridisation parameters or resulting cross-lineage tri-hybrids when monocytes from different lymphoid tissues were used.

4.5.2. Cell Hybridisation Protocol for WWM Cross-lineage Tri-hybrid Production

The cell hybridisation protocol for WWM cross-lineage tri-hybrid production was similar to that used for KBT cross-lineage tri-hybrid production (see Section 4.2.2).

4.5.3. Confirmation of WWM Cross-lineage Tri-hybrid Status

Expression of CD Markers

After a WWT cross-lineage tri-hybrid cell line had been stable under normal culture conditions (see Section 1.1) for 6 months, the cross-lineage tri-hybrid cell population was analysed for the expression of lineage specific CD markers.

Double staining or labelling with mouse anti-human CD19-FITC and mouse anti-human CD14-PE antibodies was applied to profile cross-lineage marker expression of the resulting cross-lineage tri-hybrid. FIG. 22a shows a typical CD profile of such cross-lineage tri-hybrid cells. The expression of oncogene-linked marker CD19 appeared to be constant in the cross-lineage tri-hybrid cells. Whilst some proportion of the cells (23.5%) did express CD14 on their surface, the remaining 72.7% were negative for surface expression of CD14.

4.6. Cross-lineage Tri-hybrid Production Using Non-human Mammalian Cells

The following example indicates that cross-lineage tri-hybrids can be created using mammalian cells other than human cells, specifically mouse cells. It is understood that the same principle can be applied in generating cross-lineage tri-hybrids from other mammalian cells.

4.6.1. Cross-lineage Tri-hybrid Production from One Immortal Mouse Lymphoid Cell, One Primary Mouse Lymphoid Cell and One Primary Mouse Monocyte This Section describes the creation of a cross-lineage tri-hybrid cell line from one immortal mouse B lymphoid cell (Sp2), one primary mouse T cell and one primary mouse monocyte. The cross-lineage tri-hybrid line was labelled as STmMm followed by a serial number.

4.6.1.1. Cell Preparation for STmMm Cross-lineage Tri-hybrid Production

The preparation of Sp2 cells used in the creation of STmMm cross-lineage tri-hybrids was described previously in Section 1.1.4 The primary mouse cells including CD11b$^+$CD90$^-$B220$^-$CD49b$^-$NK1.1$^-$Ly6G$^{-/low}$ monocytes derived from peripheral blood; mouse helper T cells (CD4$^+$) derived from spleen or peripheral blood; mouse cytotoxic T cells (CD8$^+$) derived from spleen or peripheral blood; and double positive T cells (CD4$^+$CD8$^+$) derived from spleen or peripheral blood, were used in these experiments. The isolation of various primary mouse lymphoid cells from spleen and peripheral blood has been described previously (Section 1.3.5).

4.6.1.2. Cell Hybridisation Protocol for STmMm Cross-lineage Tri-hybrid Production The cell hybridisation protocol for STmMm cross-lineage tri-hybrid production was similar to that used for WTM cross-lineage tri-hybrid production (see Section 4.3.2), except that the medium and the AC electric fields and pulses varied. That is the hybridisation medium used in these experiments consisted of 265 mM sorbitol, 1.5 mM KH$_2$PO$_4$, 0.4 mM CaCl$_2$, and 0.3 mM Mg(C$_2$H$_3$O$_2$)$_2$ (Sigma), supplemented with 0.2% BSA. An AC field of 0.5 MHz and 65-75 kV/m was applied simultaneously with a train of three square pulses at a 3-second interval, each with a pulse width of 70 μsec and strength of 250-280 kV/m. The protocols for the recovery and the establishment of a stable line of this newly formed cross-lineage tri-hybrid cell were described in Section 4.1.2.

4.6.1.3. Confirmation of STmMm Cross-lineage Tri-hybrid Status

A STmMm cell line derived from cell hybridisation of one Sp2 cell, one primary mouse T cell and one mouse monocyte was established. After the cross-lineage tri-hybrid cell line had been cultured under normal conditions (see Section 1.1) for 6 months, the cross-lineage tri-hybrid cell population was analysed for the expression of lineage specific CD markers. Tri-colour FACS analysis was utilised to verify for co-expression of CD138 originating from Sp2 cells, CD11b originating from primary mouse monocytes and CD4 originating from primary mouse T cell when these primary T cells were used for hybridization.

In brief, 100 μl of the STmMm cross-lineage tri-hybrid cells at concentration of 1×10$^6$ cells/ml in PBS containing 5% BSA were suspended in 100 μl PBS and were incubated for 30 mM at 4° C. with labelled rat monoclonal antibodies to mouse CD138-PE, CD11b-FITC and CD4-PerCP (BD Pharmingen) or the appropriate isotype control. After extensive washing with PBS, the labelled cells were analysed using FACSCalibur flow cytometer and CellQuest Pro software.

FACS Profiles of STmMm cross-lineage tri-hybrid cells are shown in FIG. 47. Whilst the levels of the CD138 expression, marker which derived from immortal cell of B lineage appeared to be consistent among the cross-lineage tri-hybrid cell population, the expressions of markers originating from primary cells seemed to vary. In this particular example, there was a relatively small percentage of cells which did not co-express either CD4 or CD11b with CD138 (see FIG. 47a and b). When STmMm cells were analysed for co-expression of CD4 and CD11b (see FIG. 47 c), approximately 82% of cells did so. Effectively, 82% of the cell population expressed all three CD markers, with only 5% of cells being CD138 positive without co-expressing either CD4 or CD11b. Each of these various populations can be subsequently isolated by standard techniques such as FACS, MACS or single cell cloning, etc. and expanded into separate cross-lineage tri-hybrid cultures processing phenotypic characteristics different from each other whilst maintaning in-culture homogeneity.

When cytotoxic CD8 positive lymphocytes where used in creation of STmMm tri-hybrids, the rat anti-mouse CD8-PerCp antibodies were used instead of anti-CD4-PerCp for CD co-expression on resulting tri-hybrid cells. As seen from FIG. 48, 97 to 100% of the tri-hybrid cells were positive for CD138 (FIG. 48a and b) whilst 56% or 57% of these cells co-expressed CD8 (FIG. 48b) or CD11b (FIG. 48a). At least 40% of the tri-hybrid population expressed all three markers CD138, CD8 and CD11b (FIG. 48c).

In case of double positive CD4$^+$CD8$^+$ T cells, the first analysis was carried in the same manner as for cytotoxic T cells. FIG. 49 shows FACS profile of CD138, CD11b and CD8 expression on resulting tri-hybrid. 98-100% of tri-hybrid cells were positive for CD138 with 57-60% of the entire population being positive for all three lineage markers (FIG. 49c). Co-expression of CD138 and CD8 was detected on 93% of the cells (FIG. 49b). In the second step, the tri-hybrid cells were checked for co-expression of CD8 and CD4. The cells were labelled with rat anti-mouse CD8-PE and rat anti-mouse CD4-FITC antibodies (BD Pharmingen). FIG. 50 shows FACS profile of CD8 and CD4 expression. Whilst 95% of the tri-hybrid cells expressed CD8 on the surface, only 50% of cells co-expressed CD4 at the same time. Notably, practically the entire CD4 positive population was also positive for CD8.

4.6.2. Cross-lineage Tri-hybrid Production from Two Immortal Mouse Lymphoid Cells, and One Primary Mouse Monocyte This example details creation of a cross-lineage tri-hybrid cell line from two immortal mouse B lymphoid cells (Sp2) and one primary mouse monocyte. The cross-lineage tri-hybrid line was labelled as SSMm followed by a serial number.

4.6.2.1. Cell Preparation for SSMm Cross-lineage Tri-hybrid Production

The preparation of Sp2 cells used in the creation of SSMm cross-lineage tri-hybrids was described previously in Section 1.1.4 The primary mouse CD11b$^+$CD90$^-$B220$^-$CD49b$^-$NK1.1$^-$Ly6G$^{-/low}$ monocytes derived from peripheral blood were used in these experiments. The isolation of primary mouse monocytes from peripheral blood has been described previously (Section 1.3.5).

4.6.2.2. Cell Hybridisation Protocol for SSMm Cross-lineage Tri-hybrid Production The cell hybridisation protocol for SSMm cross-lineage tri-hybrid production was the same as that used for STmMm cross-lineage tri-hybrid production (see Section 4.6.1.2).

4.6.2.3. Confirmation of SSMm Cross-lineage Tri-hybrid Status

After a SSMm cross-lineage tri-hybrid cell line had been stable under normal culture conditions (see Section 1.1) for 6 months, the cross-lineage tri-hybrid cell population was analysed for the expression of lineage specific CD markers.

Double staining or labelling with rat anti-mouse CD138-PE and rat anti-mouse CD11b-FITC antibodies (BD Pharmingen) was applied to profile cross-lineage marker expression of the resulting cross-lineage tri-hybrid. FIG. 51 shows a typical CD profile of such cross-lineage tri-hybrid cells. The expression of oncogene-linked marker CD138 appeared to be constant in the cross-lineage tri-hybrid cells with only 7% of cells being negative for CD138. A large proportion of the cells (70%) did also express CD11b on their surface whilst the remaining 23% of CD138 positive cells were negative for surface expression of CD11b.

4.7. Cross-lineage Chimeric Tri-hybrid Production Using Human and Non-human Mammalian Cells This example details creation of cross-lineage chimeric tri-hybrids using human and non-human mammalian cells, specifically mouse. It is understood that the same principle can be applied in generating cross-lineage tri-hybrids from other mammalian cells.

4.7.1. Cross-lineage Chimeric Tri-hybrid Production from One Immortal Mouse Lymphoid Cell, One Immortal Human Lymphoid Cell and One Primary Either Mouse or Human Monocyte Creation of a cross-lineage chimeric tri-hybrid cell line from one immortal mouse B lymphoid cell (Sp2), one immortal human B lymphoid cell (WIL2NS) and one primary either mouse or human monocyte. The cross-lineage tri-hybrid line was labelled as SWMm where mouse monocyte was used and SWMh where human monocyte was used. In each instance, the abbreviated name of tri-hybrid was followed by a serial number.

4.7.1.1. Cell Preparation for SWMm and SWMh Cross-lineage Chimeric Tri-hybrid Production The preparation of Sp2 and WIL2NS cells used in the creation of SWMm and SWMh cross-lineage chimeric tri-hybrids was described previously in Section 1.1.4 and Section 1.1.3, respectively. The primary mouse CD11b$^+$CD90$^-$B220$^-$CD49b$^-$NK1.1$^-$Ly6G$^{-/low}$ monocytes derived from peripheral blood were used in these experiments. The isolation of primary mouse monocytes from peripheral blood has been described previously (Section 1.3.5). Human monocytes were isolated from mixed lymphocytes sourced from spleen, peripheral blood or umbilical cord blood. The isolation of monocytes was based on the expression of CD14 marker and in some instances low levels of CD16 expression either FACS or magnetic beads as described earlier in Section 1.3.3.1.1. There appeared to be no difference in hybridisation parameters or resulting cross-lineage tri-hybrids when monocytes from different lymphoid tissues were used.

4.7.1.2. Cell Hybridisation Protocol for SWMm and SWMh Cross-lineage Chimeric Tri-hybrid Productions The cell hybridisation protocol for SWMm and SWMh cross-lineage tri-hybrid production were the same as that used for STmMm cross-lineage tri-hybrid production (see Section 4.6.1.2).

4.7.1.3. Confirmation of SWMm and SWMh Cross-lineage Chimeric Tri-hybrid Status

After SWMm and SWMh cross-lineage chimeric tri-hybrid cell lines had been stable under normal culture conditions (see Section 1.1) for 6 months, the cross-lineage chimeric tri-hybrid cell populations were analysed for the expression of lineage specific CD markers.

Double staining for expression of human CD71 and mouse TfR was performed to establish chimerism of the resulting tri-hybrids. FIG. 52 shows typical FACS profiles of such analysis with 100% of the cells being positive for both human and mouse transferin receptors. This indicates tri-hybrid reliance on both mouse and human cell division controls.

Depending on mouse or human source of primary monocytes, double staining or labelling with rat anti-mouse CD138-PE and rat anti-mouse CD11b-FITC antibodies (BD Pharmingen) or rat anti-mouse CD138-PE and mouse anti-human CD14-FITC antibodies (BD Pharmingen) were applied to profile cross-lineage marker expression of the resulting cross-lineage chimeric tri-hybrids. FIG. 53 shows typical CD profiles of such cross-lineage chimeric tri-hybrid cells. The expression of oncogene-linked marker CD138 derived from mouse Sp2 cell line appeared to be dependant on mouse or human source of monocytes. The percentage of mouse CD138 positive cells dropped from 84% in SWMm tri-hybrids to 29% in SWMh tri-hybrids. However 96% of SWMh chimeric tri-hybrid cells were positive for human CD19 derived from WIL2NS (see FIG. 54), whilst none of the cells in SWMm chimeric tri-hybrid expressed human CD19.

EXAMPLE 5

5. Enrichment of Cross-lineage Tri-hybrids for Cells with Specific Cross-lineage Phenotypes Based on Distribution of CD Markers The following Section provides an example of establishing sublines of cross-lineage tri-hybrid cell lines based on different phenotypic characteristics. The approach was based on the analysis of lineage specific cell surface markers, intracellular expression of lineage specific markers, presence of RNA transcripts of lineage specific markers, karyotyping, and/or secretion of lineage specific proteins. Cross-lineage tri-hybrid cells with desired characteristics were isolated from the general population by FACS. The example below is based on a WWM cross-lineage tri-hybrid which had two tri-hybrid populations based on expression of CD14: positive and negative. However, the example is in no way limited to particular cross-lineage tri-hybrid or marker chosen.

The WWM cross-lineage tri-hybrid cells were sorted into CD14 positive and CD14 negative fractions and each of the fractions was expanded and maintained in the culture separately for 3 months. FIG. 22b shows more than 95% of cross-lineage tri-hybrid cells retained CD14 expression whereas the cell population in FIG. 22c continued to be negative for CD14. This demonstrates that it is possible to isolate and establish different homogeneous cell populations derived from the same cross-lineage tri-hybrid line.

Confirmation of Cross-lineage Tri-hybrid Through RT-PCR

In order to verify the cross-lineage tri-hybrid nature of the created sub-lines, original cross-lineage tri-hybrid cells, $CD19^+CD14^+$ enriched subculture and CD 14 negative subculture were subjected to RT-PCR assays for CD14. Human $CD14^+$ monocytes were used as positive control. The control cells were isolated from peripheral blood using FACS as previously described (Section 1.3.3).

Briefly, total RNA was prepared from cultured cells using the RNeasy kit (RNeasy Mini kit, Qiagen). cDNA synthesis was performed with the cDNA-Kit (Amersham Pharmacia) according to the manufacturer's protocol, and PCR was performed essentially as described by Sewing et al. The PCR reaction mixture was analysed by agarose gel (2%) electrophoresis and visualised by ethidium bromide staining. The oligonucleotide primer pairs had the sequences 5'-primer 5'-CACACTCGCCTGCCTTTTCC-3' (SEQ ID NO: 1) and 3'-primer 5' GATTCCCGTCCAGTGTCAGG-3' (SEQ ID NO: 2) for amplifying a PCR product of 450 bp.

As shown in the FIG. 23, the RT-PCR revealed the presence of CD14 mRNA transcripts in both the original WWM culture containing cells and in the $CD14^+$ enriched subculture of original WWM culture. CD 14 mRNA was also detected in the WWM subculture lacking surface CD14 at a level comparable to that of the human $CD14^+$ monocytes.

EXAMPLE 6

6. Karyotyping

Karyotyping of cross-lineage tri-hybrids was performed to establish cytogenic characteristics of cross-lineage tri-hybrids as well as to confirm their hybrid origins.

6.1. Karyotyping of Original Cell Lines

As an example, the cells of K562 and WIL2NS cell lines were karyotyped for early and later passages to record any chromosomal instability of the original cell lines. It was found that for a given cell line, e.g. K562 line, the karyotype of a freshly thawed line was identical to that of a cell line which was maintained under normal culture conditions for a few months.

FIGS. 24 and 25 depict a typical karyotype of K562 and WIL2NS cells, respectively. In both cases, a total of 20 G-banded metaphase cells were examined at 400 bphs.

The karyotyping results showed that K562 cell line contained a single clone with a triploid characteristic, i.e. having a modal number of 69 chromosomes with various chromosome abnormalities. In contrast, WIL2NS cell line contained five diploid clones with chromosome number of 47 to 48 with distinctly deferent chromosome abnormalities when compared to K562 cells. The representation of clones in WIL2NS cell line is as follows:
CLONE 1 constitutes 10%
CLONE 2 constitutes 55%
CLONE 3 constitutes 10%
CLONE 4 constitutes 20%
CLONE 5 constitutes 5%

Table 2 (below) summarises the complex karyotypes of K562 and WIL2NS cell lines. There are no shared abnormalities between two cell lines. The chromosome abnormalities present in all clones of WIL2NS cell lines are highlighted in blue.

| Name | K562 | WIL2-NS | | |
|---|---|---|---|---|
| Clone | 1 (100%) | 1 (10%) | 2 (55%) | 3 (10%) |
| Chrom | 69 | 47 | 47 | 48 |
| 1 | | | | |
| 2 | inv(2)(q33q35) | | | |
| 3 | −3 | | | |
| 4 | | | | |
| 5 | +der(5)t(5; ?)(q11.2; ?) | | | |
| 6 | dup(6)(p21.1p23) | | | |

-continued

| Chrom | | | | |
|---|---|---|---|---|
| 7 | | | | |
| 8 | | der(8)t(1; 8)(p32; p23) | der(8)t(1; 8)(p32; p23) | der(8)t(1; 8)(p32; p23) |
| 9 | −9, del(9)(p13), der(9)t(9; 9)(p12; q22) | | | |
| 10 | der(10)t(3; 10)(p21; p24) | | | |
| 11 | | | | |
| 12 | | | | |
| 13 | −13, add(13)(p11.1) | +13 | +13 | +13 × 2 |
| 14 | −14 | der(14)t(5; 14)(p10; p12) | der(14)t(5; 14)(p10; p12) | der(14)t(5; 14)(p10; p12) |
| 15 | | | | |
| 16 | | | | |
| 17 | add(17)(p13) × 2 | dup(17)(q22) | dup(17)(q22) | dup(17)(q22) |
| 18 | der(18)t(1; 18)(p32; q23) | | | |
| 19 | | | | |
| 20 | −20 | | | |
| 21 | der(21)t(1; 21)(q12: p11.1) | | der(21)t(3; 21)(q21; p11.1) | der(21)t(3; 21)(q21; p11.1) |
| 22 | −22 | | | |
| XY | XX, −X | XY | XY | XY |
| Markers | +mar1, mar2, +mar3, +mar4, +mar+5 | | | |

| | Name | WIL2-NS | |
|---|---|---|---|
| | Clone | 4 (20%) | 5 (5%) |
| | Chrom | 47 | 47 |
| | 1 | del(1)(q32q42) | del(1)(q32q42) der(1)t(1; 3)(p34.4; q42) |
| | 2 | | |
| | 3 | | |
| | 4 | | |
| | 5 | | |
| | 6 | | |
| | 7 | | |
| | 8 | der(8)t(1; 8)(p32; p23) der(8)t(8; 15)(q24.1; q22) | der(8)t(1; 8)(p32; p23) der(8)t(8; 15)(q24.1; q22) |
| | 9 | | |
| | 10 | | |
| | 11 | | |
| | 12 | | |
| | 13 | +13 | +i(13)(q10) |
| | 14 | der(14)t(5; 14)(p10; p12) | der(14)t(5; 14)(p10; p12) |
| | 15 | | |
| | 16 | | |
| | 17 | dup(17)(q22) | dup(17)(q22) |
| | 18 | | |
| | 19 | | |
| | 20 | | |
| | 21 | der(21)t(3; 21)(q21; p11.1) | der(21)t(3; 21)(q21; p11.1) |
| | 22 | | |
| | XY | XY | XY |
| | Markers | | |

6.2. Karyotyping of Cross-lineage Tri-hybrids Used for Protein Expression

The cross-lineage tri-hybrids derived from various combinations of immortal and primary cells of three different lineages and further used for expression of desired proteins were karyotyped. These karyotypes were also compared to those of the original immortal cell lines, which were used in the creation of the cross-lineage tri-hybrids.

6.2.1. Karyotyping of KBT Cross-lineage Tri-hybrid Lines

Two KBT cross-lineage tri-hybrid lines derived from the K562 immortal myeloid cell line and primary B and T lymphocytes were karyotyped. The KBT cross-lineage tri-hybrid derived from activated B cells (CD20$^+$CD72$^+$) and double positive T cells (CD4$^+$CD8$^+$) with various types of cells based on their CD expression characteristics (Section 4.2.3) was also karyotyped for comparison. FIG. 26 shows a typical karyotype of KBT cross-lineage tri-hybrid lines derived from K562+B(CD19$^+$)+T(CD4$^+$) hybridisation, dubbed KBT-1 line. It showed that a single cell clone of KBT-1 was near triploid, having a modal number of 66 chromosomes.

When a KBT cross-lineage tri-hybrid line derived from cell hybridisation of K562 cell, B (CD20$^+$CD72$^+$) cell and T (CD4$^+$CD8$^+$) cell, dubbed KBT-2 line, was karyotyped, it was found that the karyotyping of KBT-2 line (the line which had shown a variation of CD expressions in previous Section) consisted of four clones that were near triploid. Clone 1. Clone 2, Clone 3 and Clone 4 represented 45%, 30%, 15% and 10% of the cell population, respectively. Clone 4 had a modal chromosome number of 66, whereas the other clones having a modal chromosome number of 67 each. FIG. 27 shows a karyotyping of one of the clones of KBT-2 line.

The karyotypings of KBT-1 and KBT-2 lines are summarised in Table 3. The first column of the Table indicated the chromosome number. Some of the chromosomal changes such as del(3)(p14), der(4)t(4;?)(q25;?), +der(7)t(7;mar3)(q10;q10) and der(X)t(X;?;?)(q13;?;?) are shared by all cross-lineage tri-hybrids regardless of subtype of primary lymphoid cells but not shared with K562 cells.

TABLE 3

A summary of a comparative analysis of KBT-1 and KBT-2 derived from different primary lymphoid cell subtypes and K562 myeloid cell line as a source of oncogene. Chromosome abnormalities of K562 line shared with KBT-1 and KBT-2 cross-lineage tri-hybrid lines are highlighted in blue. Chromosome abnormalities shared among the clones of the KBT cross-lineage tri-hybrid lines but not original K562 cell line, are highlighted in red. Chromosome abnormalities present in some of KBT cross-lineage tri-hybrids and derived from K562 line are highlighted in green.

| Name | K562 | KBT | | |
|---|---|---|---|---|
| Subline | | (CD19+)&(CD4+) | (CD20 + CD72+)&(CD8 + CD4+) | |
| No. Clone | 1 (100%) | 1 (100%) | 1 (45%) | 2 (30%) |
| No. Chrom | 69 | 65-66 | 66-68 | 65-67 |
| 1 | | −1 | der(1)t(1; ?4)(q21.3; ?q25) | der(1)t(1; ?4)(q21.3; ?q25) |
| 2 | inv(2)(q33q36) | inv(2)(q33q35) | inv(2)(q33q35) | inv(2)(q33q35) |
| 3 | −3 | −3, del(3) (p14) | −3, del(3) (p14) | −3, del(3) (p14) |
| 4 | | der(4)t(4; ?)(q25; ?) | del(4)(q25; q35) | der(4)t(4; ?)(q25; ?) |
| 5 | +der(5)t(5; ?)(q11.2; ?) | +der(5)t(5; ?)(q11.2; ?) | +der(5)t(5; ?)(q11.2; ?) | +der(5)t(5; ?)(q11.2; ?) |
| 6 | dup(6)(p21.1p23) | dup(6)(p21.1p23) | dup(6)(p21.1p23) | dup(6)(p21.1p23) |
| 7 | | +der(7)t(7; mar3)(q10q10) | +der(7)t(7; mar3)(q10q10) | +der(7)t(7; mar3)(q10q10) |
| 8 | | | | |
| 9 | −9, del(9)(p13), der(9)t(9; 9)(p12; q22) | 9, del(9)(p13), der(9)t(9; 9)(p12; q22) | −9, del(9)(p13), der(9)t(9; 9)(p12; q22) | −9, del(9)(p13), der(9)t(9; 9)(p12; q22) |
| 10 | der(10)t(3; 10)(p21; p24) | der(10)t(3; 10)(p21; p24) | der(10)t(3; 10)(p21; p24) | der(10)t(3; 10)(p21; p24) |
| 11 | | | | |
| 12 | | | | |
| 13 | −13, add(13)(p11.1) | −13, add(13)(p11.1) | −13, add(13)(p11.1) | −13, add(13)(p11.1) |
| 14 | −14 | −14 | −14 | −14 |
| 15 | | −15 | | |
| 16 | | | | |
| 17 | add(17)(p13) × 2 | add(17)(p13) × 2 | add(17)(p13) × 2 | add(17)(p13) × 2 |
| 18 | der(18)t(1; 18)(p32; q23) | der(18)t(1; 18)(p32; q23) | der(18)t(1; 18)(p32; q23) | der(18)t(1; 18)(p32; q23) |
| 19 | | | | |
| 20 | −20 | −20 | −20 | −20 |
| 21 | der(21)t(1; 21)(q12; p11.1) | der(21)t(1; 21)(q12; p11.1) | der(21)t(1; 21)(q12; p11.1) | der(21)t(1; 21)(q12; p11.1) |
| 22 | −22 | −22 | −22 | −22 |
| XY | XX, −X | X, −X, der(x)t(X; ?1; ?)(q13; ?; ?) | X, −X, der(x)t(X; ?1; ?)(q13; ?; ?) | X, −X, der(x)t(X; ?1; ?)(q13; ?; ?) |
| Markers | +mar1, mar2, +mar3 +mar4, +mar+5 | +mar2, +mar4, +mar5, +mar10 | +mar1, +mar2, +mar4 +mar5 | +mar1, +mar2, +mar4 +mar5 |

| Name | KBT | |
|---|---|---|
| Subline | (CD20 + CD72+)&(CD8 + CD4+) | |
| No. Clone | 3 (15%) | 4 (10%) |
| No. Chrom | 67-68 | 66 |
| 1 | der(1)t(1; 4)(p10; p10) | der(1)t(1; 4)(p10; p10) |
| 2 | inv(2)(q33q35) | inv(2)(q33q35) |
| 3 | −3, del(3) (p14) | −3, del(3) (p14) |
| 4 | | −4 |
| 5 | +der(5)t(5; ?)(q11.2; ?) | +der(5)t(5; ?)(q11.2; ?) der(5)t(5; ?D/G)(p10; p10) |
| 6 | dup(6)(p21.1p23) | dup(6)(p21.1p23) |
| 7 | +der(7)t(7; mar3)(q10q10) | +der(7)t(7; mar3)(q10q10) |
| 8 | | |
| 9 | −9, del(9)(p13), der(9)t(9; 9)(p12; q22) | −9, del(9)(p13), der(9)t(9; 9)(p12; q22) |
| 10 | der(10)t(3; 10)(p21; p24) | der(10)t(3; 10)(p21; p24) |
| 11 | | |
| 12 | | |
| 13 | −13, add(13)(p11.1) | −13, add(13)(p11.1) |
| 14 | −14 | −14 |
| 15 | | |
| 16 | | |
| 17 | add(17)(p13) × 2 | add(17)(p13) × 2 |
| 18 | der(18)t(1; 18)(p32; q23) | der(18)t(1; 18)(p32; q23) |
| 19 | | |
| 20 | −20 | −20 |
| 21 | der(21)t(1; 21)(q12; p11.1) | der(21)t(1; 21)(q12; p11.1) |
| 22 | −22 | −22 |
| XY | X, −X, der(x)t(X; ?1; ?)(q13; ?; ?) | X, −X, der(x)t(X; ?1; ?)(q13; ?; ?) |
| Markers | +mar1, +mar2, +mar4 +mar5 | +mar1, +mar2, +mar4 +mar5 |

6.2.2. Karyotyping of KWT Cross-lineage Tri-hybrid Lines

Three KWT cross-lineage tri-hybrid lines derived from the K562 immortal myeloid cell line, the WIL2NS immortal B lymphoid cell line and a primary T lymphocyte were karyotyped. KWT cross-lineage tri-hybrid derived from double positive T cells (CD4$^+$CD8$^+$) (dubbed KWT-3) with various types of cells based on their CD expression characteristics (Section 4.4.3) was also karyotyped for comparison.

FIGS. 28, 29 and 30 show typical karyotypes of KWT-1, KWT-2 and KWT-3 cross-lineage tri-hybrid lines, respectively. In each case a total of 20 G-banded metaphase cells were analysed at 400 bphs. KWT-1 contained a single clone that was near hexaploid (6n=138 chromosomes). The modal number of chromosomes ranged from 129 to 140 chromosomes with karyotypic heterogeneity, i.e all analysed cells shared some of the chromosome abnormalities. KWT-2 contained a single clone that was also near-hexaploid. The modal number of chromosomes ranged from 135 to 145 chromosomes with karyotypic heterogeneity. KWT-3 contained three clones that were hyperpentaploid (n>115). Clone 1, Clones 2 and 3 represents 55%, 20% and 25% of the cell population, respectively. The karyotypes of KWT cross-lineage tri-hybrids confirmed that genetic features of both K562 and WIL2-NS cell lines are retained in all KWT cross-lineage tri-hybrids regardless of the primary T cell type used in their creation. Table 4 summarises a comparative analysis of karyotypes of these KWT cross-lineage tri-hybrids (i.e. KWT-1, KWT-2 and KWT-3 lines).

TABLE 4

A comparative analysis of the KWT cross-lineage tri-hybrids derived from different types of primary T cells. Chromosome changes in KWT cross-lineage tri-hybrids shared with K562 cell line are highlighted in red. Chromosome changes shared between KWT cross-lineage tri-hybrids and WIL2NS cell line are highlighted in blue. Changes that are shared between different subtypes of the cross-lineage tri-hybrids but neither with K562 cell line nor WIL2NS cell line are highlighted in green.

| Name | K562 | WIL2 NS | | KWT | |
|---|---|---|---|---|---|
| Subline | | | | CD4+ | CD3 + CD5+ |
| Clone | 1 (100%) | 2 (55%) | 3 (10%) | 1 (100%) | 1 (100%) |
| Chrom | 69 | 47 | 48 | 129-140 | 135-142 |
| 1 | | | | −1 | −1 |
| 2 | inv(2)(q33q35) | | | −2, inv(2)(q33q35) | −2, inv(2)(q33q35) |
| 3 | −3 | | | −3, −3, | −3, −3, |
| 4 | | | | −4, | −4, |
| 5 | +der(5)t(5; ?)(q11.2; ?) | | | der(4)t(4; ?)(q35; ?) +der(5)t(5; ?)(q11.2; ?) × 2 | der(4)t(4; ?)(q35; ?) +5, +der(5)t(5; ?)(q11.2; ?) × 2 |
| 6 | dup(6)(p21.1p23) | | | +6, dup(6)(p21.1p23) | +6, dup(6)(p21.1p23) |
| 7 | | | | +7, +inv(7)(p13p22) | +inv(7)(p13p22) × 2 |
| 8 | | der(8)t(1; 8)(p32; p23) | der(8)t(1; 8)(p32; p23) | der(8)t(1; 8)(p32; p23) | der(8)t(1; 8)(p32; p23) |
| 9 | −9, del(9)(p13), der(9)t(9; 9)(p12; q22) | | | −9, −8, del(9)(p13), der(9)t(9; 9)(p12; q22) | −9, −8, del(9)(p13), der(9)t(9; 9)(p12; q22) × 2 |
| 10 | der(10)t(3; 10)(p21; 24) | | | +der(10)t(3; 10)(p21; 24) | +der(10)t(3; 10)(p21; 24) |
| 11 | | | | | |
| 12 | | | | −12 | −12 |
| 13 | −13, add(13)(p11.1) | +13 | +13 × 2 | add(13)(p11.1) | add(13)(p11.1) |
| 14 | −14 | der(14)t(5; 14)(p10; p12) | der(14)t(5; 14)(p10; p12) | −14, −14, der(14)t(5; 14)(p10; p12) | −14, −14, der(14)t(5; 14)(p10; p12) |
| 15 | | | | −15 | −15 |
| 16 | | | | | |
| 17 | add(17)(p13) × 2 | dup(17)(q22) | dup(17)(q22) | −17, dup(17)(q22) × 2, add(17)(p13) × 2 | −17, dup(17)(q22) × 2, add(17)(p13) × 2 |
| 18 | der(18)t(1; 18)(p32; q23) | | | −18, −18 | −18, −18 |
| 19 | | | | | |
| 20 | −20 | | | | +20 |
| 21 | der(21)t(1; 21)(q12; p11.1) | der(21)t(3; 21)(q21; p11.1) | der(21)t(3; 21)(q21; p11.1) | der(21)t(1; 21)(q12; p11.1) | der(21)t(1; 21)(q12; p11.1) |
| 22 | −22 | | | −22 | −22 |
| XY | XX, −X | XY | XY | XXXY, −X, −X | XXXY, −X, −X |
| Markers | +mar1, mar2, +mar3, +mar4, +mar+5 | | | +mar1, mar2 × 2, +mar3, +mar4, +mar+5, +mar11 | +mar1, +mar2 × 2, +mar3, +mar4, +mar+5, +mar9, +mar11 |

| Name | KWT | | |
|---|---|---|---|
| Subline | CD4 + CD8+ | | |
| Clone | 1 (55%) | 2 (20%) | 3 (25%) |
| Chrom | 124-139 | 125-131 | 131-132 |
| 1 | +1 | +1 | +1 |
| 2 | +2, +2, inv(2)(q33q35) | +2, +2, inv(2)(q33q35) | +2, +2, ider(2)(q10)inv(2)(q33q35) |
| 3 | −3 | −3 | −3 |
| 4 | | | |
| 5 | +der(5)t(5; ?)(q11.2; ?) | +der(5)t(5; ?)(q11.2; ?) | +der(5)t(5; ?)(q11.2; ?) |
| 6 | +6, dup(6)(p21.1p23) | +6, dup(6)(p21.1p23) | +6, dup(6)(p21.1p23) |
| 7 | +inv(7)(p13p22) | +inv(7)(p13p22) | +inv(7)(p13p22), dic(7; 9)(p22; q11) |
| 8 | der(8)t(1; 8)(p32; p23) | der(8)t(1; 8)(p32; p23) | der(8)t(1; 8)(p32; p23) |
| 9 | del(9)(p13), der(9)t(9; 9)(p12; q22) | −9, del(9)(p13), der(9)t(9; 9)(p12; q22) | −9, del(9)(p13), der(9)t(9; 9)(p12; q22) |

TABLE 4-continued

A comparative analysis of the KWT cross-lineage tri-hybrids derived from different types of primary T cells. Chromosome changes in KWT cross-lineage tri-hybrids shared with K562 cell line are highlighted in red. Chromosome changes shared between KWT cross-lineage tri-hybrids and WIL2NS cell line are highlighted in blue. Changes that are shared between different subtypes of the cross-lineage tri-hybrids but neither with K562 cell line nor WIL2NS cell line are highlighted in green.

| | | | |
|---|---|---|---|
| 10 | +10, +10, +der(10)t(3; 10)(p21; 24) × 2 | +10, +10, +der(10)t(3; 10)(p21; 24) × 2 | +10, +10, +der(10)t(3; 10)(p21; 24) × 2 |
| 11 | | | |
| 12 | | | |
| 13 | +13, +13, add(13)(p11.1) | +13, +13, add(13)(p11.1) | +13, +13, add(13)(p11.1) |
| 14 | −14, der(14)t(5; 14)(p10; p12) | −14, der(14)t(5; 14)(p10; p12) | −14, der(14)t(5; 14)(p10; p12) |
| 15 | | | |
| 16 | | | |
| 17 | dup(17)(q22q23), add(17)(p13) × 2, +add(17)(p13) | dup(17)(q22q23), add(17)(p13) × 2, +add(17)(p13) | dup(17)(q22q23), add(17)(p13) × 2, +add(17)(p13) |
| 18 | +18, der(18)t(1; 18)(p32; q23) | +18, der(18)t(1; 18)(p32; q23) | +18, der(18)t(1; 18)(p32; q23) |
| 19 | +19 | +19 | +19 |
| 20 | −20 | −20 | −20 |
| 21 | der(21)t(1; 21)(q12; p11.1) | der(21)t(1; 21)(q12; p11.1) | der(21)t(1; 21)(q12; p11.1) |
| 22 | | | |
| XY | XXXY | XXXY | XXXY |
| Markers | +mar1, mar2, +mar3, +mar4 × 2, +mar+5 × 2 | +mar1, mar2, +mar3, +mar4 × 2, +mar+5 × 2 | +mar1, mar2, +mar3, +mar4 × 2, +mar+5 × 2 |

6.2.3. Karyotyping of WWM Cross-lineage Tri-hybrid Lines

A WWM cross-lineage tri-hybrid line derived from two immortal B lymphoid cells (2 WIL2NS lines) and primary monocyte (CD14$^+$) were karyotyped. The subline of this cross-lineage tri-hybrid enriched for CD14$^+$ cells was also karyotyped. FIGS. 31A and 31B show karyotypes of the original WWM cross-lineage tri-hybrid and its CD14$^+$-enriched subline, respectively. In each case G-banded metaphase chromosomes from a total of 20 cells were analysed at 400 bphs. The original WWM cross-lineage tri-hybrid contained a single dominant clone that had a modal number of 47 chromosomes, found in 11 cells (55%). However, remaining 9 cells analysed range from near triploid (with random chromosome loss) to near tetraploid (with random chromosome loss). There was no consistency between any of these cells. On the other hand, karyotype of CD14$^+$-enriched WWM cross-lineage tri-hybrid indicated a single clonal abnormality detected in 19 cells. Only one tetraploid cell was detected.

Table 5 summarises comparative analysis of karyotypings of the WWM cross-lineage tri-hybrid lines. The chromosomal characteristics shared with WIL2-NS cells are highlighted in blue.

| Name | WIL2-NS | | | |
|---|---|---|---|---|
| Subline | | | | |
| Clone | 1 (10%) | 2 (55%) | 3 (10%) | 4 (20%) |
| Chrom | 47 | 47 | 48 | 47 |
| 1 | | | | del(1)(q32q42) |
| 2 | | | | |
| 3 | | | | |
| 4 | | | | |
| 5 | | | | |
| 6 | | | | |
| 7 | | | | |
| 8 | der(8)t(1; 8)(p32; p23) | der(8)t(1; 8)(p32; p23) | der(8)t(1; 8)(p32; p23) | der(8)t(1; 8)(p32; p23) der(8)t(8; 15)(q24.1; q22) |
| 9 | | | | |
| 10 | | | | |
| 11 | | | | |
| 12 | | | | |
| 13 | +13 | +13 | +13 × 2 | +13 |
| 14 | der(14)t(5; 14)(p10; p12) | der(14)t(5; 14)(p10; p12) | der(14)t(5; 14)(p10; p12) | der(14)t(5; 14)(p10; p12) |
| 15 | | | | |
| 16 | | | | |
| 17 | dup(17)(q22) | dup(17)(q22) | dup(17)(q22) | dup(17)(q22) |
| 18 | | | | |
| 19 | | | | |
| 20 | | | | |
| 21 | | der(21)t(3; 21)(q21; p11.1) | der(21)t(3; 21)(q21; p11.1) | der(21)t(3; 21)(q21; p11.1) |
| 22 | | | | |

-continued

| | | | | |
|---|---|---|---|---|
| XY | XY | XY | XY | XY |

| Name | WIL2-NS | WWM | |
|---|---|---|---|
| Subline | | CD14+ | CD14 + en |
| Clone | 5 (5%) | 55% | 95% |
| Chrom | 47 | 47 | 47 |

| Chrom | WIL2-NS 5 (5%) | WWM CD14+ 55% | WWM CD14+ en 95% |
|---|---|---|---|
| 1 | del(1)(q32q42) der(1)t(1; 3)(p34.4; q42) | | |
| 2 | | | |
| 3 | | | |
| 4 | | | |
| 5 | | | |
| 6 | | | |
| 7 | | | |
| 8 | der(8)t(1; 8)(p32; p23) der(8)t(8; 15)(q24.1; q22) | der(8)t(1; 8)(p32; p23) | der(8)t(1; 8)(p32; p23) |
| 9 | | | |
| 10 | | | |
| 11 | | | |
| 12 | | | |
| 13 | +i(13)(q10) | +13 | +13 |
| 14 | der(14)t(5; 14)(p10; p12) | der(14)t(5; 14)(p10; p12) | der(14)t(5; 14)(p10; p12) |
| 15 | | | |
| 16 | | | |
| 17 | dup(17)(q22) | dup(17)(q22) | dup(17)(q22) |
| 18 | | | |
| 19 | | | |
| 20 | | | |
| 21 | der(21)t(3; 21)(q21; p11.1) | der(21)t(3; 21)(q21; p11.1) | der(21)t(3; 21)(q21; p11.1) |
| 22 | | | |
| XY | XY | XY | XY |

EXAMPLE 7

7. Detection of the EBV Genome by PCR

For PCR assays and for a given cross-lineage tri-hybrid cell line, the genomic DNA was extracted from $5 \times 10^6$ cells of the cross-lineage tri-hybrid. MOLT-4 cells were used as negative control whereas CO 88BV59-1 as positive control using a QIAamp DNA Micro kit (Qiagen), according to the manufacturer's instructions. In the qualitative PCR assay, the BamHI W region of the EBV genome was amplified with specific primers. The upstream and downstream primer sequences were 5'-CAAGAACCCAGACGAGTCCGTA-GAA-3' (SEQ ID NO: 3) and 5'-AAGAAGCATGTATAC-TAAGCCTCCC-3', (SEQ ID NO: 4) respectively (Kimura, et al., 1999). 10 ng of the extracted DNA was added to the reaction mixture containing 10 mM Tris-HCl (pH 8.3), 1.5 mM MgCl$_2$, 50 mM KCl, 200 µM dNTP, 0.6 µM each primer and 0.5 U of Taq polymerase (Lomb Life Science). Following initial denaturation for 2 min at 95° C., 28 cycles of 15 sec at 95° C. and 1 min at 60° C. were carried out using the Gene-Amp PCR system 9600 (Perkin Elmer). The amplified samples were separated on a 2% agarose gel.

The results from the assays above indicated that all of the cross-lineage tri-hybrids established in this invention were found to be negative for EBV genome.

EXAMPLE 8

8. Mycoplasma Test

Mycoplasma tests on any cell lines used and cross-lineage tri-hybrid lines created in this invention were carried out using a mycoplasma PCR detection kit (Lomb Scientific) according to the manufacturer's instructions. The results from the test indicated that all the cell lines and the cross-lineage tri-hybrids were found to be mycoplasma free.

EXAMPLE 9

9. Expression of Proteins in Cross-lineage Tri-hybrid Expression System and their Characterisation The tri-hybrid cross lineage cell system embodied in the present invention may be used for the preparation of a range of biologics, including but not limited to biological molecules such as proteins, peptides, carbohydrates, lipids and chimeric molecules thereof. Specifically the biological molecules may include cytokines, growth factors hormones, receptors or chimeric molecules or fragments thereof. The skilled addressee will understand that a desired biological molecule such as a protein expressed from the tri-hybrid cross lineage cell may be secreted, membrane bound or both. The skilled addressee will further understand that various protein subunits may be co-expressed in the cross-lineage tri-hybrid cell, for example immunoglobulin expression and more specifically monoclonal antibody production. The skilled addressee will further understand that the tri-hybrid cross lineage cell may also be used to express a range of functional protein or peptide fragments, for example in the case of immunoglobulins, fragments such as Fab, Fab', F(ab')$_2$ and Fv fragments, including single chain Fv fragments.

Expression of desired protein may be accomplished in the tri-hybrid cell system by somatic cell hybridisation of the tri-hybrid cell with a partner cell that expresses the desired protein (Section 9.1). Alternatively, the tri-hybrid cells may be subjected to conventional gene transfection protocols to facilitate expression of a desired protein (Section 9.2.1 and 9.2.2). In a further embodiment, the tri-hybrid cells may express multiple target proteins concurrently by using either somatic cell hybridisation or conventional gene transfection or both (Section 9.3).

The following examples illustrate the expression of a number of different types of proteins, in cross-lineage tri-hybrid cells. The examples also demonstrate that proteins, specific to a particular differentiated cell type can be expressed in the same cross-lineage tri-hybrid cells (e.g. immunoglobulin and CD54).

9.1. Hybridisation of the Tri-hybrid Cross Lineage Cell with a Cell Expressing a Desired Protein.

9.1.1. Expression of Human GM-CSF

The WWM cross-lineage tri-hybrid line enriched for CD14 positive cells (described in Section 5) was used as a partner cell line in this particular example. Activated human CD4 positive lymphocytes isolated as described in Section 1.3.3.1.1 were used as a source of human GM-CSF. The electrical cell hybridisation procedure was essentially the same as that used for the creation of WWM cross-lineage tri-hybrids as described in Section 4.3.2. After the resulting hybrid of WWM and CD4+ cultured T cells became stable it was maintained as a cell line and labeled as ProGM.

Results of Human GM-CSF Expression

ProGM supernatants were tested for human GM-CSF by sandwich type ELISA. A 96 well ELISA plate (Corning) was coated with 50 µl of purified rabbit polyclonal anti-GM-CSF antibody at 10 µg/ml at 4° C. overnight. After removal of the antibody solution, the residual protein binding sites on the plates were blocked with 100 µl of PBS containing 5% of BSA (5% BSA-PBS). Then 50 µl of a culture supernatant from the ProGM hybrid cell line were added to the wells and incubated for 2 hours at 37° C. After washing with PBS containing 0.05% of Tween 20 (Tween-PBS) three times, they were incubated with 50 µl of rabbit anti-GM-CSF antibody at 10 µg/ml at room temperature for 1 hour. After washing 3 times with Tween-PBS, they were incubated with a 200-fold diluted peroxidase-conjugated anti-rabbit immunoglobulin for 2 hours at room temperature. After rinsing three times with Tween-PBS, the final reaction was visualized by incubating with ABTS and 0.01% hydrogen peroxide. The absorbance at 415 nm was measured. Recombinant human GM-CSF was used as a standard. All analyses were done in duplicates for a given sample. The results showed that ProGM produced human GM-CSF at the range of 0.7 to 1.1 µg/ml/$10^6$ cells under non-optimised culture conditions.

The characterization of hGM-CSF derived from ProGM hybrid by Western blot and immuno-precipitation confirmed that the ProGM hybrid produced fully human GM-CSF exhibiting glycoprotein forms identical to the glycoforms naturally secreted by human lymphocytes. The supernatants collected from ProGM hybrid were diluted 100 fold prior to the analysis. Immunoblot NC membranes for Western blot analysis (Millipore) and biotinylated rat anti-human GM-CSF antibody (R&D systems) at concentration 0.1 µg/ml were used for the Western blot detection. In FIG. 32, the Western blot of hGM-CSF secreted by ProGM hybrid (lane 4) showed the same heterogeneity of its forms as GM-CSF secreted by PHA activated human lymphocyte culture (lane 2). The molecular weight distribution of GM-CSF expressed in both ProGM and lymphocyte cultures ranged between 18 kDa to 35 kDa. In the presence of tunicamycin, which inhibits the addition of carbohydrate chains to asparagine residues, the higher molecular weight molecules (i.e. 35 kDa) were not detected indicating that the observed heterogeneity is due to a different degree of glycosylation (lane 5). The molecular weights of GM-CSF forms produced by either PHA activated lymphocytes or in the ProGM hybrid expression system were higher than the GM-CSF derived from E. coli (lane 6).

The supernatants of the ProGM hybrid cultured with or without supplementing with 10 µg/ml of tunicamycin were collected and incubated overnight at 40° C. with rat anti-human GM-CSF antibody or rabbit anti-mouse GM-CSF antibody raised against E. coli-derived human or mouse GM-CSF respectively. Protein A-Sepharose (Invitrogen) was added and further incubated for 3 hours at room temperature. The recovered resin was washed thoroughly with 0.15 M NaCl, 0.5% NP-40, 10 mM Tris-HCl, pH 8.0. Bound proteins were solubilised with Laemmli sample buffer and subjected to SDS-PAGE. As shown in FIG. 33, the molecular weight of GM-CSF secreted by the ProGM hybrid ranges from 18 kDa to 35 kDa which is similar to naturally occurring forms. This heterogeneity is due to different glycosylation at two N-glycosylation and several O-glycosylation sites. In the presence of tunicamycin, the higher molecular weight bands were not detected whereas proteins of lower molecular weight 18-22 kDa accumulated. This data confirms that hGM-CSF derived from ProGM hybrid is secreted as human glycoprotein.

9.1.2. Expression of Human Immunoglobulins

The KWT cross-lineage tri-hybrid line derived from antigen-experienced T cell ($CD3^+CD5^+$) (dubbed KWT-2) with phenotypic markers as determined by FACS (see Section 4.4.3 for more details) and karyotyped as described in Section 6.2.2, was used for expression of human immunoglobulin via electrical cell hybridisation. Specifically, the KWT-2 cross-lineage tri-hybrid was used as a partner cell line in this particular example. Primary CD40 activated either IgM positive or IgG positive B cells isolated as described in Section 1.3.3 were used as a source of human Ig. The electrical cell hybridisation procedure was essentially the same as that used for the creation of KWT cross-lineage tri-hybrid lines as described in Section 4.4.2. After the resulting hybrids became stable, they were maintained and labelled as ProIM or ProIG cell lines (see Section 1.1).

Results of Human Immunoglobulin Expression

The supernatants from ProIM and ProIG were analysed for the presence of IgM or IgG by ELISA described earlier (see Section 1.3.3). The cells were seeded in round bottom 96 well plates at $1\times10^5$ cells per well and cultured under standard conditions for 24 hours. The cell count and viability were done using hemacytometer and trypan blue exclusion. The results are summarised in Tables 6A and 6B. Each value is given as mean±SD of three independent measurements.

TABLE 6A

Cell growth and IgM production of ProIM cells

| Exp | Viable cell density (cells/ml) | IgM production (ng/ml) | IgM productivity (ng/$10^4$ cells/ 24 hours) |
|---|---|---|---|
| 1 | $1.2 \times 10^5$ | 310 ± 12.3 | 26.7 |
| 2 | $1.4 \times 10^5$ | 512 ± 20.1 | 36.6 |
| 3 | $1.1 \times 10^5$ | 298 ± 10.5 | 27.1 |
| 4 | $1.2 \times 10^5$ | 387 ± 15.1 | 32.3 |
| 5 | $1.5 \times 10^5$ | 701 ± 23.4 | 46.7 |

TABLE 6B

Cell growth and IgG production of ProIG cells

| Exp | Viable cell density (cells/ml) | IgG production (ng/ml) | IgG productivity (ng/$10^4$ cells/ 24 hours) |
|---|---|---|---|
| 1 | $8.0 \times 10^4$ | 84 ± 5.9 | 10.5 |
| 2 | $8.1 \times 10^4$ | 85 ± 3.7 | 10.5 |
| 3 | $8.0 \times 10^4$ | 76 ± 4.3 | 9.5 |
| 4 | $8.2 \times 10^4$ | 89 ± 6.1 | 10.9 |
| 5 | $8.2 \times 10^4$ | 82 ± 4.3 | 10.0 |

IgG subclasses and light chain subtypes were detected using the biotinylated mouse anti-human IgG1 (clone HP6069), IgG2 (clone HP6002), IgG3 (clone HP6047), IgG4 (clone HP6025) (ICN Biomedicals) and the biotinylated goat anti-human kappa and lambda chain (Biosource). The bound biotinylated antibody was detected with ALP-conjugated streptavidin.

The results showed that both IgM and IgG produced by ProIM and ProIG cells, respectively, had K light chain and IgG was of IgG2 class.

9.1.3. Expression of Human CD54

Methodology for Human CD54 Expression

The KWT cross-lineage tri-hybrid derived from mature T helper cell (CD4$^+$) (dubbed KWT-1) with phenotypic markers as determined by FACS (see Section 4.4.3 for more details) and karyotyped as described in Section 6.2.2 was further used for expression of human CD54 via electrical cell hybridisation Specifically, the KWT cross-lineage tri-hybrid was used as a partner cell line in this particular example. Primary human CD54 positive T cells isolated as described in Section 1.3.3 were used as a source of human CD54 molecule. The hybridisation procedure was essentially the same as that used for the creation of KWT cross-lineage tri-hybrid lines (see Section 4.4.2). After the resulting hybrid became stable, it was maintained as a cell line under standard culture conditions (see Section 1.1) and labelled as ProCD54.

Results of hCD54 Expression

The expression of CD54 on the surface of ProCD54 cells was verified by using a FACS analysis. As 100% of original KWT cross-lineage tri-hybrid cells expressed CD4 on their surface (see FIG. 19), the CD4 expression on ProCD54 cell surface was used as a reference for the stability of the resulting cell line. In brief, 1×10$^5$ cells per 100 μl aliquots were labelled with mouse anti-human CD54-FITC and mouse anti-human CD4-PE antibodies following the same protocol as described in Section 1.3.3.1 (isolation of CD54$^+$ T cells). The typical profile of CD4 and CD54 expression on the surface of ProCD54 cells is shown in FIG. 34a. Approximately 72% of the original ProCD54 cells were positive for CD54 whilst 100% of the cells retained its CD4 expression, even though the levels of the CD4 expression appeared to be somewhat lower than that of KWT cross-lineage tri-hybrid cells. After setting appropriate gates, the CD4$^+$CD54$^+$ cell population with mid to high levels of CD54 expression (approximately 42% of the total cell population) was gated and sorted out (FIG. 34a). The sorted cells were re-suspended in standard culture medium and maintained in the culture for a few months. The resulting sub-line was labelled as ProCD54EX. The sub-line was then analysed for its CD4 and CD54 expression employing the same protocol as described earlier in this Section. The typical profile of CD4 and CD54 expression on the surface of ProCD54EX is shown in FIG. 34b. As can be seen from the figure, at least 98% of the cells maintained expression of both CD4 and CD54 after 6 months of culture under standard conditions. Even further the expression of CD54 became homogeneous at mid levels.

The ProCD54 and ProCD54EX were also analysed for the presence of a soluble CD54 in the tissue culture supernatants by using human CD54 (ICAM-1) ELISA (R&D systems) according to the manufacturer's instructions. The supernatants were collected at day 7 in culture at least 3 times. Supernatants of the KWT cross-lineage tri-hybrid partner cell line were used as a negative control. All measurements were done with the same sample in duplicate. In brief, microtitre plates were coated with a murine monoclonal antibody directed against human soluble ICAM-1. After incubation with control, the samples or the standards in appropriate dilution, a horseradish peroxidase (HRP) conjugated polyclonal antibodies to human soluble ICAM-1 was added. After addition of substrate and stop solution the optical density of each well was determined within 30 minutes, using a microplate reader set to 45 nm. The results are summarised in Table 7.

TABLE 7

A range of concentrations of soluble CD54 (ICAM-1) in the KWT cross-lineage tri-hybrid partner cell line, ProCD54 and ProCD54EX cell lines

| Cell line | Lowest concentration, ng/ml | Highest concentration, ng/ml |
| --- | --- | --- |
| KWT | 0 | 0 |
| ProCD54 | 420 | 1320 |
| ProCD54EX | 910 | 2870 |

The molecular weight of soluble CD54 shedding from ProCD54 and ProCD54EX was determined by gel electrophoresis and Western blot analysis. In brief, the protein concentration in the supernatants was determined by protein assay (R&D systems) and adjusted to 1.8 mg/ml. Electrophoresis was performed by SDS-PAGE. A total of 30 ml of the sample was loaded on the gel in non-reducing sample buffer. After electrophoresis, the proteins were transferred to a polyvinylidene difluoride membrane (Bio-Rad). The blotted membrane was blocked with non-fat dry milk (5%) in TBS-Tween buffer (TBST) and agitated for 2 hours with a mouse anti-human ICAM-1 antibody (1:100 dilution in TBST). After the samples were washed with TBST, the secondary reagent, goat anti-mouse IgG linked to HRP (1:10,000 dilution) was added. After repeated washing with TBST, the membrane was rinsed with water. All incubations were carried out at room temperature. FIG. 35 shows that sCD54 present in the supernatants of both ProCD54 and ProCD54EX as a single species of approximately 82 kDa, which corresponds to that of soluble CD54 detected in human serum.

The expression of mRNA for human CD54 in both ProCD54 and ProCD54EX cells was verified by RT-PCR. Total RNA was extracted using commercial kit and RT-PCR detection of gene expression was performed as previously describe in Section 5. A human ICAM-1 primer set [sense, 5'-CCGGAAGGTGTATGAACTG-3'; (SEQ ID NO: 5) anti-sense, 5'-TCCATGGTGATCTCTCCTC-3' (SEQ ID NO: 6)] were used to probe cDNA reverse transcribed from experimental and control RNA samples. A primer pair for cyclophilin was included in each assay as an internal control [sense, 5'-TGTTCTTCGACATTGCCGTCGAC-3'; (SEQ ID NO: 7) anti-sense 5'-GCATTTGCCATGGACAAGATGCCAGGA-3' (SEQ ID NO: 8)]. PCR reaction products were electrophoresed in 3% agarose gels in Tris-acetate buffer containing ethidium bromide, and UV-induced fluorescent bands were photographed and digitized. The FIG. 36 shows an RT-PCR analysis of mRNA for human ICAM-1 in ProCD54 and ProCD54EX. The KWT cross-lineage tri-hybrid cells, which do not express CD54 on the cell surface also show very low transcription of ICAM-1 gene.

9.2. Transfection of the Tri-hybrid Cross Lineage Cell Line with a Gene Encoding a Desired Protein Specific genes can be introduced into cultured cells by a number of conventional techniques including vector-mediated gene transfer. In one embodiment of the present invention the tri-hybrid cross lineage cells were transiently transfected with a gene encoding a desired protein. This allows gene products, either RNA or protein, to be obtained within hours of DNA uptake. In an alternative embodiment of the present invention the tri-hybrid cross lineage cell was stably transfected with a gene encoding a desired protein. This involves the plasmid vector DNA being integrated into the host cell chromatin.

9.2.1. Transient Transfection

The KBT cross-lineage tri-hybrid derived from mature B cell (CD19$^+$) and mature T helper cell (CD4$^+$) with 100% of cross-lineage tri-hybrid cells sharing both B and T cell phenotypic markers as determined by FACS (see Section 4.2.3) and karyotyped as described in Section 6.2.1 was used for gene transfection experiments. As an example of transient transfection of cells of a cross-lineage tri-hybrid line with a desired protein, the cells of a KBT cross-lineage tri-hybrid were transfected with human IL-4 receptor alpha chain (hIL4—Rα).

Method

The preparation of PBML cells from a bone marrow sample has been described in Section 1.3.1. hIL4—Rα cDNA was cloned from a total of 1×10$^6$ PBML cells incubated with 100 ng/ml of recombinant human IL-4 (R&D systems) for 24 hours under standard culture conditions. Total RNA was extracted (RNeasy Mini Kit, Qiagen) and cDNA was synthesised using the First Strand cDNA purification kit (Amersham Pharmacia). PCR was used to amplify the hIL4—Rα cDNA. The amplification was carried out with sense primer 5β-AGGGGCGCGCAGATAATTAAA-3' (SEQ ID NO: 9) and anti-sense primer 5'-AGTGGGGCCAATCACCT-TCATA-3' (SEQ ID NO: 10). A nested PCR was used to add two BamHI restriction sites to the hIL4—Rα fragment [sense primer 5'-GGATCCGCGCAGATAATTAAAGA-3', (SEQ ID NO: 11) anti-sense primer 5'-GGATCCAAATCACCT-TCATACCAT-3' (SEQ ID NO: 12]. The amplified cDNA was diluted and subjected to an initial denaturation of 1 min at 94° C. followed by 31 cycles of 20 seconds at 94° C., 45 seconds at 59° C., 3 minutes at 72° C. The IL4R cDNA fragment was ligated into the cloning vector pGEM-T (Promega) and transfected JM109 competent cells (Promega). Plasmid DNA was prepared by using a Plasmid Mini Kit (Qiagen)

For electroporation, 7×10$^6$ of the KBT cells suspended in 350 μl of complete TC medium (see Section 1.1) were mixed with 30 μg of cDNA plasmid. The transfection was performed by a single pulse (25 kV/m, 1050 μF, 34-37 msec pulse width) from an Eurogentec Easyject Pulser. Subsequently, the cells were incubated in six well tissue culture plates in complete TC medium supplemented with 100 ng/ml of recombinant hIL4.

Cell extracts were prepared by freeze-thaw procedure after 24, 48 and 72 hours after transfection. The non-transfected KBT and PBML cells were used as a negative control and a positive control, respectively. Total protein content of the cell extracts was determined by using the Bio-Rad protein assay (Bio-Rad Laboratories). Equal amounts of cell extracts (approximately 2 mg) were immunoprecipitated with 3 μg of anti-hIL4-Rα chain (BD Pharmingen 551894) by using 20 mg of protein A insolubilised on Sapharose 4B fast flow (Sigma). The immunoprecipitates were washed twice in dilution buffer (0.1% Triton X-100 and bovine hemoglobin in TSA solution, one time in TSA solution and another in 0.05 M TRIS-Cl (pH 6.8) solution solubilised with Laemmli buffer, boiled, and resolved by TRIS-glycine 4% to 12% SDS-PAGE. The TSA solution contained 0.01 M TRIS-Cl (pH 8.0), 0.14 M NaCl, and 0.025% sodium azide). In some experiments, 75 μg of protein content of the cell extracts were directly resolved by SDS-PAGE without prior immunoprecipitation Western blot analyses were performed by transferring the proteins from polyacrylamide gels onto Hybond-ECL nitrocellulose membranes (Amersham) at 25 V for 2 hours in TRIS-glycine buffer containing 25 mM TRIS, 192 mM glycine, 0.1% SDS, 100 μM sodium vanadate, and 20% methanol. The blots were treated for 1 hour with blocking buffer (2.5% non-fat dry milk, 10 mM TRIS-Cl [pH 7.5], 100 mM NaCl, and 0.1% Tween 20) and then incubated with 2 μg/ml mouse anti-hIL4—Rα antibody in blocking buffer for another hour. Antibody binding was detected by incubating the blots for 1 hour with sheep anti-mouse immunoglobulin conjugated with horseradish peroxidase, followed by a 1-minute incubation with iodinated substrate and then enhanced chemiluminescence detection.

Results

FIG. 37 shows a Western blot analysis of cell extracts from a KBT cross-lineage tri-hybrid cell line transiently transfected with hIL4—Rα chain, 24, 48 and 72 hours after transfection. The hIL4—Rα chain was detected in KBT cells transfected with hIL4—Rα chain 24 hours after transfection and the expression levels of hIL4—Rα chain increased progressively 48 and 72 hours after the transfection. Untransfected KBT cells served as a negative control for the hIL4—Rα chain. Cell extracts from human PBML cells used for the preparation of hIL4—Rα cDNA served as a positive control for the hIL4—Rα chain.

9.2.2. Stable Transfection

As an example of stable transfection of cells of a cross-lineage tri-hybrid cell line with a desired protein, the cells of a KBT cell line were transfected with the human Interleukin 2 (hIL-2) gene.

Method

The hIL-2 expression vector pBC12/RSV/IL2 (IS) which contains a rat preproinsulin II gene under the control of RSV long terminal repeat sequences was used for transfection. The entire insulin leader region and the insulin sequences encoding a translation initiation codon have been incorporated. This chimeric hIL-2 mRNA produces significantly more hIL2 protein than does hIL-2 mRNA containing the natural hIL-2 leader and initiation codon (Cullen, 1988).

The dihydrofolate reductase gene sequences (dhFr) were inserted into pBC12/RSV/IL2 vector via ligation with SV40/dhFr gene fragment (Subramani et al., Mol. Cell. Biol. 1:854, 1981) resulting in pBC12/RSV/IL-2/dhFr plasmid containing an entire murine dhFr gene under the control of the SV40 virus early region promoter and in which the hIL-2 and dhFr genes were positioned in the same orientation.

Prior to transfection, the cultured KBT cells were subjected to mutagenesis with 0.1 mM of the polycyclic aromatic hydrocarbon racemic 3a,4b-dihydroxy-1a,2a-epoxy-1,2,3,4-tetrahydrobenzo[c]phenanthrene (B[c]PHDE) for 90 minutes (Carothers et al., Proc. Natl. Acad. Sci. 87:5464-68, 1990). Selection for dhFr-clones was based on dependency for hypoxanthine and thymidine and followed a 6-day expression period (Urlaub et al., Proc. Natl. Acad. Sci. 77(7): 4216-20, 1980). Resulting dhFr deficient KTB cells (KBTdhFr-) were maintained in standard medium supplemented with 10$^{-4}$M hypoxanthine and 10$^{-5}$M thymidine.

In transfection, the cultured KBTdhFr-cells were washed with PBS three times and re-suspended in 0.8 ml of PBS. 60 μg of pBC12/RSV/IL2/dhFr vector were added to cell suspension, and the suspension was transferred into a plastic electroporation cuvette and incubated on ice for 10 min. Electroporation was carried out at 75 kV/m and 25 μF using a standard electroporation protocol with a Gene-pulser electroporation unit (Bio-Rad). After pulsing, the cuvette was incubated on ice for 10 min. The cells were then transferred into the flasks and cultured in standard medium without hypoxanthine and thymidine. Surviving cells were cloned using single cell cloning technique (see Section 1.1.2) and established lines were evaluated for hIL-2 secretion.

Results

Expression of hIL-2 mRNA in transfected KBT (KBT TR-IL2) cells was verified by PCR with hIL-2 specific primers. Human CD8$^+$ T cells obtained from PBML via magnetic bead sorting (as described in Section 1.3.3.5) and Jurkat cell line, Clone E6-1 were used as a positive control. K562 cells and non-transfected KBT hybrid cells were used as negative controls. Total RNA was extracted from the transfected KBT cells after various treatments in RNeasy Mini kit (Qiagen) following the manufacturer's instructions. The following primers were the hIL-2 primers used based on published sequences (Wang et al, 1989):

(SEQ ID NO: 13)
5'primer = 5'-GAATGGAATTAATAATTACAAGAATCCC-3'

(SEQ ID NO: 14)
3'primer = 5'-TGTTTCAGATCCCTTTAGTTCCAG-3'

Amplification was performed for 35 cycles. PCR cycles consisted of 40 seconds at 94° C., annealing temperature for hIL2 was 55° C., followed by an extension for 40 seconds at 72° C. The PCR products were visualised in 2% agarose gels with ethidium bromide. The results are given in FIG. 38. The levels of expression are similar to those obtained from CD8$^+$ human T lymphocytes and Jurkat cells. Non-transfected KBT cells and K562 cells were used as negative controls.

Intracellular IL-2 was detected using BD FastImmune™ CD4 intracellular IL-2 Detection Kit (BD Pharmingen) according to the manufacturer's instructions. FACS analyses were performed using a BD FACSCalibur. Initially, CD4$^+$ cells were gated based on forward scatter and fluorescence threshold as well as forward and side scatter. It was followed by the analysis of gated population based on CD69 (activated CD4$^+$ T cells) and intracellular IL-2 expression. A FACS profile of IL-2 expression in the KBT TR-IL2 cells is shown in FIG. 39. Non-transfected KBT cells were used as a control. Approximately 41% of the KBT cells were positive for CD69 activation molecule. 92% of the KBT TR-IL2 cells stained positive for intracellular hIL-2 (R1+R2). The hIL-2 negative cells were part of CD69 positive population, whereas CD69 negative cells were all positive for intracellular hIL2.

Secretions of hIL-2 at thirty days and ninety days after transfection were verified by ELISA. In brief, 1×10$^6$ hIL-2 transfected KBT cells were incubated in a 24-well tissue culture plate at 37° C. for 24 hours. The supernatant was collected, and hIL-2 activity was measured by hIL-2 ELISA kit (R&D systems). The supernatants were diluted to fit the detection range of hIL-2 ELISA kit. Recombinant hIL-2 (R&D systems) was used as a positive control. ELISA analysis showed hIL-2 secretion rates ranging from 660 ng/10$^6$ cells/24 hours to 3300 ng/10$^6$ cells/24 hours.

The resulting KBT cell line stably transfected with hIL2 and secreting hIL2 was labelled as ProL2.

9.3. Concurrent Expression of Target Proteins Combining Hybridisation and Transfection As an example of concurrent protein expression using the tri-hybrid system, the tri-hybrid cells were hybridised with human sIgM$^+$CD25$^+$ B lymphocytes in order to express hIgM, followed by stable transfection with hIL-2. The hybrid cell system that was stably expressing both hIgM and hIL-2 was further subjected to transient transfection with hIL-4Rα. In this example, hIgM represented the first protein, hIL-2 represented the second concurrently expressed protein and hIL-4Rα represented the third concurrently expressed protein. Alternatively, the tri-hybrid cells were stably transfected with hIL-2 followed by somatic cell hybridization with human shIgM$^+$CD25$^+$ B cells. Following confirmation that both hIL-2 and hIgM were being expressed from the hybrid cell system, the hybrid cell system was further subjected to transient transfection with hIL-4Rα. In this example, hIL-2 represented the first protein, hIgM represented the second concurrently expressed protein and hIL-4Rα represented the third concurrently expressed protein.

9.3.1 Cell Preparation

The KBT cross-lineage tri-hybrid derived from mature B cell (CD19$^+$) and mature T helper cell (CD4$^+$) with 100% of cross-lineage tri-hybrid cells sharing both B and T cell phenotypic markers as determined by FACS (see Section 4.2.3) and karyotyped as described in Section 6.2.1 was used in these experiments. In some instances, dhFr deficient KBT cells (KBTdhFr-) derived from the mutagenesis process described in section 9.2.2 and maintained in standard medium supplemented with 10$^{-4}$M hypoxanthine and 10$^{-5}$M thymidine were used in the experiments. Also, hIL-2 transfected cell line KBT TR-IL2 (see section 9.2.2) was also used in some instances. Primary CD40 activated sIgM positive B cells isolated from PBMC as described in Section 1.3.3 and activated via CD40 pathway as described in Section 2.2 were used as a source of human sIgM B cells for hybridisation. For these particular experiments, isolation of sIgM$^+$ B cells was also based on concurrent surface expression of CD25 (human IL-2 receptor) using FACS after 5 days in the culture. CD8$^+$ T cells were isolated from thymuses using MACS CD4 Multisort kit as described in Section 1.3.3.5.

9.3.2 Somatic Cell Hybridization for Production of a First Protein or Co-production of a Second Protein The electrical cell hybridisation procedure between a KBT cell, or KBTdhFr-cell or line KBT TR-IL2 cell and shIgM$^+$CD25$^+$ B cell (subset of memory B cells) was essentially the same as that used for the creation of KBT cross-lineage tri-hybrid lines as described in Section 4.4.2. After the resulting hybrids became stable, they were maintained as described in Section 1.1. Co-expression of shIgM and CD25 by the resulting hybrid was verified through FACS analysis (see FIG. 62) and production of hIgM was analysed by ELISA. In instances where KBT TR-IL2 cells were used for hybridisation with shIgM$^+$CD25$^+$ B cell, production of hIL-2 was also analysed concurrently with hIgM.

9.3.3 Stable Transfection with the Second Protein

When somatic cell hybridisation was performed prior to the system's stable transfection with hIL-2, the hIgM producing system was subjected to transfection with hIL-2 using methodology described in section 9.2.2. The concurrent production of both hIgM and hIL-2 was verified by ELISA.

9.3.4 Transient Transfection with the Third Protein

A stable hybrid system secreting both hIgM and hIL-2 was further transiently transfected via electroporation with the hIL-4Ra gene, using the same approach as described in Section 9.2.1. The co-production of hIgM, hIL-2 and hIL-4Rα was confirmed by ELISA.

Results

The production levels of three proteins concurrently expressed and co-produced by the cells of the same hybrid cell system are summarized in the Table 7a and Table 7b. For the analysis, the cells were grown in 24 well plates to the density of 0.5×10$^5$ cells/ml for the expression of one protein, 1.2×10$^5$ cells/ml for the expression of two proteins and 3.2×10$^5$ cells/ml for the expression of three proteins. Not only was the system able to produce three proteins concurrently, but also the production level of the first protein increased following co-expression of the secondary protein and it was further augmented by the expression of the third protein. In the same manner, the production of the second protein was augmented by the expression of the third protein.

TABLE 7a

Typical production levels of proteins concurrently expressed by the same hybrid cell system with somatic hybridization being first expression method

| Production level | Expression of one protein | Expression of two proteins | Expression of three proteins |
|---|---|---|---|
| hIgM, ng/ml/24 hours | 3,382 ± 284 | 12,547 ± 593 | 33,891 ± 835 |
| hIL-2, ng/ml/24 hours | | 18,524 ± 660 | 74,012 ± 1,034 |
| hIL-4Ra, ng/ml/24 hours | | | 13,892 ± 791 |

TABLE 7b

Typical production level of proteins concurrently expressed by the same hybrid cell system with stable transfection being the first expression method

| Production level | Expression of one protein | Expression of two proteins | Expression of three proteins |
|---|---|---|---|
| hIL2, ng/ml/24 hours | 3,228 ± 284 | 19,875 ± 843 | 81,124 ± 1,435 |
| hIgM, ng/ml/24 hours | | 5,321 ± 476 | 18,067 ± 613 |
| hIL-4Ra, ng/ml/24 hours | | | 12,766 ± 897 |

EXAMPLE 10

10. Adaptation to Serum-free Culture Conditions for ProGM Hybrid Production

In order to demonstrate the robustness of ProGM hybrid cells for commercial production, the culture volume was scale up to spinner flasks with working volume of 1.2 L and culturally adapted for a serum-free environment.

Methodology

The highest hGM-CSF producing clones of ProGM hybrid were adapted to grow in a serum-free environment by gradual reduction of FCS content to 7.5, 5.0, 2.5, 1.0, 0.5 and 0%. Only the sub-cultures demonstrating the most robust cell growth and production of hGM-CSF above were transferred to the consecutive lower serum environments. Each selected sub-culture was frozen down in our standard medium with 5% DMSO for storage. Two serum-free culture media were used for adaptation purposes. Commercially available defined serum and protein free medium Hybri-Max (Sigma) or Excel (JHR) with some modifications were used. Cell viability was assessed by trypan blue exclusion on day 7. The concentration of hGM-CSF was determined by ELISA on the same day.

Results

The results of the adaptation to serum-free culture conditions are given in Table 8.

TABLE 8

Production of hGM-CSF by ProGM in serum-free condition

| | Serum Content (%) | | | | | | |
|---|---|---|---|---|---|---|---|
| | 10.0 | 7.5 | 5.0 | 2.5 | 1.0 | 0.5 | 0 |
| Max cell density ($\times 10^6$ cells/ml) | 1.8 | 1.0 | 1.0 | 0.8 | 0.6 | 0.5 | 0.5 |
| Concentration of hGM-CSF (μg/ml) | 0.911 | 1.431 | 1.412 | 2.345 | 3.971 | 4.231 | 3.825 |
| Production (μg/ml/$10^6$ cells) | 0.5 | 1.431 | 1.412 | 2.93 | 6.62 | 8.46 | 7.65 |

In all subcultures of ProGM hybrid, the production of hGM-CSF increased with reduction of the serum and protein content. In spite of low cell density in serum-free cultures, the amount of hGM-CSF in the serum-free medium was approximately 4 times higher than that obtained under standard culture conditions. When normalized to the cell concentration, the production rate of hGM-CSF increased by 15 times.

EXAMPLE 11

11.1. Production in Spinner Flasks

Methodology

Spinner flasks with 1.2 L working volume were stirred at 50 r.p.m. ProGM hybrid cells adapted to growth in serum-free environment (ProGMsf) were inoculated at a concentration of $1 \times 10^5$ cells/ml. The culture was incubated at 37° C. in a humidified atmosphere containing 5% $CO_2$. The maximum cell density achieved was $5 \times 10^5$ cells/ml. The viable cells were determined using trypan blue exclusion method. Daily changes of medium were performed for up to 9 days. The cell suspension (600 ml) was centrifuged at 1000 r.p.m. for 10 min, the medium was removed and replaced by fresh medium and the cells were returned to the spinner flask. The concentration of hGM-CSF secreted was determined by ELISA. Each well was coated with 100 μl rat anti-human GM-CSF (R&D) diluted 1:500. After washing with PBS containing 0.05% v/v Tween 20 (PBS-T), 100 μl of standard rhGM-CSF (Invitrogen) in PBS-5% v/v BSA, over the range 0.195-200 ng/ml, or samples 100 μl each diluted 100-fold were added to the wells in duplicates. All incubations were carried out at 37° C. for 1 h. Afterwards, the plates were washed with PBS-T and 100 μl rabbit anti human GM-CSF (R&D) antibody diluted 1:1,000 in PBS-BSA-T was added and after incubation and washing, 100 μl of goat anti-rabbit immunoglobulins-HRP conjugate diluted 1:1,000 in the same buffer was added. Once more, the plates were incubated and washed, and 100 μl of substrate was added. Optical densities were measured at 450 nm.

Results

The relatively low cell density of $5 \times 10^5$ cells per ml indicates suboptimal culture conditions for cell growth of ProGMsf. Further optimization of culture conditions including glucose content and other supplements may be required in order to obtain higher densities (in order of $10^6$ cells/ml). Close monitoring of lactate and ammonium content is also warranted. Despite the suboptimal growth, the concentration of hGM-CSF in culture supernatants ranged between 2.8 to 4.2 μg per ml. When normalised to cell density and time, ProGMsf exhibited production rates between 0.6 to 0.9 μg of hGM-CSF per ml per $10^6$ cells per 24 hours. For comparison, a production of 0.3 μg of protein per ml per $10^6$ cells per 24 hours in CHO cells is considered to be high.

11.2. Purification of Human GM-CSF Produced by ProGM Hybrid Cell Line

Methodology

The supernatant from ProGMsf culture was concentrated approximately 10-fold at 40° C. with PM-10 membrane (Amicon). The sample concentrate was loaded onto immunoaffinity column, prepared by coupling rat anti-human GM-CSF against E. coli-derived human GM-CSF to Affi-Gel 10 (Bio-Rad) according to the manufacturer's protocol, equilibrated with PBS (137 mM NaCl, 3 mM KCl, 8 mM $Na_2HPO_4$, 1.5 mM $KH_2PO_4$) and the bound proteins were eluted with 0.1 mM sodium-citrate, pH 2.8. The proteins eluted from the affinity column were then loaded onto RP 300 HPLC column and eluted with acetonitrile gradient 0-60% over 60 minutes at a flow rate of 0.1 ml/min. The resulting elution profile is shown in FIG. 40. Aliquots recovered from RP-HPLC were collected for ELISA, silver staining and Western blot analysis.

Results

Table 9 shows the recovery of hGM-CSF from the typical two-step purification. The initial recovery from the affinity column was only 59% and only 2% of hGM-CSF was lost after RPHPLC. There are a number of possibilities accounting for low recovery after affinity purification. The binding capacity of the affinity column might be lower than the amount of hGM-CSF in supernatants of ProGMsf as 13% of hGM-CSF was lost in flow through and washing steps. The low recovery could also be due to lower affinity of rat antibodies raised against E. coli-derived hGM-CSF compared to glycosylated forms of hGM-CSF produced by ProGMsf hybrid. The other potential improvement in the final yields would be a development of a better optimized elution conditions. In FIG. 41 (see Section 12), Western blot of fractions collected after RP-HPLC demonstrated that hGM-CSF eluted in fractions 24-36 (eluting at 24-36 minutes). High molecular weight forms (28-32 kDa) eluted in fractions 24 to 27, whereas lower molecular weight molecules (18-22 kDa) eluted in fractions 34 to 36. These chromatographic conditions did not fully resolve different molecular weight forms of hGM-CSF, especially in the high and middle molecular weight fractions.

The profile obtained with silver staining and Western blot profiles were essentially identical, suggesting that only hGM-CSF related proteins bound to the affinity column. Several molecular weight species of native hGM-CSF were observed.

TABLE 9

Two-step purification of hGM-CSF derived from ProGMsf

| Sample | Volume ml | Concentration of hGM-CSF by ELISA µg/ml | Total hGM-CSF in sample µg | Yield % |
| --- | --- | --- | --- | --- |
| Supernatant of ProGMsf | 60 | 3.825 | 229.5 | 100 |
| Affinity column flow through | 60 | 0.467 | 28.02 | 12 |
| Wash step | 10 | 0.112 | 1.12 | 0.5 |
| Eluate | 3 | 44.78 | 134.34 | 59 |
| RP-HPLC immunoassay positive fractions | | | | |
| 24 | 0.1 | 144.5 | 14.45 | 6.3 |
| 25 | 0.1 | 159.7 | 15.97 | 7.0 |
| 26 | 0.1 | 102.8 | 10.28 | 4.5 |
| 27 | 0.1 | 123.1 | 12.31 | 5.4 |
| 28 | 0.1 | 163.6 | 16.36 | 7.0 |
| 29 | 0.1 | 146.8 | 14.68 | 6.0 |
| 30 | 0.1 | 71.72 | 7.172 | 3.0 |
| 31 | 0.1 | 144 | 1.324 | 0.6 |
| 32 | 0.1 | 9.38 | 0.938 | 0.4 |
| 33 | 0.1 | 10.72 | 1.072 | 0.5 |
| 34 | 0.1 | 184.6 | 18.46 | 8.0 |
| 35 | 0.1 | 161.3.3 | 16.16 | 7.0 |
| 36 | 0.1 | 19.71 | 1.971 | 0.9 |
| Total | | | 131.1557 | |
| Total Yield | | | | 57 |

EXAMPLE 12

12. Glycosidase Digestion

Methodology

Purified human GM-CSF derived from the ProGMsf hybrid was heat-denatured for 3 min at 100° C. in 1% SDS, 1M P-mercaptoethanol, 100 mM sodium phosphate, pH 7.0, 0.8 U of sequencing grade PNGase F (Sigma) was added and incubated for increasing periods at 37° C.

Results

As seen in FIG. 43 after N-digestion, hGM-CSF forms derived from ProGMsf hybrid migrated in a time dependent manner to the position near the hGM-CSF-derived from E. coli. However, none of the bands after digestion corresponded to unglycosylated form produced by E. coli. These results suggest that hGM-CSF derived from ProGMsf hybrid is glycosylated at both N- and O-glycosylation sites and that molecular weight distribution is caused by heterogeneous glycosylation. This finding of O-glycosylation in all molecules of hGM-CSF is important from viewpoint of immunogenicity of unprotected O-glycosylation sites; it has been reported that recombinant human GM-CSF lacking O-glycosylation developed antibodies in clinical trials.

The data suggests that the ProGMsf hybrid cells secrete three classes of hGM-CSF according to the N-glycosylation sites: molecules with both sites glycosylated (25-35 kDa, 2N-type); molecules with either site glycosylated (20-25 kDa, 1N-type); and molecules with neither site glycosylated (18-20 kDa, 0N-type).

Although the invention has been described with reference to specific examples, it will be appreciated by those skilled in the art that the invention may be embodied in many other forms, in keeping with the broad principles and the spirit of the invention described herein.

REFERENCES

Ainai et al., Hum Antibodies 15:139-154, 2006
Airoldi et al, Cancer Research 61:1285-1290, 2001
Blackwood et al, Science 281: 60-63, 1998
Boerner et al, J. Immunol. 147: 86-95, 1991;
Carothers et al, Proc. Natl. Acad. Sci. 87:5464-68, 1990
Christensen et al J. Biol. Chem. 282(27): 19463-19472
Cullen, B. R., 1988. DNA, 7: 645-650
Durocher et al, Nucleic Acids Res 30(2):e9, 2002;
Durocher et al, Nucleic Acids Res 30(2):e9, 2002;
Feizi Nature 314: 53-54, 1985;
Girard et al, Cytotechnology 38:15-21, 2002;
Gramer et al, Biotechnology 13 (7):692, 1995

Hartman et al, J Immunol 164: 944-953, 2000;
Hosoi et al, Cytotechnology 7: 25-32, 1991
Hosoi et al, Cytotechnology 7: 25-32, 1991
Hosoi et al, Cytotechnology 7: 25-32, 1991
Hur et al, Cell Prolif 38: 35-45, 2005;
Jordan et al, Cytotechnology 26:39-47, 1998;
Jordan et al, Cytotechnology 26:39-47, 1998;
Kalantarov et al, Hum Antibodies 11: 85-96, 2002;
Karpas et al, Proc Natl Acad Sci USA 98:1799-1804, 2001
Kimura H. et al, 1999. J Clin Microbiol 37: 132-136
Kirman et al, Hybrid. Hybridomics 21: 405-414, 2002;
Kohler, G. and Milstein, C. Nature, 256, 495-497 1975
Li et al, Proc Natl Acad Sci USA 103(10):3557-3562, 2006
Li et al, Proc Ntl Acad Sci USA 95: 3650-3654, 1998;
Mahaworasilpa, T. L. (1992). Cell Electro-Dynamics: The mechanics of living cells in intense alternating electric fields. PhD Thesis, University of New South Wales, Sydney, Australia
Marika et al, Curr Opin Genet Dev 11(2): 205-208, 2001
McIlroy D, Autran B, Cheynier R, et al. J. Virol.; 69:4737-4745 1995
Meissner et al, Biotechnol Bioeng 75(2):197-203, 2001
Miyaji et al., Cytotechnology 4: 173-180, 1990;
Miyaji et al., Cytotechnology 4: 39-43, 1990;
Miyaji et al, Cytotechnology, 3: 133-140, 1990;
Neil, G. A. and Zimmermann, U Electro, Meth. Enzymol 220, 174 1993
Parham et al, Cytotechnology, 35:181-187, 2001
Paulson et al, J. Biol. Chem. 264: 10931-10934, 1989
Pham et al, Biotechnol Bioeng 84(3):332-42, 2003
Pohl, H. Dielectrophoresis, Cambridge University Press, London 1978
Rademacher et al, Annu Rev Biochem 57: 785-838, 1988
Satoh et al, Cytotechnology 18:162-172, 1996
Satoh et al, Cytotechnology 13: 79-88, 1993
Satoh et al, Cytotechnology 13: 79-88, 1993
Schlaeger et al, Cytotechnology 30:71-83, 1999
Shinkawa et al, J. Biol. Chem. 278:3466-3473, 2003
Sugimoto et al, J Virol 73:9690-9691, 1999;
Toda et al, J Chromatogr B Analyt. Technol. Biomed. Life Sci. 787:197-206, 2003.
Traggiai et al, Nat Med 10: 871-875, 2004
Urlaub et al, Proc. Natl. Acad. Sci. 77(7): 4216-20, 1980
van Dijk et al, Curr. Opin. Chem. Biol. 5:368-374, 2001
Wang, A. M., Doyle. M. V., and Mark. D. F. Proc. Natl. Acad. Sci. USA, 86: 9717-9721, 1989
Wojciersyn, J. W. et al, J. Cell. Biol., 96, 151-159, 1983
Zafiropoulos et al, J. Immunol. Methods 200: 181-190, 1997
Zimmermann, U. (1982). Biochim. Biophys. Acta. 694, 227-277

---

The invention claimed is:

1. A hybrid cell generated by hybridisation of:
   a first cell, wherein said first cell is a cell derived from a common myeloid progenitor cell, wherein said cell derived from the common myeloid progenitor cell is optionally a myelomonocytic progenitor, monocyte, macrophage, eosinophil, neutrophil, dendritic cell or basophil;
   a second cell derived from a common lymphoid progenitor cell; and
   a third cell derived from a common lymphoid progenitor cell, and wherein said second cell and said third cell are not myeloma cells.

2. A hybrid cell according to claim 1 wherein said second cell is a cell derived from B lymphoid lineage and said third cell is a cell derived from B lymphoid lineage or wherein said second cell is a cell derived from T lymphoid lineage and said third cell is a cell derived from T lymphoid lineage.

3. A hybrid cell according to claim 1 wherein said second cell is a cell derived from B lymphoid lineage and said third cell is a cell derived from T lymphoid lineage.

4. The hybrid cell according to claim 1 wherein said cell derived from a common myeloid progenitor cell is an immortalised cell and/or derived from spleen, peripheral blood, umbilical cord blood or bone marrow.

5. The hybrid cell according to claim 3 wherein said cell derived from B lymphoid lineage is a pre-B cell, an immature B cell, a naïve B cell, an activated B cell or an effector B cell, wherein said effector B cell is optionally an antigen-experienced B-cell or a plasma cell.

6. The hybrid cell according to claim 3 wherein said cell derived from T lymphoid lineage is a pre-T cell, an immature T cell, a naïve T cell, an activated T cell or an effector T cell.

7. The hybrid cell according to claim 3 wherein said cell derived from B lymphoid lineage or T lymphoid lineage is an immortalised cell or wherein said cell derived from B lymphoid lineage or T lymphoid lineage is derived from lymphoid tissue, optionally peripheral blood, cord blood, spleen, bone marrow, thymus, tonsils, adenoids, or regional lymph node.

8. The hybrid cell according to claim 1 wherein at least one of the cells is a human cell or a mouse cell.

9. The hybrid cell according to claim 1 wherein said cell derived from a common myeloid progenitor cell is a K562 cell.

10. The hybrid cell according to claim 1 wherein said second cell or said third cell is a WIL2-NS cell or a MOLT4 cell.

11. The hybrid cell according to claim 3 wherein said cell derived from B lymphoid lineage is a WIL2-NS cell.

12. The hybrid cell according to claim 3 wherein said cell derived from said T lymphoid lineage is a MOLT4 cell.

13. The hybrid cell according to claim 1 wherein said first cell is a K562 cell, said second cell is a WIL2-NS cell and said third cell is a MOLT4 cell or wherein said first cell is a K562 cell, said second cell is a primary B cell and said third cell is a primary T cell or wherein said first cell is a primary human monocyte, said second cell is a WIL2-NS cell and said third cell is a primary T cell or wherein said first cell is a primary human myelomonocytic progenitor, said second cell is a WIL2-NS cell and said third cell is a primary human T cell or wherein said first cell is a K562 cell, said second cell is a WIL2-NS cell and said third cell is a primary T cell or wherein said first cell is a primary monocyte, said second cell is a WIL2-NS cell and said third cell is a WIL2-NS cell or wherein said first cell is a primary mouse monocyte and said third cell is a primary mouse T cell or wherein said first cell is a primary mouse monocyte or wherein said first cell is a primary human or mouse monocyte and said second cell is a WIL2-NS cell.

14. The hybrid cell according to claim 1 wherein said hybrid cell expresses a desired protein, more than one desired protein, two desired proteins or three desired proteins wherein any one or more of the proteins is an endogenous protein or a recombinant protein.

15. The hybrid cell according to claim 14 wherein said protein is a cytokine, a colony-stimulating factor, an interleukin, GM-CSF, interleukin 2, a receptor or fragment thereof, a soluble receptor, human IL-4 receptor alpha chain, CD54 or an immunoglobulin including IgM or IgG.

16. The hybrid cell according to claim 1 wherein said hybridisation is achieved by electrical means or chemical means.

17. The hybrid cell according to claim 1 further hybridised with a cell that expresses a protein of interest.

18. The hybrid cell of claim 1 wherein said hybridisation is carried out by hybridising three individual cells or wherein said hybridisation is carried out using three populations of cells wherein each said population includes a plurality of identical cell types.

19. The hybrid cell according to claim 1 wherein said hybrid cell is selected for a particular cell type-defining marker to permit the expression of a protein exhibiting a desired post-translational modification or desired functionality.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Homo sapiens

<400> SEQUENCE: 1
cacactcgcc tgccttttcc                                              20

<210> SEQ ID NO 2
<211> LENGTH: 20
<212> TYPE: DNA
<213> ORGANISM: Homo sapiens

<400> SEQUENCE: 2
gattcccgtc cagtgtcagg                                              20

<210> SEQ ID NO 3
<211> LENGTH: 25
<212> TYPE: DNA
<213> ORGANISM: Homo sapiens

<400> SEQUENCE: 3
caagaaccca gacgagtccg tagaa                                        25

<210> SEQ ID NO 4
<211> LENGTH: 25
<212> TYPE: DNA
<213> ORGANISM: Homo sapiens

<400> SEQUENCE: 4
aagaagcatg tatactaagc ctccc                                        25

<210> SEQ ID NO 5
<211> LENGTH: 19
<212> TYPE: DNA
<213> ORGANISM: Homo sapiens
```

```
<400> SEQUENCE: 5
ccggaaggtg tatgaactg                                                  19

<210> SEQ ID NO 6
<211> LENGTH: 19
<212> TYPE: DNA
<213> ORGANISM: Homo sapiens

<400> SEQUENCE: 6
tccatggtga tctctcctc                                                  19

<210> SEQ ID NO 7
<211> LENGTH: 23
<212> TYPE: DNA
<213> ORGANISM: Homo sapiens

<400> SEQUENCE: 7
tgttcttcga cattgccgtc gac                                             23

<210> SEQ ID NO 8
<211> LENGTH: 27
<212> TYPE: DNA
<213> ORGANISM: Homo sapiens

<400> SEQUENCE: 8
gcatttgcca tggacaagat gccagga                                         27

<210> SEQ ID NO 9
<211> LENGTH: 21
<212> TYPE: DNA
<213> ORGANISM: Homo sapiens

<400> SEQUENCE: 9 agggcgcgc agataattaa a                                                21

<210> SEQ ID NO 10
<211> LENGTH: 22
<212> TYPE: DNA
<213> ORGANISM: Homo sapiens

<400> SEQUENCE: 10
agtggggcca atcaccttca ta                                              22

<210> SEQ ID NO 11
<211> LENGTH: 23
<212> TYPE: DNA
<213> ORGANISM: Homo sapiens

<400> SEQUENCE: 11
ggatccgcgc agataattaa aga                                             23

<210> SEQ ID NO 12
<211> LENGTH: 24
<212> TYPE: DNA
<213> ORGANISM: Homo sapiens

<400> SEQUENCE: 12
ggatccaaat caccttcata ccat                                            24

<210> SEQ ID NO 13
<211> LENGTH: 28
<212> TYPE: DNA
```

```
<213> ORGANISM: Homo sapiens

<400> SEQUENCE: 13
gaatggaatt aataattaca agaatccc                                              28

<210> SEQ ID NO 14
<211> LENGTH: 24
<212> TYPE: DNA
<213> ORGANISM: Homo sapiens

<400> SEQUENCE: 14
tgtttcagat ccctttagtt ccag                                                  24
```